(12) United States Patent
Kimba et al.

(10) Patent No.: US 8,280,664 B2
(45) Date of Patent: Oct. 2, 2012

(54) XY-COORDINATE COMPENSATION APPARATUS AND METHOD IN SAMPLE PATTERN INSPECTION APPARATUS

(75) Inventors: Toshifumi Kimba, Tokyo (JP); Keisuke Mizuuchi, Yokohama (JP)

(73) Assignee: Ebara Corporation, Tokyo (JP)

( * ) Notice: Subject to any disclaimer, the term of this patent is extended or adjusted under 35 U.S.C. 154(b) by 512 days.

(21) Appl. No.: 12/226,683

(22) PCT Filed: Apr. 25, 2007

(86) PCT No.: PCT/JP2007/058912

§ 371 (c)(1),
(2), (4) Date: Mar. 9, 2010

(87) PCT Pub. No.: WO2007/125938

PCT Pub. Date: Nov. 8, 2007

(65) Prior Publication Data

US 2010/0282956 A1    Nov. 11, 2010

(30) Foreign Application Priority Data

Apr. 27, 2006  (JP) .................................. 2006-123014

(51) Int. Cl.
*G06F 19/00*  (2011.01)
*G01D 18/00*  (2006.01)
(52) U.S. Cl. ........................................ 702/95; 250/252.1
(58) Field of Classification Search .................... 702/95; 250/252.1; 355/72; 716/21; 356/237.6
See application file for complete search history.

(56) References Cited

U.S. PATENT DOCUMENTS

| 6,481,003 | B1* | 11/2002 | Maeda ............................. 430/22 |
| 6,876,946 | B2* | 4/2005 | Yasuda et al. .................. 702/152 |
| 2001/0054692 | A1 | 12/2001 | Nakada et al. |
| 2003/0062479 | A1* | 4/2003 | Kametani et al. ............. 250/310 |
| 2005/0002040 | A1 | 1/2005 | Adriaens et al. |

FOREIGN PATENT DOCUMENTS

| JP | 2000-100362 | 4/2000 |
| JP | 2001-203162 | 7/2001 |
| JP | 2001-338601 | 10/2001 |
| JP | 2004-343083 | 12/2004 |

OTHER PUBLICATIONS

International Search Report issued Jun. 12, 2007 in the International (PCT) Application of which the present application is the U.S. National Stage.

* cited by examiner

*Primary Examiner* — Bryan Bui
(74) *Attorney, Agent, or Firm* — Wenderoth, Lind & Ponack, L.L.P.

(57) ABSTRACT

Stage orthogonal error and position errors caused by mirror distortion are reduced. A CPU calculates a coordinate error ($\Delta x, \Delta y$) between a measured XY coordinate (x,y) of each of arbitrary reference points on a wafer $W_0$ loaded on a XY stage which is measured by a laser interferometer and a calculated ideal position XY coordinate of the reference point, calculates an orthogonal error of the XY coordinates on the bases of the calculated coordinate errors ($\Delta x, \Delta y$) and an error due to mirror distortion, and stores them in a storage device. When a wafer W is actually inspected, the CPU corrects the measured position coordinates (x,y) from the laser interferometer on the basis of the calculated orthogonal error, and corrects beam deflector for deflection on the basis of the calculated error due to mirror distortion.

17 Claims, 28 Drawing Sheets

Fig. 18
(A) 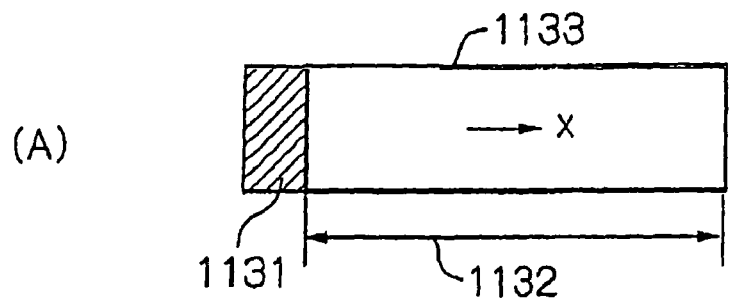
(B) 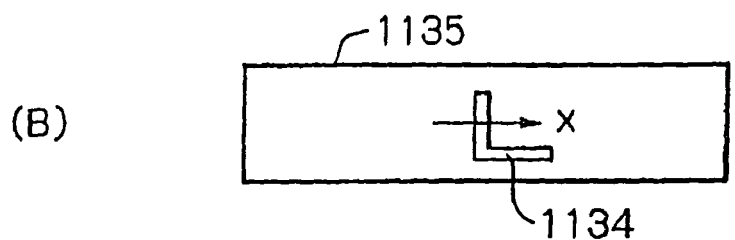
(C) 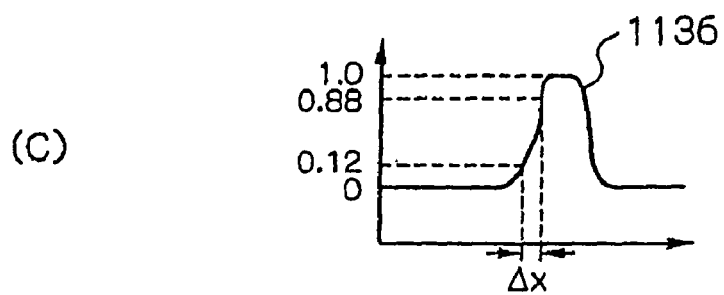
(D) 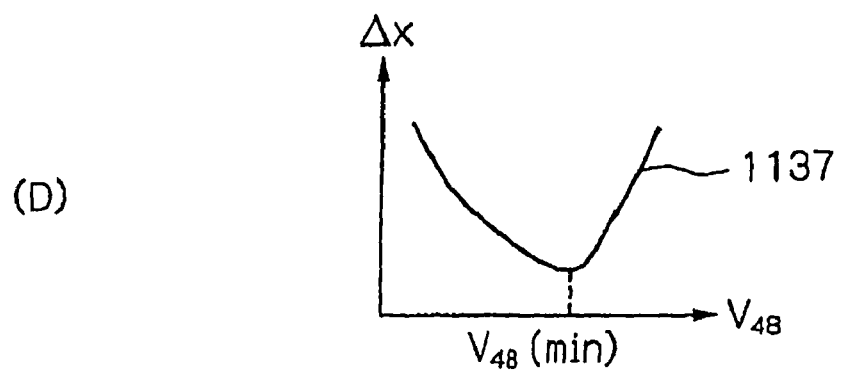

DIE MAP DIAGRAM

INSPECTION AREA INSIDE OF A DIE SETTING DIAGRAM

1162

1161

16 dots

OPERATION A
(A)

OPERATION B
(B)

$$\frac{\overset{t_1}{\sqcap}+\overset{t_2}{\sqcap}+\overset{t_3}{\sqcap}}{3} = \sqcap \text{ REFERENCE IMAGE}$$

Fig.35
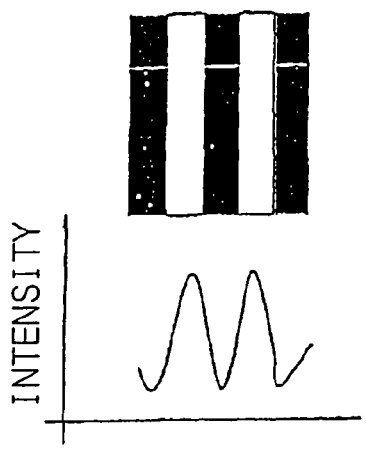
Fig.36
DIRECTION OF SCANNING Y →
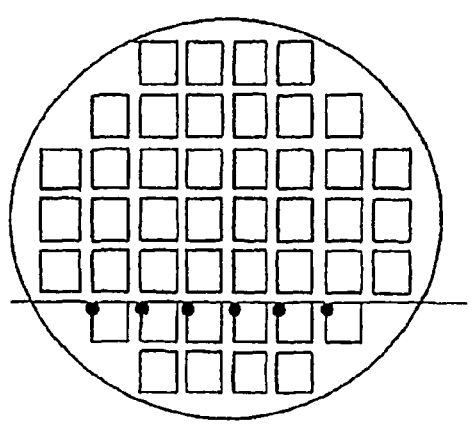
(A)
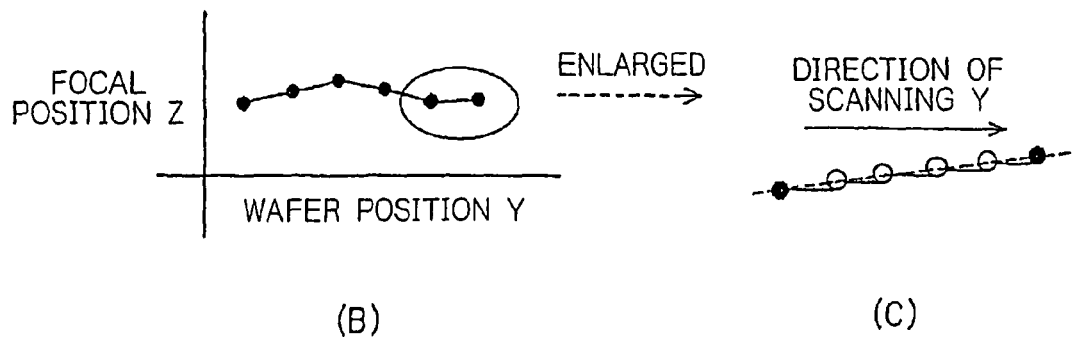
(B)         (C)

XY-COORDINATE COMPENSATION APPARATUS AND METHOD IN SAMPLE PATTERN INSPECTION APPARATUS

TECHNICAL FIELD

The present invention relates to a sample pattern inspection apparatus and method, and in particular, XY coordinate compensation apparatus and method for compensating a position error of a stage coordinate in an apparatus which uses an electron beam(s) to detect a defect(s) or the like of a device pattern with a minimum line width of 0.1 µm or less on a surface of a sample such as a stencil mask or wafer, to realize high accuracy and high reliability detection.

BACKGROUND ART

A sample pattern inspection apparatus is adapted to illuminate an electron beam(s) on a sample to be inspected such as a wafer to generate electrons having information relating to a device pattern formed on the sample surface, make an image of the device pattern from the generated electrons, and inspect the obtained image on the basis of a predetermined inspection program. High accurate information of the devise pattern of the sample surface is necessary to increase reliability of the inspection result.

However, such a sample pattern inspection apparatus according to a prior art has the following problems.

A stage for loading a sample and moving in X- and Y-directions which are orthogonal to each other, has stage guides for guiding the stage in the X- and Y-directions, respectively. Since the stage guides sometimes have distortion and are not accurately orthogonal to each other, the stage cannot always move through ideal moving paths. Further, a moving velocity of the stage is not always constant during continuous moving. In addition, when a sample is loaded on the stage, the XY coordinate of the sample does not always coincide with the XY coordinate of the stage, resulting in that an error in a rotational direction occurs. In such a case, dies are fabricated on positions which are different from designed positions, during a lithography procedure.

According to the above problems, the sample pattern inspection apparatus cannot always provide accurate results.

When the position errors as above are not compensated, an obtained image may be shifted from an ideal position by ±2 pixels or more, for instance. If the image is shifted from the ideal position by ±2 pixels in both X- and Y-directions, 49 (=7×7) image pieces for comparison are required to ensure accuracy of the inspection result. Therefore, since it is necessary to increase the number of memories and comparison circuits which are provided for inspection, a defect inspection speed is lower than an image capturing speed and hence defect inspection with a high throughput cannot be carried out.

The applicant of the subject application has provided a sample defect inspection apparatus as described in the following patent application official gazette. To inspect patterns of dies which are digestedly arranged on the X-Y plane of the sample, the inspection apparatus is adapted to generate a grid with constant intervals along the X- and Y-axes of an ideal X-Y coordinate on which dies are virtually arranged; obtain actual position coordinate of the respective dies; calculate position errors or displacements between the position of the constant interval grid and the actual position; and compensate the position coordinates of the respective dies on the basis of the position errors so that the dies are arranged along the constant interval grid.

In the compensation of the position coordinate, a compensation XY map is prepared in which the position errors obtained correspondingly to the position coordinates of the constant interval grid, are stored, and in response to a position error stored in the compensation XY map, a voltage which is applied to a compensation electrode located at a front stage of a MCP for instance, is adjusted, so that the electron beam is polarized to match a die position on the wafer to an image position on the MCP.

Prior Art Document 1:

Japanese Patent Application Public Disclosure No. 2000-91342

However, in some cases, the compensation (in the prior art document that the voltage to be supplied to the compensation electrode, is adjusted in response to the position error information in the compensation XY map) is not satisfactory. For instance, in general, static compensation of ±20 µm or more is required, while a polarization dynamic range by a compensation electrode is around ±20 µm, which may not cover the required range.

Further, in the prior compensation, positions of a plurality of points on a wafer are measured, and position errors of the points are obtained, while position errors of points other than the measured points are obtained using an interpolation method. However, the position measurements of the points are not always accurate. Therefore, if a position error of a measured point is abnormal, the results of the interpolation are irrelevant because of the abnormal position error.

The invention has been made in view of the above problems. It is an object of the invention to provide an electron beam apparatus for inspecting sample patterns, which is capable of reducing problems which are caused by stage guide distortion, orthogonal errors of the stage guide and so on, and inspecting with a high accurate and high throughput even if a stage is not located at a predetermined position, dies on a wafer are not located in line with theoretical ideal coordinate and/or a moving speed is not constant.

SUMMARY OF THE INVENTION

To achieve the above object, the present invention provides an electron beam apparatus for inspecting a pattern on a sample using an electron beam which comprises:

first processing means for calculating a coordinate error ($\Delta x, \Delta y$) of a measured XY coordinate (x,y) of each of arbitrary reference points on the sample from a calculated ideal position XY coordinate of the reference point;

second processing means for calculating an orthogonal error of the XY coordinates based on the calculated coordinate errors;

third processing means for calculating an error due to mirror distortion of an interferometer of the electron beam apparatus on the basis of the calculated coordinate errors;

orthogonal error correcting means for compensating the measured XY coordinates (x,y) on the basis of the calculated orthogonal error upon inspecting the sample; and beam deflection correcting means for compensating deflection by a beam deflector disposed in a second electro-optical system on the basis of the calculated mirror distortion error upon inspecting the sample.

In the electron beam apparatus, it is preferable that the second and third processing means comprise recursive processing means for obtaining coefficients $a_1 \sim e_1$ and $a_2$~$e_2$ which satisfy the following Equations (1) and (2), through recursive processing:

$$\Delta x = a_1 + b_1 x + c_1 y + d_1 x^2 + e_1 y^2 \quad (1)$$

$$\Delta y = a_2 + b_2 x + c_2 y + d_2 x^2 + e_2 y^2 \quad (2)$$

the second processing means further comprises means for calculating the orthogonal error of the XY coordinate system as a difference between the obtained coefficients c1 and b2; and the third processing means further comprises means for calculating the coordinate error ($\Delta x, \Delta y$) as the mirror distortion error, by substituting a XY coordinate (x,y) provided from the interferometer upon driving the electron beam apparatus, into equations which are derived by substituting the obtained coefficients $d_1$, $d_2$, $e_1$ and $e_2$ into the following Equations (3) and (4):

$$\Delta x = d_1 x^2 + e_1 y^2 \quad (3)$$

$$\Delta y = d_2 x^2 + e_2 y^2 \quad (4)$$

The third processing means may comprise; recursive processing means for obtaining coefficients $a_1$~$e_1$ and $a_2$~$e_2$ which satisfy Equations (1) and (2) through recursive processing, on the basis of the coordinate error ($\Delta x, \Delta y$) obtained by the first processing means after the orthogonal error has been corrected by the orthogonal error correcting means; and means for calculating the coordinate error ($\Delta x, \Delta y$) as the mirror distortion error, by substituting a XY coordinate (x,y) provided from the interferometer upon driving the electron beam apparatus, into equations which are derived by substituting the obtained coefficients $a_1$~$e_1$ and $a_2$~$e_2$ into Equations (1) and (2).

In the above electron beam apparatus, it is preferable that: the second processing means comprises:

recursive processing means for obtaining coefficients $a_1$~$c_1$ and $a_2$~$c_2$ which satisfy the following Equations (5) and (6), through recursive processing:

$$\Delta x = a_1 + b_1 x + c_1 y \quad (5)$$

$$\Delta y = a_2 + b_2 x + c_2 y \quad (6), \text{ and}$$

means for calculating the orthogonal error of the XY coordinate system as a difference between the obtained coefficients c1 and b2; and the third processing means comprises:

recursive processing means for obtaining coefficients $d_1$, $e_1$, $d_2$ and $e_2$ which satisfy the following Equations (3) and (4), through recursive processing:

$$\Delta x = d_1 x^2 + e_1 y^2 \quad (3)$$

$$\Delta y = d_2 x^2 + e_2 y^2 \quad (4), \text{ and}$$

means for calculating the coordinate error ($\Delta x, \Delta y$) as the mirror distortion error, by substituting a XY coordinate (x,y) provided from the interferometer upon driving the electron beam apparatus, into equations which are derived by substituting the obtained coefficients $d_1$, $e_1$, $d_2$ and $e_2$ into Equations (3) and (4).

The third processing means may comprise:

recursive processing means for obtaining coefficients $a_1$~$e_1$ and $a_2$~$e_2$ which satisfy the following Equations (1) and (2), through recursive processing, on the basis of the coordinate error ($\Delta x, \Delta y$) obtained by the first processing means after the orthogonal error has been corrected by the orthogonal error correcting means:

$$\Delta x = a_1 + b_1 x + c_1 y + d_1 x^2 + e_1 y^2 \quad (1)$$

$$\Delta y = a_2 + b_2 x + c_2 y + d_2 x^2 + e_2 y^2 \quad (2), \text{ and}$$

means for calculating the coordinate error ($\Delta x, \Delta y$) as the mirror distortion error, by substituting a XY coordinate (x,y) provided from the interferometer upon driving the electron beam apparatus, into equations which are derived by substituting the obtained coefficients $a_1$~$e_1$ and $a_2$~$e_2$ into Equations (1) and (2).

The electron beam apparatus of the invention may further comprises: means for compensating shift amounts in the X-axis direction and Y-axis direction by the coefficients $a_1$ and $a_2$ obtained by the recursive processing means; and means for compensating scale errors in the X-axis direction and Y-axis direction by the coefficients $b_1$ and $c_2$ obtained by the recursive processing means.

It is preferable that the beam deflector comprises a deflection electrode; and the beam deflection compensation means is adapted to adjust a voltage to the deflection electrode. In addition, it is preferable that the electron beam apparatus of the invention further comprises: means for detecting a secondary electron beam emitted from the sample by the irradiation of a primary electron beam; means for capturing image information on the pattern on the sample surface on the basis of the output of the detecting means; and means for detecting a defect of the pattern by comparing the captured image information with image information on the same pattern at different positions on the same sample, or with image information on a reference pattern previously stored for comparison.

The present invention further provides a method of compensating an error regarding a stage position in an electron beam apparatus for inspecting a pattern on a sample using an electron beam, and a computer program read and executed by a computer to execute the stage position error correcting method.

BRIEF DESCRIPTION OF THE DRAWINGS

FIGS. 12A-12C are diagrams illustrating vectors of errors, in which FIG. 12A is associated with a case that no compensation is executed, FIG. 12B is associated with the case that only Level 1 compensation is executed, and FIG. 12C is associated with a case that Level 2 compensation is executed;

FIGS. 15A-15C are diagrams in which FIG. 15A illustrates a fourth embodiment of an electron beam apparatus using a multi-beam system with multi optical axes, FIG. 15B illustrates a plan view of amplification lenses of the embodiment, and FIG. 15C illustrates a plan view of anodes of the embodiment;

FIGS. 18A-18D are diagrams for explaining operations of the electron beam apparatus in FIG. 17;

FIG. 35 shows diagrams for explaining a focus mapping in an inspection procedure in a semiconductor device manufacturing method;

FIGS. 36A-36C show diagrams for explaining a focus mapping in an inspection procedure in a semiconductor device manufacturing method.

DETAILED DESCRIPTION OF THE INVENTION

Before describing preferred embodiments of a sample pattern inspection apparatus and inspection method according to the present invention, description will be made on the whole inspection system for inspecting a substrate or wafer on which patterns are fabricated, with reference to FIGS. 1-5. In the inspection system, the sample pattern inspection method is carried on.

Figure 1:
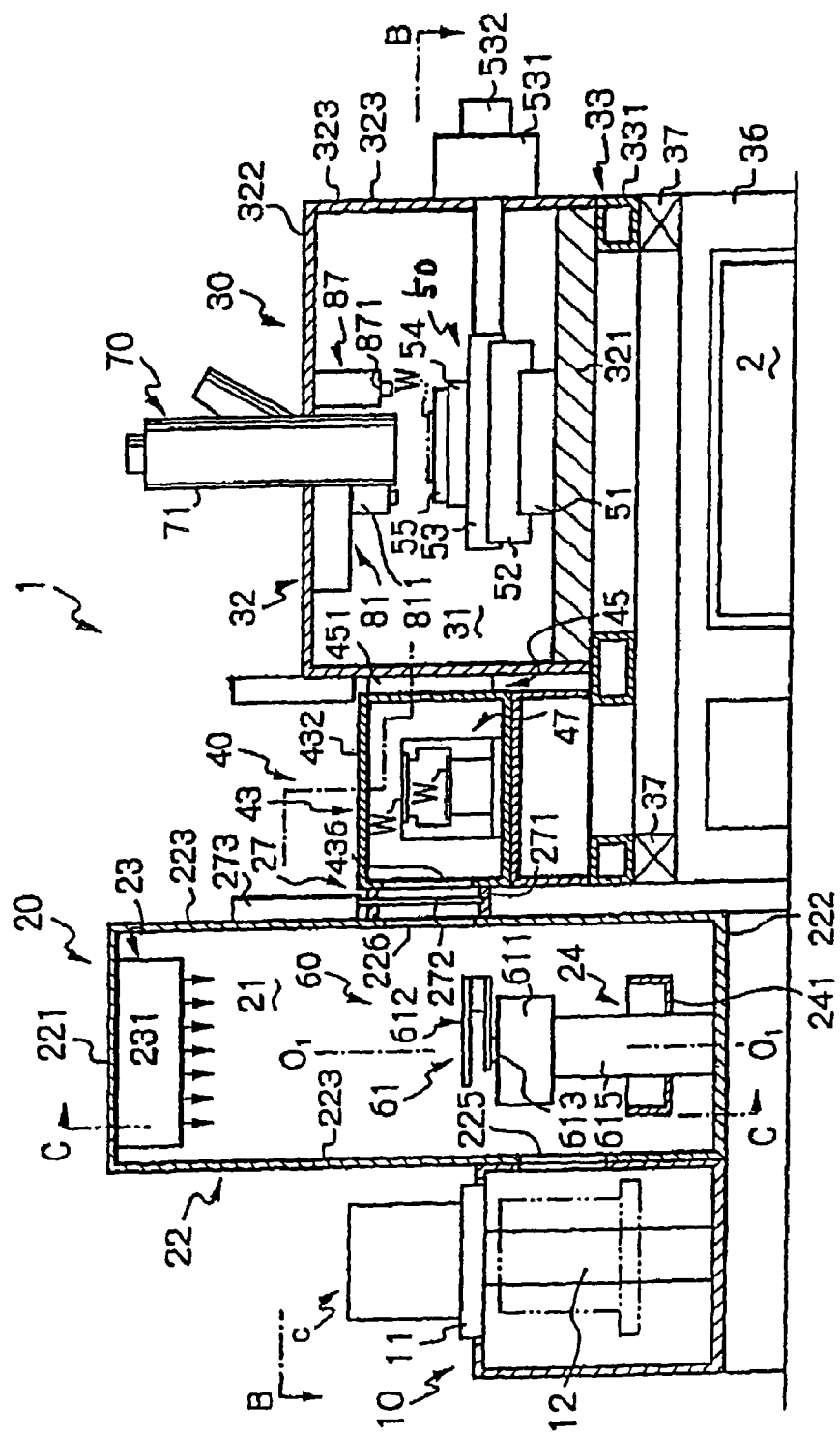
FIG. 1 is an elevation view illustrating major components of a sample inspection system.
Figure 2:
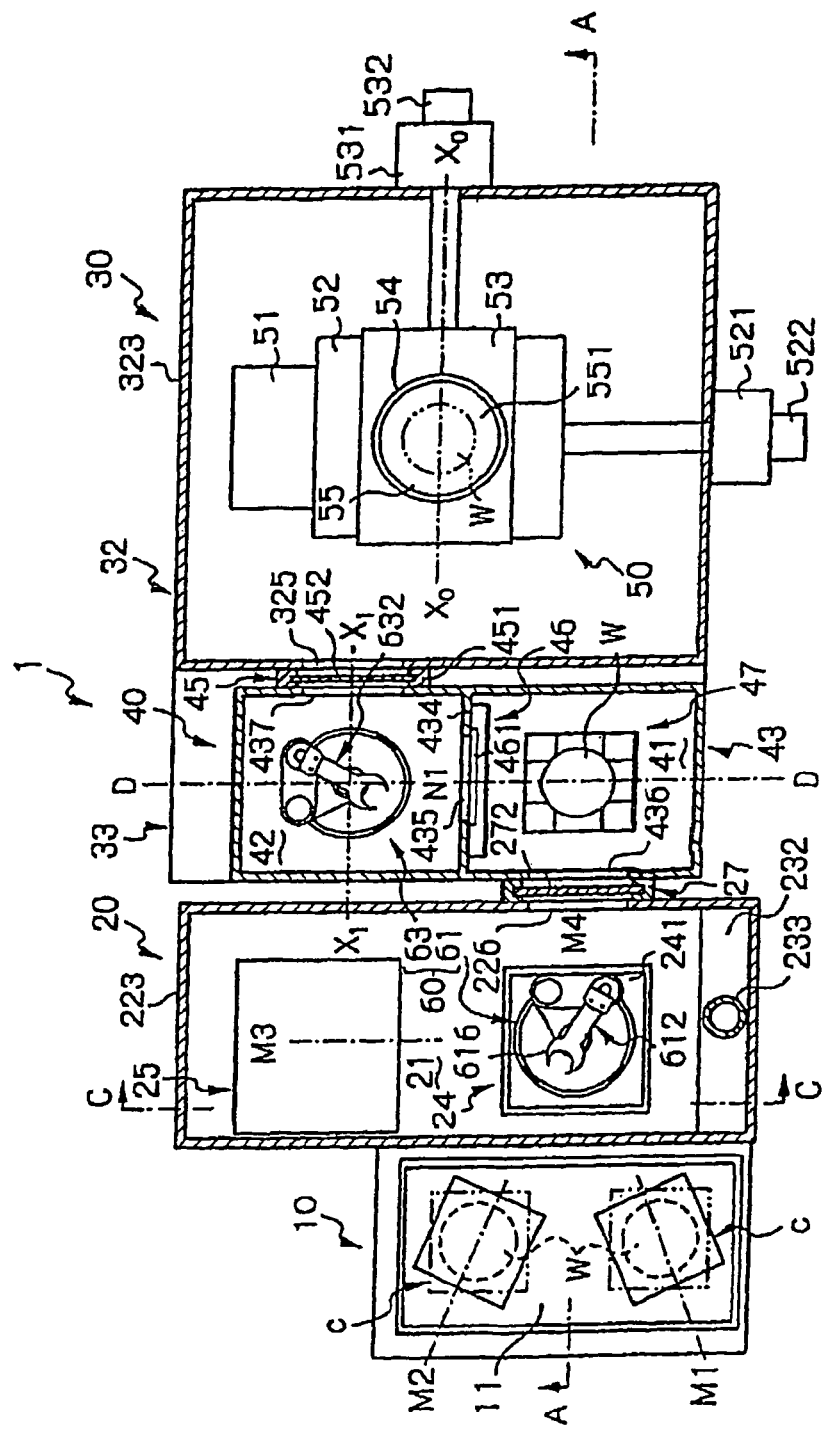
FIG. 2 is a plan view illustrating major components of the sample inspection system.

As illustrated in FIGS. 1 and 2, the inspection system 1 comprises the following main components:
a cassette holder 10 for holding a cassette containing a plurality of wafers "W";
a mini-environment unit 20;
a main housing 30 defining a working chamber 31;
a loader housing 40 located between the mini-environment unit 20 and the main housing 30 and defining two loading chambers;
a loader 60 for picking up the wafer W from the cassette holder 10 and loading it on a stage device 50 located within the main housing 30; and
an electron optical device 70 in a vacuum housing.

All of these components are arranged in such a physical relationship as depicted in FIGS. 1 and 2.

The inspection system 1 further comprises a pre-charging unit 81 located within the main chamber 30 which is under a vacuum condition; a potential application mechanism 83 for applying a potential to the wafer W (see FIG. 5); an electron beam calibration mechanism 87 (see FIG. 8); and an optical microscope 871 constituting an alignment controller for positioning the wafer W on the stage device 50.

The cassette holder 10 is designed to hold a plurality (two pieces in this embodiment) of cassettes "c" (e.g., a closed cassette, such as FOUP manufactured by Assist Inc.), each containing a plurality (e.g., 25 pieces) of wafers W placed side by side in parallel with each other along the up and down direction. This cassette holder 10 may employ a suitable structure depending on the specific cases selectively such that for a case where the cassette is transferred by a robot or the like and loaded onto the cassette holder 10 automatically, a specific suitable structure therefore may be employed and that for a case where the loading operation is manually loaded, an open cassette structure suitable for such manually loading may be employed.

In this embodiment, the cassette holder 10 has a system for automatically loading the cassette c, and comprises, for example, an lifting table 11 and an lifting mechanism 12 for moving up and down the lifting table 11, wherein the cassette c is set on the lifting table 11 automatically in a state illustrated by the chain line in FIG. 2, and after having been set, the cassette c is rotated automatically into an orientation illustrated by the solid line in FIG. 2 for heading to an axial line of rotational movement of a first transport unit (as will be described later) within the mini-environment unit 20, and then the lifting table 11 is lowered down to the position indicated by the chain line in FIG. 1. The cassette holder used in the case of the automatic loading or the cassette holder used in the case of the manual loading may appropriately employ any known structures, and detailed description of its structure and function should be herein omitted.

The wafers W contained in the cassette c are those subject to the inspection, and such an inspection may be carried out after or in the course of a process for processing the wafer in the series of processes for manufacturing the semiconductor. Specifically, those wafers that have experienced the film-depositing step, the CMP step, the ion implantation step and the like, or those wafers that have been or have not been patterned on the surfaces thereof may be accommodated in the cassette. A plurality of those wafers W are accommodated in the cassette c so as to be spaced in parallel with each other along the up and down direction. For this reason, an arm of the first transport unit (as will be described later) is adapted to move up and down so that the wafer W in a desired position can be held by the first transport unit.

Figure 3:
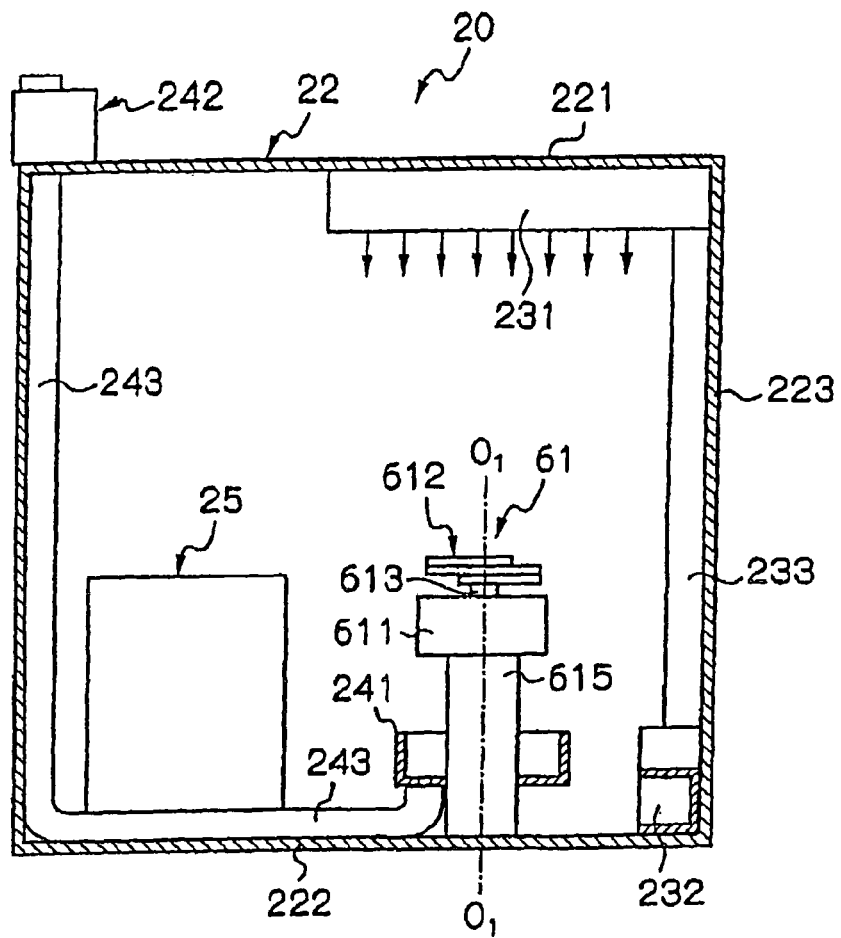
FIG. 3 illustrates a mini environment device of the sample inspection system.

In FIGS. 1-3, the mini-environment unit 20 comprises: a housing 22 defining a mini-environment space 21 of which atmosphere may be controlled; a gas circulator 23 for providing the atmosphere control by circulating a gas such as a clean air within the mini-environment space 21; an exhausting device 24 for recovering and then exhausting a portion of the air supplied into the mini-environment space 21; and a pre-aligner 25 arranged within the mini-environment space 21 for providing a coarse alignment of the wafer W subject to the inspection.

The housing 22 comprises a top wall 221, a bottom wall 222 and circumferential walls 223 surrounding four circumferential portions so as to provide a structure to separate the mini-environment space 21 from an external environment. In order to provide the atmosphere control of the mini-environment space 21, the gas circulator 23 comprises, as shown in FIG. 3, a gas supply unit 231 which is attached to the top wall 221 within the mini-environment space 21 for cleaning the air and then directing a laminar flow of thus cleaned air right below through one or more gas blow-off openings (not shown); a recovery duct 232 located on the bottom wall 222 within the mini-environment space 21 for recovering the air that has flown down toward the bottom; and a conduit 233 interconnecting the recovery duct 232 and the gas supply unit 231 for returning the recovered air back to the gas supply unit 231.

The laminar flow of the clean air directed downward, or the down flow, is supplied such that it can flow mainly through a conveying surface of the first transport unit 61 located within the mini-environment space 21 to thereby prevent any dust which could be produced by the transport unit 61 from adhering to the wafer W. An access port 225 is formed in a location of the circumferential wall 223 of the housing 22 adjacent to the cassette holder 10.

As shown in FIG. 3, the exhausting device 24 comprises: a suction duct 241 disposed in a location lower than the wafer conveying surface of said transport unit 61 and in the lower portion of the transport unit; a blower 242 disposed external to the housing 22; and a conduit 243 for interconnecting the suction duct 241 and the blower 242. This exhausting device 24 sucks the gas flowing down along the circumference of the transport unit and containing the dust which could be produced by the transport unit, through the suction duct 241, and exhausts that air to the outside of the housing 22 via the conduits 243 and the blower 242.

The pre-aligner 25 disposed within the mini-environment space 21 is designed to detect optically or mechanically an orientation-flat formed in the wafer W (referred to a flat portion formed in an outer periphery of a circular wafer) or one or more V-shaped cut-out or notch formed in an outer peripheral edge of the wafer W, and to provide in advance an alignment of the wafer W in the rotational direction around the axis line $O_1$-$O_1$ of the transfer unit 61 within an accuracy of ±1 degree. The pre-aligner 25 is a constitutional part of a mechanism for determining a coordinate of a subject to be inspected, and takes a role in providing a coarse alignment of the subject to be inspected. Since the pre-aligner 25 may be of any known structure, description of its structure and function should be omitted.

In FIG. 1 and FIG. 2, the main housing 30 defining the working chamber 31 comprises a housing main body 32. The housing main body 32 is supported by a housing supporting device 33 loaded on a vibration insulating device or a vibration isolating device 37 located on a table frame 36 and the housing supporting device 33 comprises a frame structure 331 assembled into a rectangular shape. Thus, the housing main body 32 is disposed and mounted securely onto the frame structure 331. The housing main body 32 comprises a bottom wall 321 loaded on the frame structure 331, a top wall 322 and circumferential walls 323 connected to both of the bottom wall 321 and the top wall 322 to surround four circumferential portions, thereby isolating the working chamber 31 from the outside.

The housing main body 32 and the housing supporting device 33 is assembled in a rigid structure, wherein the vibration isolating device 37 prevents the vibration from the floor on which the table frame 36 is installed from being transmitted to this rigid structure. An access port 325 for taking in and out the wafer is formed in one circumferential wall among those circumferential walls 323 of the housing main body 32, which is adjacent to a loader housing 40.

The working chamber 31 is designed to be held in a vacuum atmosphere by a vacuum device (not shown) having a known structure. A controller 2 for controlling an overall operation of the apparatus is located under the table frame 36. The working chamber 31 is typically held under a pressure in a range of $10^{-4}$ to $10^{-6}$ Pa.

Figure 4:
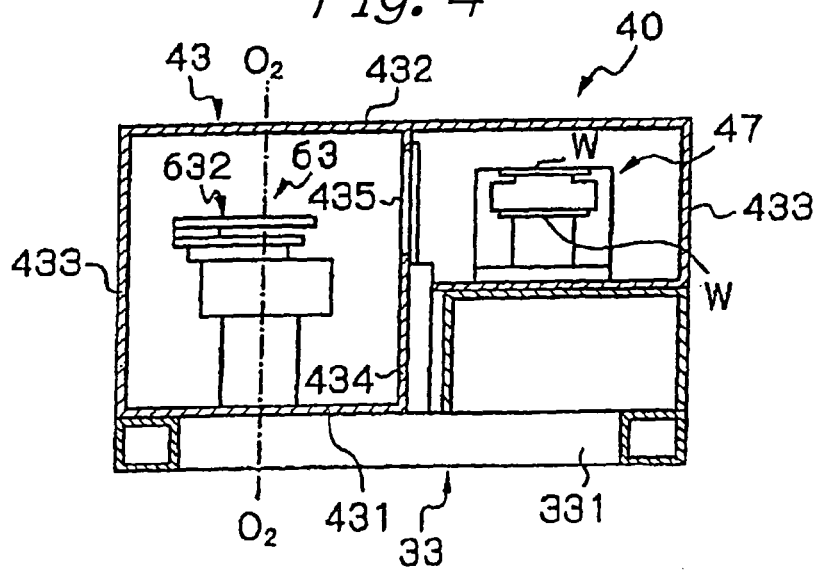
FIG. 4 illustrates a loader housing of the sample inspection system.

Referring to FIGS. 1, 2 and 4, the loader housing 40 comprises a housing main body 43 defining a first loading chamber 41 and a second loading chamber 42. The housing main body 43 comprises a bottom wall 431, a top wall 432, circumferential walls 433 surrounding four circumferential portions and a partition wall 434 for separating the first loading chamber 41 and the second loading chamber 42, so that both loading chambers 41 and 42 may be isolated from the external environment. An access port 435 is formed in the partition wall 434 for passing the wafer W between two loading chambers 41 and 42. Further, access ports 436 and 437 are formed in locations of the circumferential walls 433 adjacent to the mini-environment unit 20 and the main housing 30, respectively.

As shown in FIG. 4, since the housing main body 43 of this loader housing 40 is mounted on and supported by the frame structure 331 of the housing supporting device 33, this loader housing 40 is also designed to be protected from any vibrations otherwise transmitted from the floor. The access port 436 of the loader housing 40 and the access port 226 of the housing 22 of the mini-environment unit 20 are aligned and interconnected with each other, and in a connecting point therebetween a shutter system 27 is arranged so as to selectively block the communication between the mini-environment space 21 and the first loading chamber 41.

The access port 437 of the loader housing 40 and the access port 325 of the housing main body 32 are aligned and interconnected with each other, and in a connecting point therebetween a shutter system 45 is arranged so as to selectively seal and block the communication between the second loading chamber 42 and the working chamber 31. Further, the opening 435 formed in the partition wall 434 is provided with a shutter system 46 which selectively blocks the communication between the first and the second loading chambers 41 and 42 by closing or opening a door 461. Those shutter systems 27, 45 and 46 are designed to provide an airtight sealing to each loading chamber when they are in closed positions.

In the first loading chamber 41, a wafer rack 47 is arranged, which holds a plurality, for example two pieces, of wafers W in a horizontal state to be spaced from each other in the up and down direction. The first and the second loading chambers 41 and 42 are adapted to have the atmosphere controlled to be high vacuum condition (in a range of $10^{-5}$ to $10^{-6}$ Pa as a vacuum level) by the aid of a well-known vacuum exhausting device (not shown) including vacuum pump, though not shown. In that case, the first loading chamber 41 may be held in a lower vacuum atmosphere as a low vacuum chamber, while the second loading chamber 42 may be held in a higher vacuum atmosphere as a high vacuum chamber, thereby providing an effective way to prevent the contamination of the wafer W. Employing such a configuration not only can help transfer the subsequent wafer W that is accommodated in the loading chamber and is to be subjected to a defect inspection into the working chamber 31 without delay, but also can help improve the throughput of the defect inspection and further help maintain the vacuum level in the surrounding of the electron beam source, which is required to be held in a high vacuum condition, at as high vacuum conditions as possible.

The first and the second loading chambers 41 and 42 are connected with a vacuum exhausting pipe (not shown) and a vent pipe (not shown) for an inactive gas (e.g., purified dry nitrogen), respectively. With this arrangement, injecting the inactive gas into each loading chamber can prevent an oxygen gas and the like other than the inactive gas from adhering to the surface of each chamber with the aid of the inactive gas vent.

It is to be noted that in a sample inspection apparatus using an electron beam according to the present invention, it is important that a substance represented by lanthanum hexaboride ($LaB_6$) that can be used as an electron beam source of an electron optical device should not be brought into contact with oxygen as much as possible after it is heated up to such a high temperature where the thermal electron is emitted therefrom in order not to reduce a lifetime thereof. As it is, this can be ensured by applying the atmosphere control as described above to the working chamber 31 in which the electron optical device is installed, in a step prior to a transfer operation of the wafer W thereinto.

The stage device 50 comprises: a stationary table 51 located on the bottom wall 321 of the main housing 30; a Y table 52 operatively mounted on the stationary table 51 to be capable of moving in the Y direction (the direction orthogonal to the sheet surface in FIG. 1); an X table 53 operatively mounted on the stationary table 51 to be capable of moving in the X direction (the left and right direction in FIG. 1); a turntable 54 capable of rotating on the X table 53; and a holder 55 located on the turntable 54. The wafer W is releasably loaded on a wafer loading surface 551 of the holder 55. The holder 55 may have a known structure allowing for the wafer W to be releasably gripped in a mechanical manner or by an electrostatic chuck system.

The stage device 50 is adapted to provide a highly precise alignment of the wafer W held in the holder 55 on the loading surface 551 with respect to the electron beam irradiated from the electron optical device in the X direction, Y direction and Z direction (i.e., the up and down direction in FIG. 1) as well as in the rotational direction around the axial line orthogonal to the supporting surface of the wafer W (i.e., in the θ direction), by actuating the plurality of tables 51 to 54 described above using a servo motor, an encoder and a variety of sensors (not shown).

It is to be noted that the positioning of the wafer W in the Z direction may be achieved by, for example, making the position of the loading surface 551 on the holder 55 to be fine-tunable. In these operations, a reference position of the loading surface 551 is detected by a position measuring device employing laser having very fine diameter (laser interference range finder using a principle of interferometer) and said position is controlled by a feedback circuit (not shown) and in association with or instead of the above control, the position of the notch or the orientation-flat of the wafer is measured to detect a position within a plane and a rotational position of the wafer with respect to the electron beam, and the turntable is rotated by, for example, a stepping motor capable of fine angle controlling so as to control the position of the wafer. In order to prevent or minimize, any production of dust within the working chamber 31, the servo motors 521 and 531 and the encoders 522 and 532 for the stage device 50 are disposed external to the main housing 30. It is to be noted that the reference can be set for the signal obtained by inputting in advance the rotational position and/or the position in the X- and the Y-directions of the wafer W with respect to the electron beam to a signal detecting system or an image processing system, both of which will be described later.

The loader 60 comprises a first transport unit 61 of a robot system located within the housing 22 of the mini-environment unit 20 and a second transport unit 63 of a robot system located within the second loading chamber 42. The first transport unit 61 has a multi-joint arm 612 capable of rotating around an axial line $O_1$-$O_1$ with respect to a driving section 611. The multi-joint arm may employ any arbitrary structure, and in the illustrated embodiment, the arm 612 includes three parts operatively joined so as to be movable rotationally with respect to each other. A first part of the arm 612 of the first transport unit 61, which is one of the three parts located in the closest position to the driving section 611, is attached to a shaft 613 which may be driven to rotate by a driving mechanism of known structure (not shown) arranged in the driving section 611. The arm 612 can rotate around the axial line $O_1$-$O_1$ with the aid of the shaft 613, while it can be extended or contracted in the radial direction with respect to the axial line $O_1$-$O_1$ as a whole unit by a relative rotation among the parts. A tip portion of a third part of the arm 612, which is one of those parts located in the uppermost position, is provided with a gripping device 616 for gripping the wafer W, which is implemented by a mechanical, electrostatic or other type chuck of known structure. The driving section 611 is allowed to move in the up and down direction by an lifting mechanism 615.

In operation, the arm 612 of the first transport unit 61 is extended toward either one of the directions for M1 and for M2 between those for two cassettes c held in the cassette holder, and one piece of wafer W accommodated in the cassette c is placed onto the arm or gripped by the chuck (not shown) attached to the tip portion of the arm 612, so as to be taken out of it. After that, the arm 612 is contracted into the state shown in FIG. 2, and then is rotated to and stopped at a position from which it can be extended toward the direction M3 for the pre-aligner 25. As it is, the arm is again extended so as to place the wafer W held by the arm 612 onto the pre-aligner 25. The arm 612, after the pre-aligner 25 having applied a fine-tuning of the orientation of the wafer W, receives the wafer W from the pre-aligner 25 and then the arm 612 is further rotated to and stopped at a position in which the arm is allowed to be extended toward the first loading chamber 41 in the direction M4, where it is extended so as to hand over the wafer W to a wafer receiver 47 within the first loading chamber 41.

It is to be noted that in a case of gripping the wafer W mechanically, preferably a circumferential edge region defined by a range within about 5 mm from the circumferential edge of the wafer W should be gripped. This is because the wafer W is in its inner surface entirely patterned with devices such as circuit wirings only excluding the circumferential edge region, and accordingly gripping of the wafer W in that patterned region could cause a breakage of the device and a defect therein.

The second transport unit 63 has basically the same structure as the first transport unit 61, but it is operable so that the transfer operation of the wafer W is performed between the wafer rack 47 and the loading surface 551 of the stage device 50.

In the loader 60, the first and the second transport units 61 and 63 carry out the transfer operation of the wafer W as it is held in the horizontal state from the cassette c held by the cassette holder 10 onto the stage device 50 located within the working chamber 31 and vice versa. The up and down motions of the arms 612 and 632 of the transport units 61 and 63 are limited only to the steps where the wafer W is taken out of or inserted into the cassette c, where the wafer W is placed on or taken out of the wafer rack 47, and where the wafer W is placed on or taken out of the stage device 50. Therefore, even the transfer of such a large wafer W having a 30 cm diameter, for example, can be carried out smoothly.

The transfer operations of the wafer W from the cassette c carried by the cassette holder 10 onto the stage device 50 located in the working chamber 31 will now be described in order with reference to FIGS. 1 through 4. As for the cassette holder 10, a suitable structure may be selectively employed therefore, as already set forth, depending on particular cases, including one for the manual setting of the cassette and another for the automatic setting of the cassette. Once the cassette c is set on the lifting table 11 of the cassette holder 10, the lifting table 11 is lowered by the lifting mechanism 12 and the cassette c is aligned with the access port 225.

When the cassette c is aligned with the access port 225, the cover (not shown) arranged in the cassette c is opened, and at the same time, a cylindrical cover is disposed between the cassette c and the access port 225 so as to block the interior of the cassette c and the space inside of the mini-environment unit 21 from the external environment. It is to be noted that in the case where the shutter system for opening and closing the access port 225 is arranged in the mini-environment unit 20, that shutter system should be actuated to open and close the access port 225.

The arm 612 of the first transport unit 61 has been stopped as it is oriented to either of the direction M1 or M2. Assuming that it has stopped as oriented to the direction of M1, when the access port 225 is opened, the arm 612 is extended through the access port 225 to receive one of the wafers W accommodated in the cassette c by its tip portion. Once the receiving operation of the wafer W by the arm 612 is completed, the arm 612 is contracted and, if said shutter system is installed, said shutter system is actuated to close the access port 225. Then, the arm 612 is rotated around the axial line $O_1$-$O_1$ and stopped in a position allowing for the arm 612 to be extended toward the direction M3, where the arm 612 is extended and places the wafer W loaded on its tip portion or gripped by the chuck onto the pre-aligner 25, which in turn determines the orientation of the rotational direction of the wafer W, or the direction around the central axis line orthogonal to the wafer plane, to be set within a specified range.

Once the alignment operation has been completed, the first transport unit 61, after having received the wafer W from the pre-aligner 25 onto the tip portion of the arm 612, contracts its arm 612 and takes a posture ready to extend the arm 612 toward the direction M4. Then, the door 272 of the shutter system 27 is moved to open the access ports 226 and 436, so that the arm 612 is extended into the first loading chamber 42 and loads the wafer W into the upper step side or the lower step side of the wafer rack 47. It is to be noted that, as described above, before the shutter system 27 goes into the open position to allow the wafer W to be transferred to the wafer rack 47, the opening 435 defined in the partition wall 434 would have been closed to be airtight by the door 461 of the shutter system 46.

In the course of transfer operation of the wafer W by the first transport unit 61, clean air flows down in a laminar flow as the down flow from the gas supply unit 231 arranged in the upper side of the housing 22 of the mini-environment unit 20 so as to prevent the dust from adhering to the top surface of the wafer W during its transfer operation. A portion of the air in the surrounding of the transport unit 61 is sucked through the suction duct 241 of the exhausting device 24 and exhausted to the outside of the housing. This is because a portion of the air supplied from the supply unit 231, for example, about 20% thereof, is mainly contaminated air. The remaining portion of the air is recovered via the recovery duct 232 disposed in the bottom of the housing 22 and returned back to the gas supply unit 231.

Once the wafer W has been loaded in the wafer rack 47 within the first loading chamber 41 by the first transport unit 61, the shutter system 27 is actuated into the closed position to close the loading chamber 41. Subsequently, the first loading chamber 41 is filled with an inactive gas to purge the air, and after that said inactive gas is also exhausted to bring the interior of the loading chamber 41 into the vacuum atmosphere. The vacuum atmosphere of the first loading chamber 41 may be set at a low vacuum level.

Once a certain degree of vacuum has been obtained in the loading chamber 41, the shutter system 46 is actuated to open the access port 435, which has been closed to be airtight by the door 461, and the arm 632 of the second transport unit 63 is then extended into the first loading chamber 41 and receives one piece of wafer W from the wafer receiver 47 by placing it on the tip portion of the arm 632 or by gripping it by the gripping device, such as a chuck, installed in the tip portion of the arm 632. After the receiving operation of the wafer W having been completed, the arm 632 is contracted, and the shutter system 46 is again actuated to close the access port 435 by the door 461.

It is to be noted that before the shutter system 46 is actuated into the open position, the arm 632 takes a posture ready to extend toward the direction N1 for the wafer rack 47, and further, the access ports 437 and 325 have been closed by the door 452 of the shutter system 45 to block the communication between the second loading chamber 42 and the working chamber 31 in the airtight condition. Once the access port 435 and the access ports 437 and 325 have been closed, the second loading chamber 42 is vacuum evacuated and ultimately brought into the vacuum at a higher vacuum level than that in the first loading chamber 42.

During this vacuum evacuation of the second loading chamber 42, the arm 632 of the second transport unit 63 is rotated to a position in which it is allowed to extend toward the stage device 50 in the working chamber 31. On one hand, in the stage device 50 within the working chamber 31, the Y table 52 is moved until the centerline $X_0$-$X_0$ of the X table 53 approximately comes into alignment with the X-axis line $X_1$-$X_1$ crossing the rotational axial line of the second transport unit 63, while at the same time the X table 53 is moved to a position closest to the loader housing 40 and stands by in this state. When the second loading chamber 42 has been brought into the approximately same level of vacuum condition as the working chamber 31, the door 452 of the shutter system 45 is actuated to open the access ports 437 and 325, and the arm 632 is extended into the working chamber 31, such that the tip portion of the arm 632 holding the wafer W comes near to the stage device 50 in the working chamber 31 and then places the wafer W on the loading surface 551 of the stage device 50. When the loading operation of the wafer W has been completed, the arm 632 is contracted, and the shutter system 45 closes the access ports 437 and 325.

The stage device 50 comprises a mechanism for applying an negative-bias potential (or a retarding potential) to the wafer W. This is a mechanism intended to avoid a failure such as discharging due to a short circuit by way of setting the arm 632 in a potential similar or proximal to the potential level of the stage device 50 or in a floating potential during the arm 632 going to the stage device 50 to pick up or to place the wafer W from or onto the stage device 50. It is to be noted that during transferring of the wafer W onto the stage device 50, the bias potential applied to the wafer W may be turned off.

In controlling of the bias potential, the potential may be turned off until the wafer is transferred to the stage and it may be turned on after the wafer has been transferred to and placed on the stage so as to apply the bias potential. The timing of the application of the bias potential may be controlled by a tact time that has been determined in advance to apply the bias potential, or otherwise by a sensor which detects that the wafer has been placed on the stage and transmits a detection signal as a trigger to apply the bias potential. Further, the closing operation of the access ports 437 and 325 by the shutter system 45 may be detected so as to use the detection signal as the trigger to apply the bias potential. Yet further, in case of using the electrostatic chuck, the chucking operation by the electrostatic chuck may be detected so as to use the detection signal as the trigger to apply the bias potential.

Figure 5:
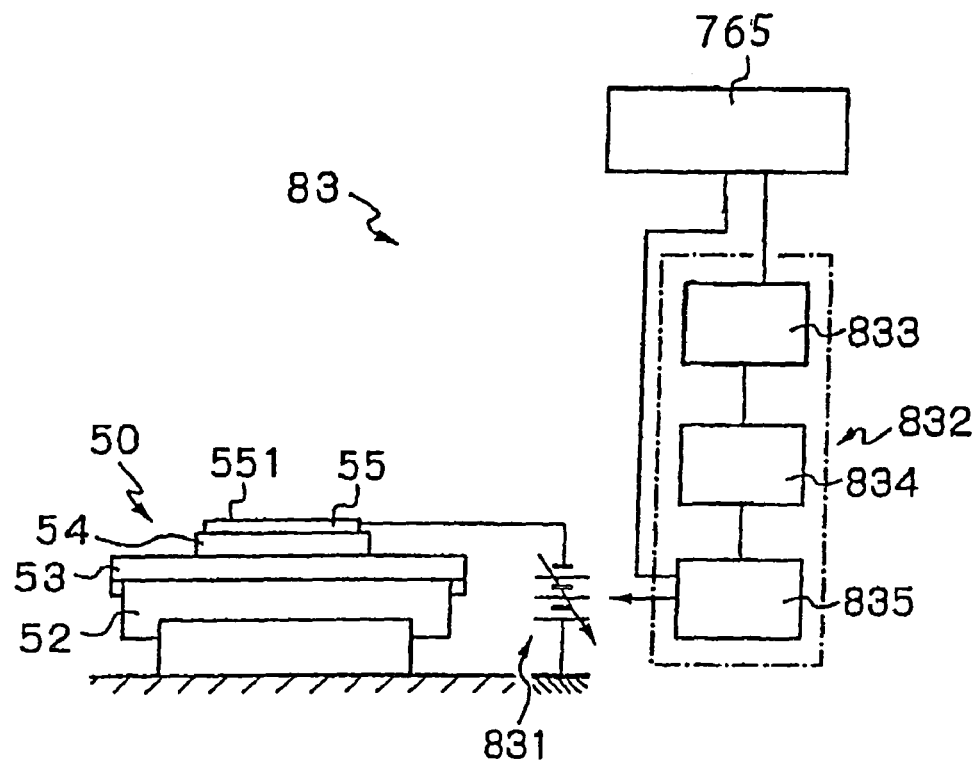
FIG. 5 illustrates a potential supply mechanism of the sample inspection system.
Figure 6:
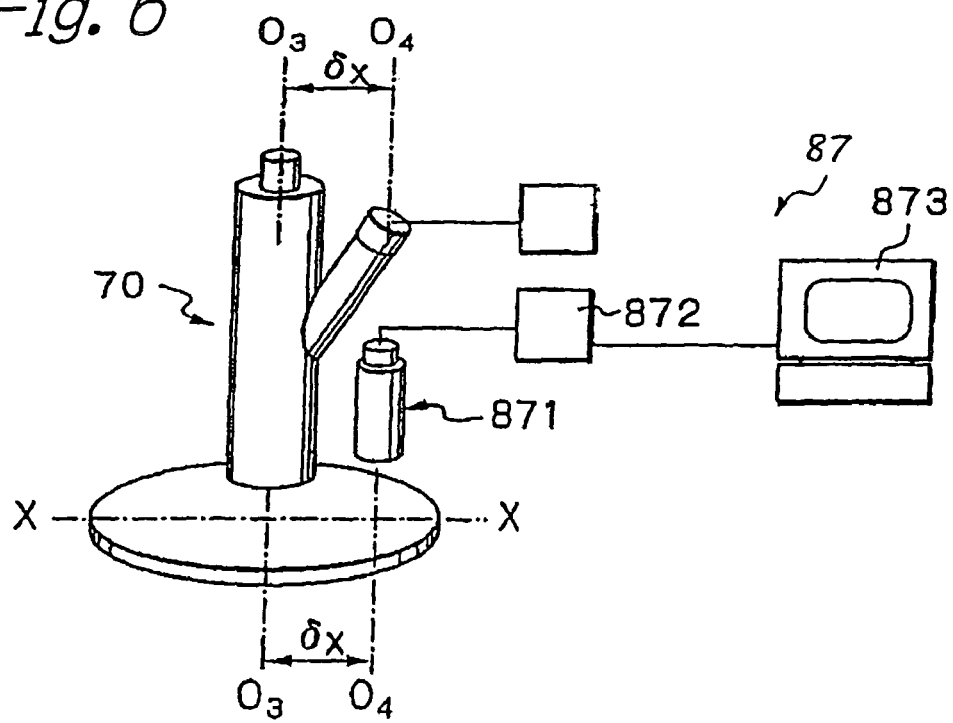
FIG. 6 illustrates an electron beam calibration mechanism of the sample inspection system in FIG. 1.

FIG. 5 shows a mechanism 83 installed in the stage device 50 to apply the negative-bias potential (retarding potential) to the wafer W. This potential application mechanism 83 is intended to control the generation of the secondary electrons by applying the potential in a range of ±some V to the platform 551 of the stage on which the wafer W is placed, based on the fact that the secondary electron data emanated from the wafer W (the generation rate of secondary electron) depends on the potential of the wafer W. Further, this potential application mechanism 83 also provides a function for decelerating the original energy of the irradiating electrons so as to irradiate the wafer W with the irradiating electron energy in a range of about 100 to 500 eV.

The potential application mechanism 83 comprises, as shown in FIG. 5, a voltage applying device 831 electrically connected to the loading surface 551 of the stage device 50, and a charge-up check and voltage determination system (hereinafter, referred to as a check and determination system) 832. The check and determination system 832 comprises a monitor 833 electrically connected to an image forming section 765 in a detecting system of the electron optical device 70, which will be described later, an operator 834 connected to the monitor 833 and a CPU 835 connected to the operator 834. The CPU 835 supplies a signal to the voltage applying device 831. The potential application mechanism 83 is designed to look for a potential that is not likely to charge the wafer subject to the inspection and applies that potential.

One method for inspecting the wafer W for any electrical defects may take advantage of the fact that the voltage of the portion to be electrically insulated in a normal condition varies when it is brought into conducting state. This may be achieved by a procedure in which firstly, charges are added in advance to the wafer W to thereby produce a voltage difference between one portion which is to be electrically insulated in a normal condition and has been kept actually in the normal condition and the other portion which is to be electrically insulated in the normal condition but has been brought into the conducting state by some reasons; secondly, the data containing the voltage difference is obtained by irradiating the electron beam to these portions; and then the thus obtained data is analyzed to detect that the latter portion has been actually in the conducting state.

The operations during a process for transferring the wafer W in the cassette c onto the stage device have been described, and in the process for returning the wafer W, which has been placed on the stage 50 and finished with a predetermined processing, from the stage device 50 back into the cassette c, the operations as described above should be performed in the inverse sequence. Further, since the first transfer unit 61 can transfer the wafer W between the cassette c and the wafer rack 47 while the second transfer unit 63 is transferring another wafer W between the wafer rack 47 and the stage device 50 so as to keep the a plurality of wafers loaded in the wafer rack 47, the inspection process can be progressed efficiently.

The pre-charge unit 81 is arranged within the working chamber 31 in a location adjacent to an optical column 71 of the electron optical device 70, as shown in FIG. 1. The present inspection apparatus employs such a system in which a device pattern or the like formed in the surface of the wafer W is inspected by irradiating the electron beam and scanning thereby the wafer W as an object to be inspected. Accordingly, in operations, the data of the secondary electrons generated by the irradiation of the electron beam are collected as the data of the wafer surface, wherein depending on the material of the wafer, energy of the irradiated electrons and so on, the wafer surface may be occasionally charged, or charged-up. In this regard, the wafer surface may possibly have some regions that would be charged intensively and other regions that would be charged moderately. If the wafer surface is not evenly charged, then the secondary electron data should be uneven, inhibiting the acute data from being obtained. To prevent unevenness, the pre-charge unit 81 having a charged particle irradiating section 811 is provided. In order to eliminate the uneven charging, prior to the irradiation of the electrons for the inspection onto a predetermined location on the wafer W to be inspected, charged particles are irradiated from the charged particle irradiating section 811 of the pre-charge unit 81. The charge-up of the wafer surface can be detected by forming in advance an image of the wafer surface to be detected and making an evaluation on said image, and based on the detection result, the pre-charge unit 82 may be actuated. In the pre-charge unit 81, the primary electron beam may be irradiated in its out-of-focus condition.

Figure 8:
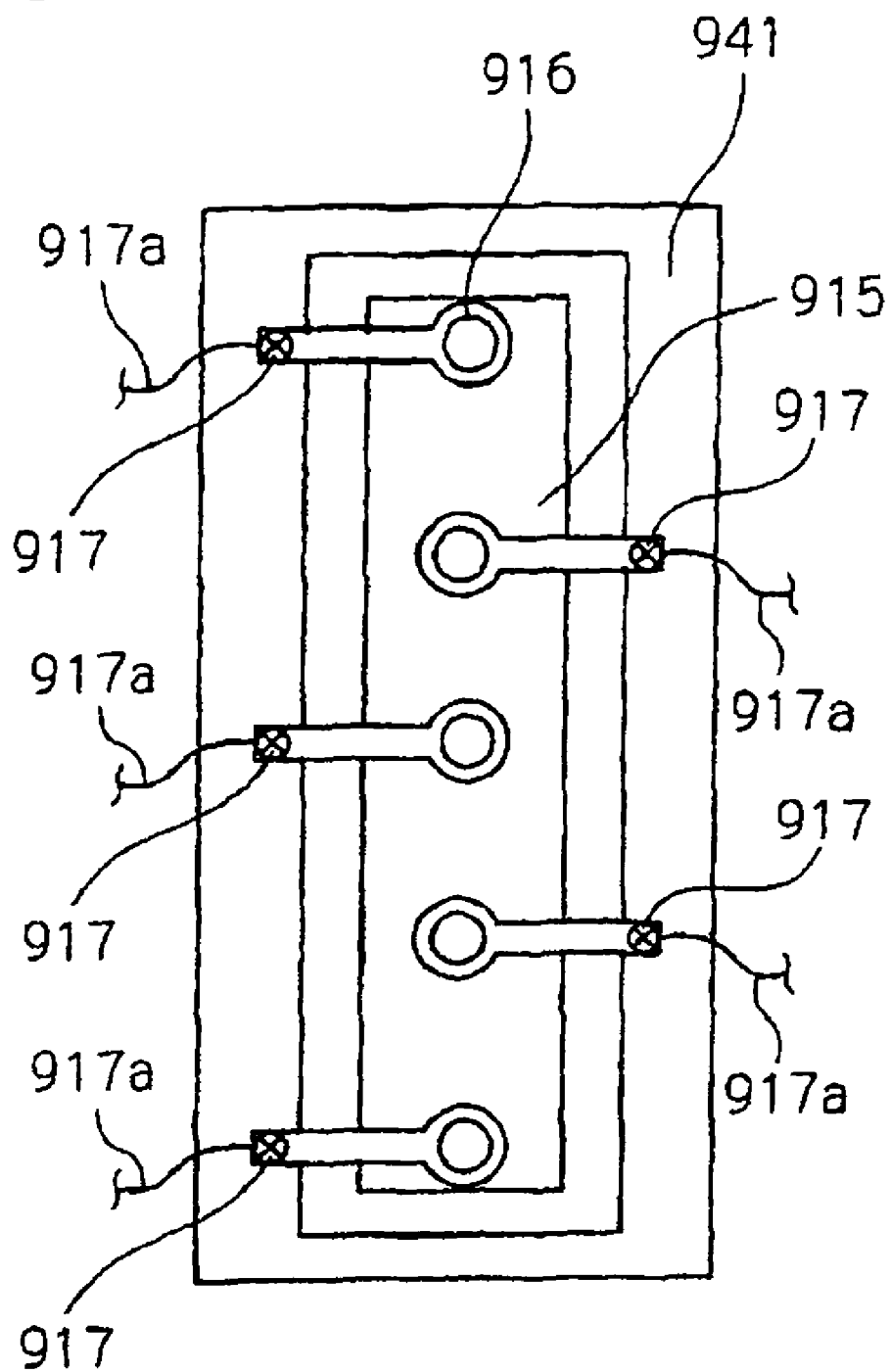
FIG. 8 is an enlarged diagram of a multi-anode of the electron beam apparatus shown in FIG. 7.

The inspection system 1 shown in FIG. 1 comprises an alignment controller 87. This alignment controller 87 is implemented by an apparatus for aligning the wafer W with respect to the electron optical device 70 by using the stage device 50, and it can provide the controls, as shown in FIG. 8, including a coarse aligning of the wafer W by a wide field observation of the wafer W using an optical microscope 871 in a lower magnification than that used in the electron optical device 70, an aligning of the wafer W in a high magnification by using an electron optical system of the electron optical device 70, a focal adjusting, an inspected region setting, a pattern alignment and the like. The reason the optical system is used to inspect the wafer W in the low magnification is that it is required in order to execute the inspection of the pattern of the wafer W automatically that the alignment mark should be detected easily by the electron beam when the pattern of the wafer W is observed by using the electron beam to thereby make a wafer alignment.

Preferably, the optical microscope 871 is operatively installed within the main housing 32 so as to be movable, and a light source (not shown) for actuating the optical microscope 871 is also disposed within the main housing 32. The electron optical system for providing the observation in the high magnification may share the electron optical systems in the electron optical device 70, or a primary optical system 701 and a secondary optical system 702. To make an observation in the low magnification for the point subject to the observation on the wafer W, the X-stage 53 of the stage device 50 is moved in the X-direction to bring the point subject to the observation on the wafer into the field of view of the optical microscope 871. The optical microscope 871 is used to look at the wafer W through a wide field of view, and the position on the wafer, which is to be observed, is indicated on a monitor 873 via a CCD 872, based on which the point of observation can be determined approximately. In this case, the magnification of the optical microscope 871 may be progressively changed from low to high.

Then, the stage device 50 is moved by a distance corresponding to a spacing δx between an optical axis $O_3$-$O_3$ of the electron optical device 70 and an optical axis $O_4$-$O_4$ of the optical microscope 871 to thereby bring the point on the wafer W subject to the observation, which has been previously determined with the optical microscope 871, into the position in the field of view of the electron optical device 70. In this case, since the distance δx between the axial line $O_3$-$O_3$ of the electron optical device 70 and the optical axis $O_4$-$O_4$ is known beforehand, only moving the point subject to the observation by the distance δx can bring it into the position for visual recognition by the electron optical device 70. It is to be noted that although in this illustration the electron optical device 70 and the optical microscope 871 are spaced from each other only along the X-axial line, they may be spaced both along the X- and the Y-axial directions. After the point subject to the observation is transferred into the visual recognition point of the electron optical device 70, the SEM image of the point subject to the observation is taken by the electron optical systems of the electron optical device 70 in the high magnification, and said image may be stored and/or may be indicated in a monitor via a camera unit.

In this way, after the point on the wafer W subject to the observation is indicated on the monitor by the electron optical system in the high magnification, a misalignment of the wafer W in the rotational direction with respect to the revolving center of the turntable 54 of the stage device 50, or a misalignment δθ of the wafer W in the rotational direction around the optical axis $O_3$-$O_3$ of the electron optical system, is detected by using a known method, and also a misalignment of a predetermined pattern in the X- and the Y-axial directions with respect to the electron optical device 70 is detected. Based on thus obtained values of detection as well as separately obtained data of the inspection mark formed in the wafer W or the set of data concerning to the geometry of the pattern of the wafer W and the like, the operation of the stage device 50 is controlled to provide the alignment of the wafer W.

With understanding of the above explanation, some preferred embodiments of the electron optical device 70 used in the defect inspection apparatus according to the present invention will now be described.

Figure 7:
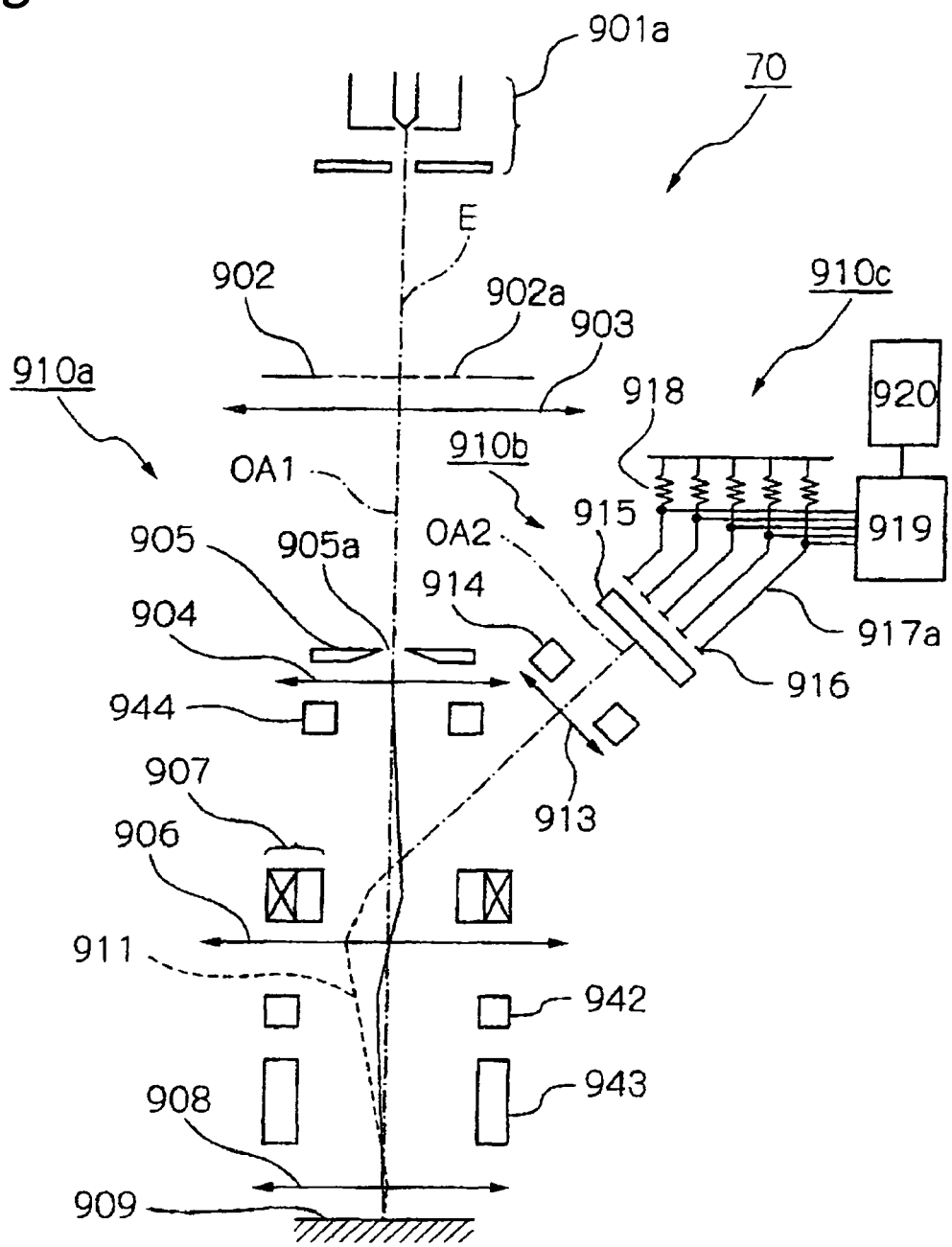
FIG. 7 schematically illustrates a first embodiment of an electron beam apparatus using a multi-beam system according to the invention.

FIGS. 7 and 8 generally show the configuration of a first embodiment of an electro-optical apparatus 70 for use in the inspection system, according to the present invention, where an electro-optical apparatus 70 is a multi-beam type electro-optical apparatus. As shown, the electro-optical apparatus 701 comprises a primary electro-optical system (hereinafter simply called the "primary optical system") 910a, a secondary electro-optical system (hereinafter simply called the "secondary optical system") 910b, and a detection system 910c.

The primary optical system 910 is an optical system for irradiating an electron beam E to a pattern which constitutes a semiconductor device (for example, a die) formed on a sample 909 such as a wafer, and comprises an electron gun 901a for emitting an electron beam E, a multi-aperture plate 902 formed with a plurality of small holes 902a arranged in a linear or a two-dimensional array for forming the electron beam E emitted from an electron gun 901a into a plurality of electro beams (multiple beams); an electro lens 903 for converging the multiple beams, an AN aperture member 905 for defining an NA aperture 905a, an electrostatic lens 904 for reducing the multiple beams which have passed through the NA aperture 905a, an electro-static deflector 944, an ExB separator 907, a first objective lens 906, deflectors 942, 943, and a second objective lens 908. As shown in FIG. 7, these components are arranged in order such that the electron gun 901a is positioned at the top, and the optical axis OA1 of the electron beam E emitted from the electron gun 901a is perpendicular to the surface of the sample 909.

A plurality of small holes (throughholes) 902a of the multi-aperture plate 902 are arranged within a circumference centered at the optical axis OA1 of the primary optical system 910a, and formed such that adjacent small holes, when projected onto the y-axis, are at equal intervals in the y-axis direction. Accordingly, the multiple beams formed by the respective small holes 902a are also arranged within the circumference centered at the optical axis OA1, and a minimum interval between the beams maintains a distance equal to or larger than the resolution of the second optical system 910b, and these beams are at equal intervals in the y-axis direction.

The second optical system 910b comprises a converging lens 913 and a deflector 914 disposed along an optical axis OA2 which inclines with respect to the optical axis OA1 near the ExB separator 907. A minimum interval between the respective electron beams on the surface of the sample 909 is larger than the resolution on the surface of the sample 909 in the secondary optical system 910b.

The detection system 910c comprises a micro-channel plate (MCP) 915 which has a channel corresponding to each small hole 902a of the multi-aperture plate 902, a multi-anode 916 and resistor 918 corresponding to each small hole 902a, an image forming circuit 919 including an A/D converter, and a memory 920. As shown in FIG. 8, the multi-anode 916 comprises a thin line in a loop shape arranged in a rectangular structure, and is configured to promptly emit gases emitted from the MCP. Also, one end 917 of each multi-anode 916 is fixed to a substrate 941 of ceramics, and is also connected to the resistor 918 and image forming circuit 919 through lead wire 917a.

With the configuration as described above, the electron beam E is reduced by the reducing lens 904 and objective lenses 906, 908, and each beam arranged in the Y-axis direction is narrowed down and focused on sample 909. These electron beams E are scanned on the sample 909 in the X-axis direction, while they are deflected by the deflectors 942, 943. Then, secondary electrons generated from scanned points travel as indicated by a dotted line 911, and the intervals between the secondary electrons is magnified by the second objective lens 908, first objective lens 906, and magnification lens 913, and simultaneously, the scaling factor is adjusted such that the interval between the secondary electrons is equal to the interval of the multi-anodes 916 disposed behind the MCP (micro-channel plate).

Figure 9:
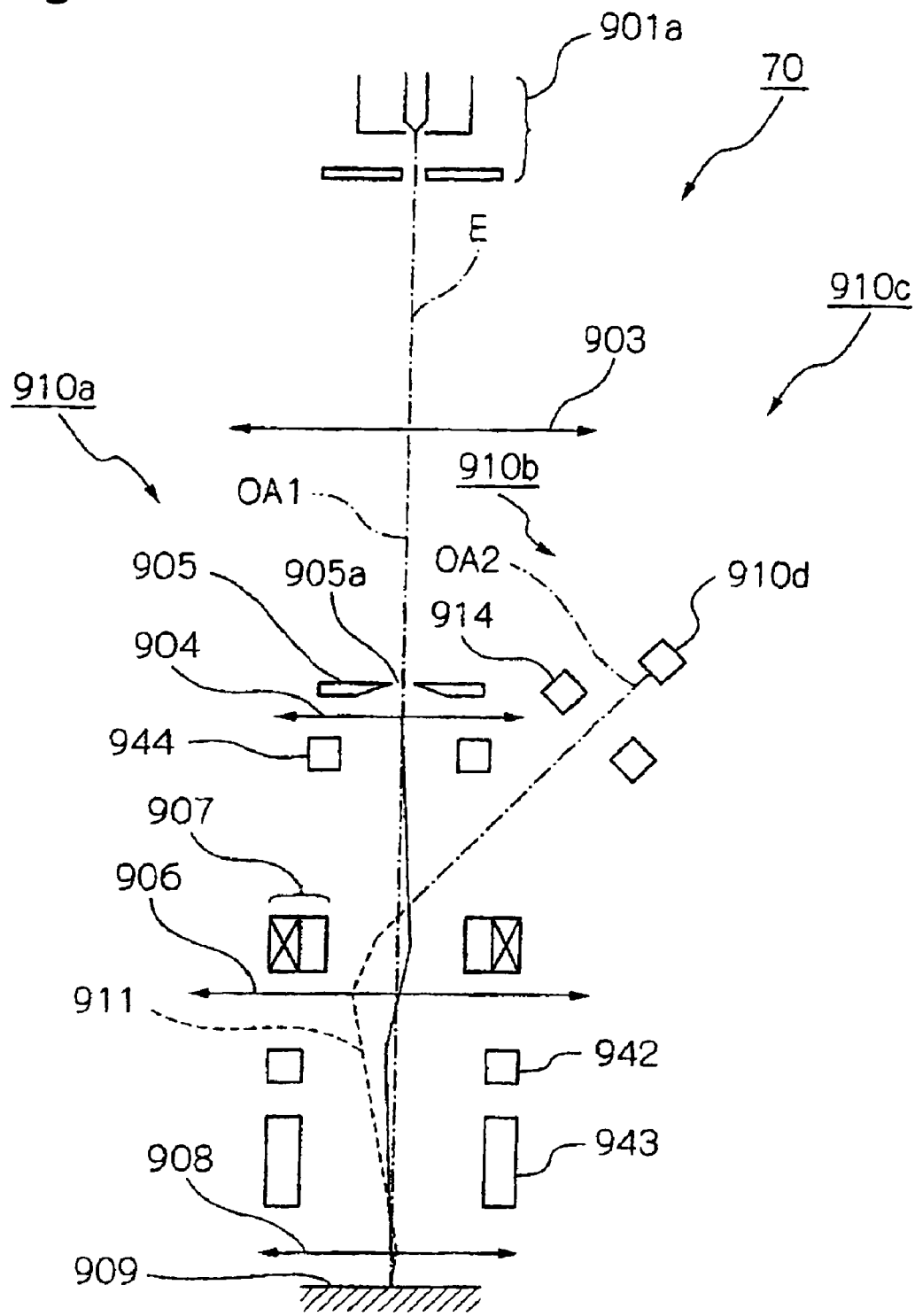
FIG. 9 schematically illustrates a second embodiment of an electron beam apparatus using a single beam system according to the invention.

Next, FIG. 9 generally shows the configuration of a second embodiment of an electro-optical apparatus 70 for use in a testing or inspection apparatus according to the present invention. This second embodiment comprises a single-beam type scanning electro-optical apparatus, and differs from the first embodiment in FIG. 7 in that the multi-aperture plate 902, lens 913, and multi-anode 16 (FIG. 8) are not needed. Simultaneously, the single-beam type scanning electro-optical apparatus differs in that the detection system 910c in the multi-beam type apparatus is replaced by a detector 910d which comprises a PIN diode, a scintillator, and a photomultiplier. In FIG. 9, the same components as those shown in FIG. 7 are designated the same reference numerals, and descriptions thereon are omitted.

In the single-beam type electro-optical apparatus 70 shown in FIG. 9, since information for one pixel is detected by one beam, the detector 910d may simply detect a signal strength corresponding to the number of secondary electrons generated from a tested surface of the wafer 909, thus resulting in an advantage that a simple detection system suffices.

In the inspection apparatus which employs the electro-optical apparatus 70 shown in FIG. 7 or FIG. 9, when electron beams are irradiated to a substrate such as a wafer formed with a plurality of dies to acquire the image of a pattern on the tested surface for a defect test, each die should be theoretically be arranged as designed on the acquired image as well. However, as previously described, actually, the arrangement of dies on the formed image may differ from the arrangement of dies on the wafer, due to distortions of a stage guide for moving a stage, exposure errors occurring in a lithography process, and the like. According to a test in actual use, there are generally position errors of approximately 2-3 μm. In such an event, the position errors must be corrected in order to acquire an image equal to the arrangement of dies on the wafer, because the detection of defects through image comparison is hindered.

Thus, since it is difficult to correct all error factors using a correction XY map (dynamic range of ±20 μm) in order to correct the position errors mentioned above, first in the present invention, a correction function $(\Delta x, \Delta y) = f1(x,y)$ has been previously determined through recursive processing with a detailed error map generated therefore at a predetermined period (for example, approximately every half-year) for a position error (static error) correction term with high reproducibility, caused by mechanical factors which affects the absolute coordinates and the accuracy of a die-to-die comparison test. Then, during a test, the static errors are corrected using the correction function which has been previously processed and stored.

In this regard, for a position error (dynamic error) which affects the image quality such as blurring, which can dynamically vary, a correction function $(\Delta x, \Delta y) = f2(x,y)$ is determined on a wafer-by-wafer basis or the like for use in the correction during an actual test.

Then, the present inventors investigated how to correct the highly reproducible static errors, and revealed as a result that among static errors, an orthogonal error of the XY coordinate system which occupies the highest relative importance, and an error caused by a distorted mirror of a laser interferometer (mirror distortion error) occupy a relatively large relative importance. The orthogonal error refers to an error which is caused by an assembling accuracy and a flatness of an interferometer mirror and a stage guide. Accordingly, the present invention is characterized by reducing these errors. In this specification, the correction of the orthogonal error is called a correction of "level 1," and the correction of the mirror distortion error is called a correction of "level 2."

In this regard, the highly reproducible static errors also include errors due to the rotation of a wafer, shift errors in the X-axis and Y-axis directions of the wafer, and scale errors in the X-axis and Y-axis direction, other than the orthogonal error and mirror distortion error, and according to the present invention, these errors can also be detected and corrected.

In this way, the correction of the static errors in two modes solves a problem of a small dynamic range provided when they are corrected by deflecting electron beams in the prior art example, and a reduction in processing time and simplification can be achieved by not using MAP which requires a large amount of data during a test of wafers, thus making it possible to conduct a test with a high accuracy and high throughput.

Figure 10:
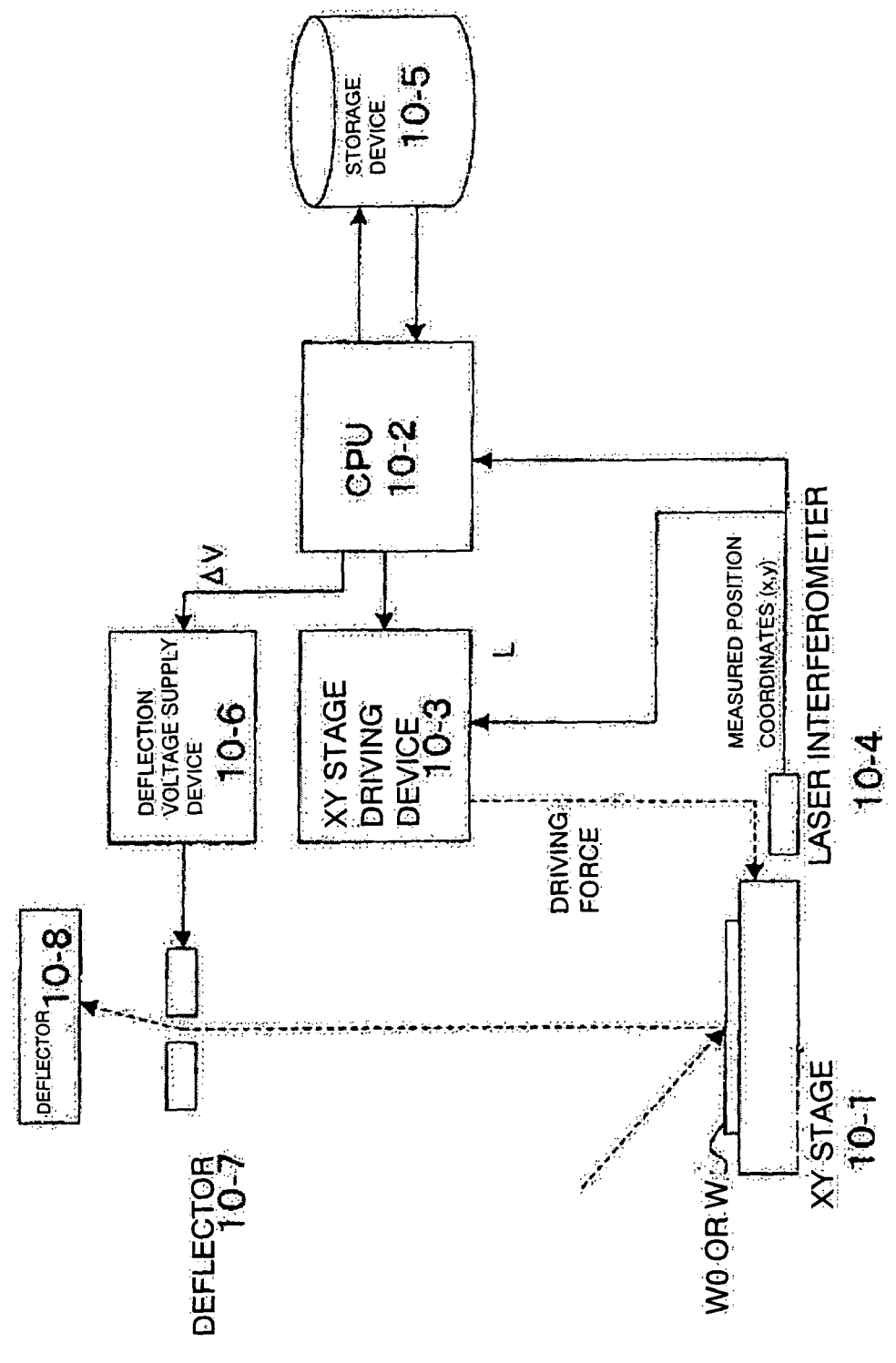
FIG. 10 is a block diagram illustrating an XY coordinate compensation system according to the invention.

FIG. 10 is a block diagram showing the configuration for correcting stage errors in an electron beam apparatus according to the present invention. Referring to FIG. 10, the following detailed description will be focused on the corrections of level-1 and level-2 in a variety of embodiments.

First Embodiment

First, a reference wafer $W_0$ for which correct XY coordinates, i.e., ideal position coordinates $(x_0, y_0)$ of a plurality of reference points have been previously known, is placed on an XY-stage 10-1 of a testing apparatus. An XY-stage driving device 10-3 is driven under the control of a CPU 10-2 such that the reference points are irradiated with primary electron beams. Then, a laser interferometer 10-4 measures the position coordinates, i.e., measuring position coordinates $(x,y)$ of a plurality of reference points on the wafer. The number of reference points under measurement may be an arbitrary number as long as it is equal to or larger than five, in consideration of the level-2 correction, but coordinates of approximately 30-60 reference points are preferably measured in order to make more precise corrections. Accordingly, actually, there are 30-60 sets of ideal position coordinates $(x_0, y_0)$ and measuring position coordinates $(x,y)$. Assume that ideal position coordinates $(x_0, y_0)$ have been previously stored in a storage device 10-5.

Then, the CPU 10-2 calculates the difference:

$$\Delta x = x_0 - x$$

$$\Delta y = y_0 - y$$

between the ideal position coordinates $(x_0, y_0)$ of the reference point and the measuring position coordinates $(x,y)$, and stores the position error $(\Delta x, \Delta y)$ in the storage device 10-5 in correspondence to the measuring position coordinates $(x,y)$.

Next, the CPU 10-2 substitutes the stored position error $(\Delta x, \Delta y)$ and measuring position coordinates $(x,y)$ into the following equations (1) and (2) to perform recursive processing to determine coefficients $a_1 \sim e_1$ and $a_2 \sim e_2$:

$$\Delta x = a_1 + b_1 x + c_1 y + d_1 x^2 + e_1 y^2 \quad (1)$$

$$\Delta y = a_2 + b_2 x + c_2 y + d_2 x^2 + e_2 y^2 \quad (2)$$

Then, an orthogonal error is calculated using the coefficient c1 and b2 within the calculated coefficients $a_1 \sim e_1$ and $a_2 \sim e_2$:

Orthogonal Error = $b_2 - c_1$

In the foregoing equations, a1 represents an X-axis direction shift error; $a_2$ a Y-axis direction shift error; b1 an X-axis direction scale error; $c_2$ a Y-axis direction scale error; $b_2$ a wafer rotation error with respect to the X-axis; and c1 a waver rotation error with respect to the Y-axis. Therefore, $b_2-c_1$ represents the orthogonal error of the XY-axes. The determination of these coefficients is preferably introduced such that a maximum position error after the correction is reduced to 2-3 μm or less.

In this way, the orthogonal error (=$b_2-c_1$) is calculated, as subjected to the level-1 correction. The CPU 10-2 stores the resulting orthogonal error in the storage device 10-5.

The CPU 10-2 also substitutes the coefficients $d_1$, $d_2$, $e_1$, $e_2$ within the calculated coefficients $a_1 \sim e_1$ and $a_2 \sim e_2$ into the following Equations (3) and (4):

$$\Delta x = d_1 x^2 + e_1 y^2 \qquad (3)$$

$$\Delta y = d_2 x^2 + e_2 y^2 \qquad (4)$$

($\Delta x$, $\Delta y$) represented by Equations (3) and (4), into which the coefficients have been substituted, represents a mirror distortion error, thus resulting in an equation which represents an error subjected to the level-2 correction. The CPU 10-2 stores the resulting equations (i.e., Equations (3) and (4) with the coefficients substituted thereinto) in the storage device 10-5. In this regard, while ($\Delta x$, $\Delta y$) represented by Equations (3) and (4) actually includes error components other than the mirror distortion error, it can be said that Equations (3) and (4) represent the mirror distortion error because the mirror distortion error is the largest error component.

Figure 11:
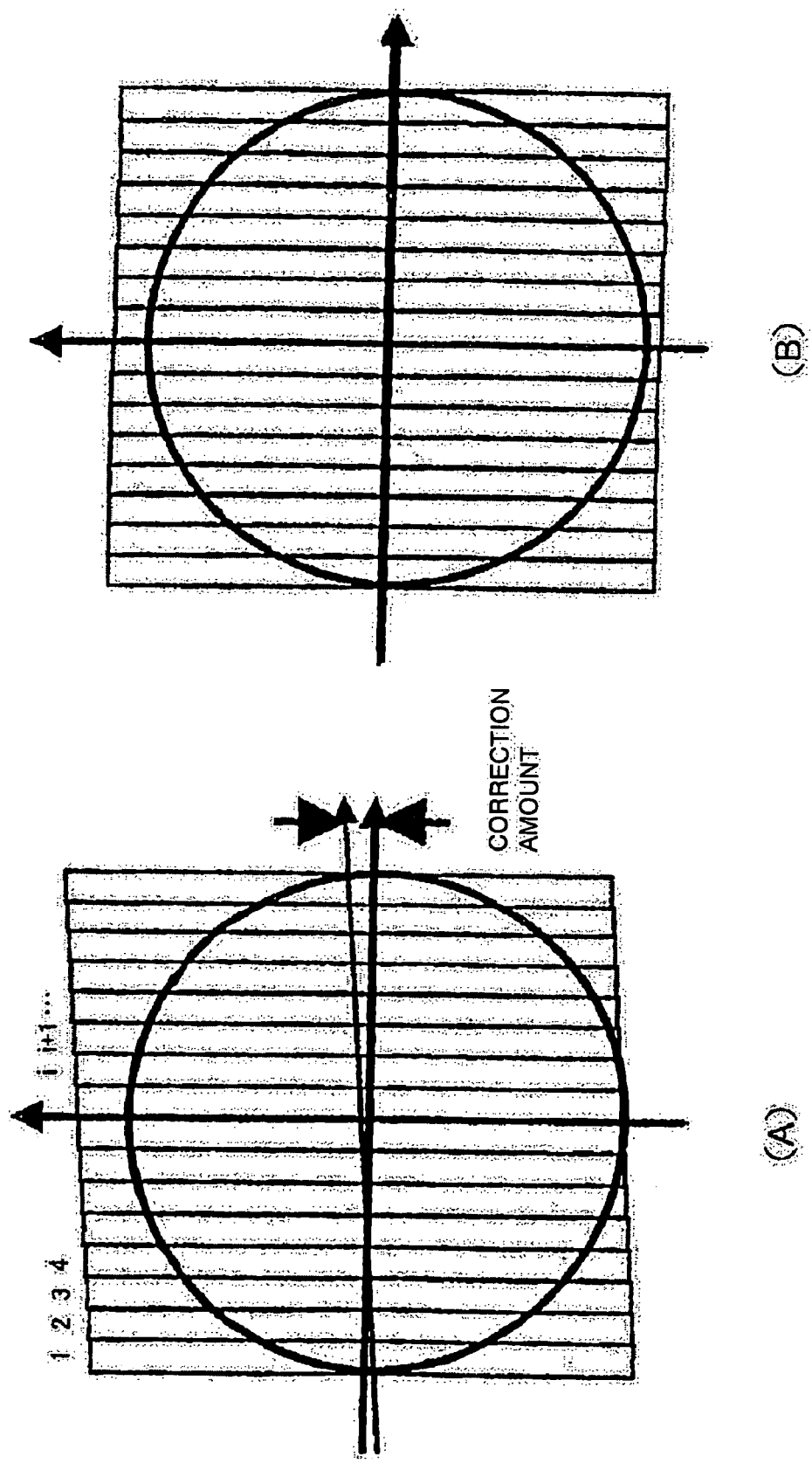
FIGS. 11A and 11B are diagrams for explaining a method of compensating an orthogonal error of an XY coordinate, which is executed in the XY coordinate compensation system illustrated in FIG. 10.

Since the level-1 correction is intended to correct an XY orthogonal error, the X-coordinate may be simply rotated by $b_2-c_1$. Actually, however, the following procedure is conducted in order to equivalently perform the same during a test. Specifically, as shown in FIG. 11(A), the XY orthogonal error is corrected by adding an offset i*Δk (Δk: an offset value when a unit offset value is swath 1) of a value corresponding to each swath i to the Y-coordinate for each swath 1, 2, . . . , i, . . . during a test. In this regard, since the scanning direction (scanning axis) is matched with the Y-axis by a θ-stage, the correction is integrated into the rotation of the X-axis, i.e., the offset of the Y-axis coordinate.

As a result of adding the offset in this way, the orthogonal error of the XY coordinates can be reduced substantially to zero, as shown in FIG. 11(B). The unit offset value Δk is calculated by the CPU 10-2 using the orthogonal error $b_2-c_1$ and a swath width (Δk=one swath width*tan($b_2-c_1$)), and stored in the storage device 10-5. The CPU 10-2 determines "i" in accordance with the X-axis provided from the laser interferometer 10-4 during a test or inspection of an actual sample pattern, reads Δk from the storage device 10-5, and adds I*Δk to the Y-coordinate provided from the laser interferometer 10-4. In this way, the orthogonal error of the XY-coordinates is corrected.

The X-axis direction shift error "a"1 and Y-axis direction shift error "$a_2$" are corrected by registering again the origin of a die before starting a test of a sample pattern.

As is apparent from the foregoing, the level-1 correction involves deriving Equations (1) and (2) through recursive processing, and offsetting each swath in the Y-axis direction by an amount associated with the swath in order to correct the XY orthogonal error resulting therefrom. Since the XY orthogonal error is generally static, the offset amount Δk may be calculated approximately every half year to update the offset value Δk in the storage device 10-5 in the same testing apparatus.

While the level-2 correction is made during an actual test, as the test is started, the CPU 10-2 reads Equations (3) and (4) derived in the foregoing manner from the storage device 10-5, and substitutes measuring position coordinates (x,y) provided by the laser interferometer 10-4 into these equations to calculate Δx and Δy in real time. Then, the storage device 10-5 has previously stored a lookup table which represents the relationship between the position error (Δx, Δy) and a correction value ΔV for a voltage applied to a deflector 10-7, such that the CPU 10-2 references the lookup table to determine a correction voltage ΔV for correcting the position error (Δx, Δy) calculated by Equations (3) and (4) at that time, and controls a deflection voltage supply device 10-6 to supply the correction voltage to the deflector 10-7. In this way, the secondary electron beams are deflected to form an image on a detector 10-8. The position at which the image is formed is coincident to a position at which the mirror distortion error is reduced.

As is apparent from the foregoing, the level-2 correction involves previously determining Equations (3) and (4), calculating a position error at a test point using these equations in real time during an actual test, and deflecting electron beams to the detector 10-8 such as MCP or the like based thereon, thereby correcting a focusing position on the detector.

Figure 12:
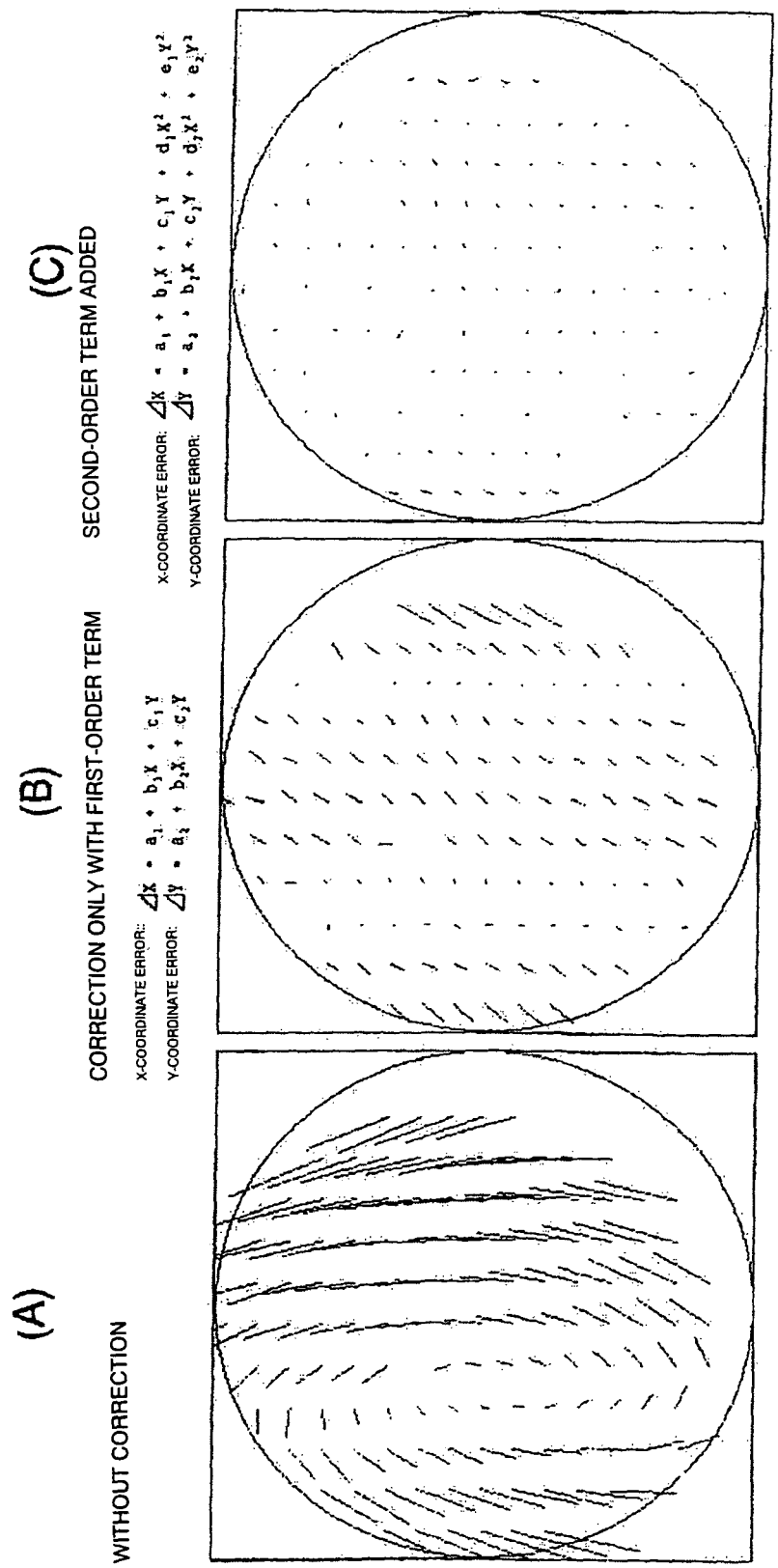

FIGS. 12(A)-12(C) show position errors in vector representation, measured using a wafer, the XY coordinates of which are know, where (A) shows a position error when no position correction is made; (B) a position error when the level-1 correction is only made; and (C) a position error when both the level-1 and level-2 corrections are made. For example, the amount corrected by the level 1 is approximately ±10 μm, and the amount corrected by the level 2 is approximately ±0.5 μm.

As is apparent from these figures, it can be seen that the position error is largely reduced by making the level-1 and level-2 corrections, as compared with without correction and the level-1 correction alone. Consequently, it is understood that the correction according to the present invention is extremely effective for reducing the position error.

Second Embodiment

In this second embodiment, the CPU 10-2 also calculates errors (Δx, Δy) at a plurality of reference points using the reference wafer $w_0$, finds coefficients $a_1 \sim e_1$ and $a_2 \sim e_2$ through recursive processing of Equations (1) and (2), and determines an orthogonal error, in a manner similar to the first embodiment. Subsequently, the CPU 10-2 corrects measuring position coordinates (x,y) of a plurality of reference points on the reference wafer $w_0$ using the determined orthogonal error. This correction is similar to the correction of the orthogonal error in the first embodiment.

Then, coefficients $a_1 \sim e_1$ and $a_2 \sim e_2$ of the following equations (identical to Equations (1) and (2)) are calculated through recursive processing using the corrected measuring position coordinates (x', y'):

$$\Delta x = a_1 + b_1 x' + c_1 y' + d_1 x'^2 + e_1 y'^2 \qquad (1')$$

$$\Delta y = a_2 + b_2 x' + c_2 y' + d_2 x'^2 + e_2 y'^2 \qquad (2')$$

Then, the calculated coefficients $a_1 \sim e_1$ and $a_2 \sim e_2$ are substituted into Equations (1') and (2') (i.e., Equations (1) and (2)), and the resulting equations are stored in the storage device 10-5 as equations which represent a mirror distortion error. In this second embodiment, the mirror distortion error is represented by Equations (1') and (2'), but the coefficients $a_1 \sim c_1$ and $a_2 \sim c_2$ in these equations are substantially zero when the orthogonal error is corrected, so that it can be said that Equations (1') and (2') are substantially equivalent to Equations (3) and (4).

The level-1 correction and level-2 correction, when a wafer W is tested by driving an electron beam apparatus, are made in a manner similar to the first embodiment (however, different equations are used in the correction of the mirror distortion error).

Third Embodiment

Likewise, in this third embodiment, errors ($\Delta x$, $\Delta y$) at a plurality of reference points are calculated using the reference wafer $w_0$ in a manner similar to the first embodiment. Then, the coefficients $a_1 \sim c_1$ and $a_2 \sim c_2$ are calculated through recursive processing using the following Equations (5) and (6) instead of Equations (1) and (2), and an orthogonal error in the XY coordinate system is calculated as $b_2 - c_1$:

$$\Delta x = a_1 + b_1 x + c_1 y \quad (5)$$

$$\Delta y = a_2 + b_2 x + c_2 y \quad (6)$$

Next, the CPU 10-2 corrects measuring position coordinates (x,y) at a plurality of reference points on the reference wafer $w_0$ using the determined orthogonal error. Then, coefficients $d_1$, $e_1$, $d_2$, $e_2$ in the following Equations (3') and (4') (which are equivalent to Equations (3) and (4)) are calculated through recursive processing using the corrected measuring position coordinates (x',y'):

$$\Delta x = d_1 x'^2 + e_1 y'^2 \quad (3')$$

$$\Delta y = d_2 x'^2 + e_2 y'^2 \quad (4')$$

Then, the calculated coefficients $d_1$, $e_1$, $d_2$, $e_2$ are substituted into Equations (3') and (4'), and the resulting equations are stored in the storage device 10-5 as equations which represent a mirror distortion error.

The level-1 correction and level-2 correction, when a wafer W is tested by driving an electron beam apparatus, are made in a manner similar to the first embodiment. (However, different equations are used in the correction of the mirror distortion error.)

Fourth Embodiment

In the fourth embodiment, an orthogonal error is determined using Equations (5) and (6) in a manner similar to the third embodiment, and measuring position coordinates (x,y) of a reference point is corrected using the determined orthogonal error. Subsequently, the CPU 10-2 calculates coefficients $a_1 \sim e_1$ and $a_2 \sim e_2$ which satisfy Equations (1') and (2'), using the corrected measuring position coordinates (x', y'):

$$\Delta x = a_1 + b_1 x' + c_1 y' + d_1 x'^2 + e_1 y'^2 \quad (1')$$

$$\Delta y = a_2 + b_2 x' + c_2 y' + d_2 x'^2 + e_2 y'^2 \quad (2')$$

Then, the calculated coefficients $a_1 \sim e_1$ and $a_2 \sim e_2$ are substituted into Equations (1') and (2'), and resulting equations are stored in the storage device 10-5 as equations which represent a mirror distortion.

The level-1 correction and level-2 correction, when a wafer W is tested by driving an electron beam apparatus, are made in a manner similar to the first embodiment. (However, different equations are used in the correction of the mirror distortion error.)

As described above, in an electron beam apparatus, statically generated errors are dominated by a stage orthogonal error and an error due to mirror distortion, and in the invention, these errors are reduced by the level-1 correction and level-2 correction, respectively, thus making it possible to reduce a position error at a tested point on a wafer to determine ideal position coordinates.

In this event, the equations representative of the orthogonal error and the position error due to mirror distortion are previously defined and stored, such that the equations are read in the event of an actual test, and measuring position coordinates are substituted into the equation to correct the measuring position coordinates, so that the test can be conducted with a high accuracy and high throughput. Also, the deflection dynamic range of the deflector 10-7 is generally as low as approximately ±20 µm, but even in such an event, the orthogonal error is corrected by the level-1 correction, so that the remaining position error is reduced (see FIG. 12). Accordingly, the present invention can be utilized even with the deflector 10-7 with a small dynamic range.

Figure 13:
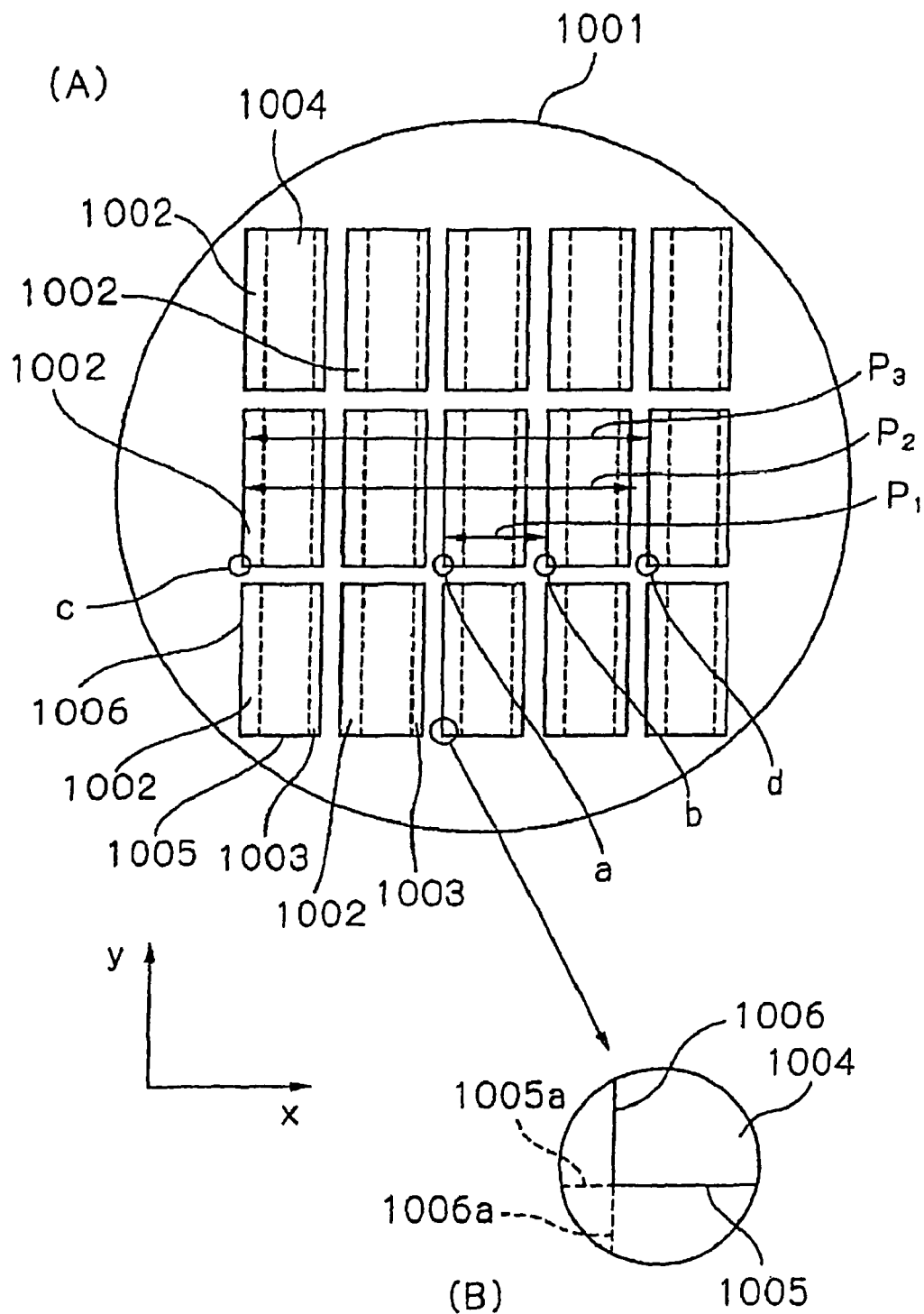
FIGS. 13A and 13B are diagrams for explaining wafer inspection by the electron beam apparatus, in which FIG. 13A and 13B schematically illustrate a whole wafer and an enlarged portion of a die on the wafer.

Now, defect determination will be described in detail. In determining defects, images of stripes 1002 mutually corresponding to different dies 1004 are compared with each other, as shown in FIG. 13(A). This is because it is anticipated that the same patterns are mutually included in corresponding stripes if there is no defect, and discrepancy results in the comparison result if there are defects.

In FIG. 13(A), when defects are detected by comparing patterns in the stripes 1002 of dies adjacent to each other on the same wafer with each other, a stage is successively moved in the Y-axis direction to successively observe two patterns which are compared, thus completing the test on the entire surface of the wafer in a short time.

Another defect detection approach may employ, for example, CAD information. Specifically, the same pattern as that included in the stripe 1002 is generated as a reference image on a memory through processing from CAD information for generating the pattern included in the stripe 1002, and this reference image is compared with a pattern on a wafer (an image of the stripe 1002 in FIG. 13(A)) to find the difference therebetween, thereby detecting defects.

In the approach for comparing patterns of two dies with each other, when the entire surface of a wafer is tested, a test time is reduced by successively testing the same pattern on dies on the wafer for dies adjacent to each other. In contrast, the approach for comparing with a reference image from CAD information, includes the steps of converting vector data of the CAD information to raster data which is image data, saving the raster data in a memory, and generating the reference image; converting the image in order to prevent an erroneous detection of a portion which is anticipated to produce a difference with the reference image on a tested image but is not a defect, for example, a corner portion of a pattern to reflect to the reference image; converting the concentration of the reference image to a concentration anticipated when the tested image is captured from the wafer; and matching the position of the reference image with the position of the tested image captured from the wafer. While any defect detection approach can detect defects in shape of the pattern and particles, the image is captured on the wafer using electron beams, so that voltage contrast information is provided as well, and even electric defects can be detected.

Figure 14:
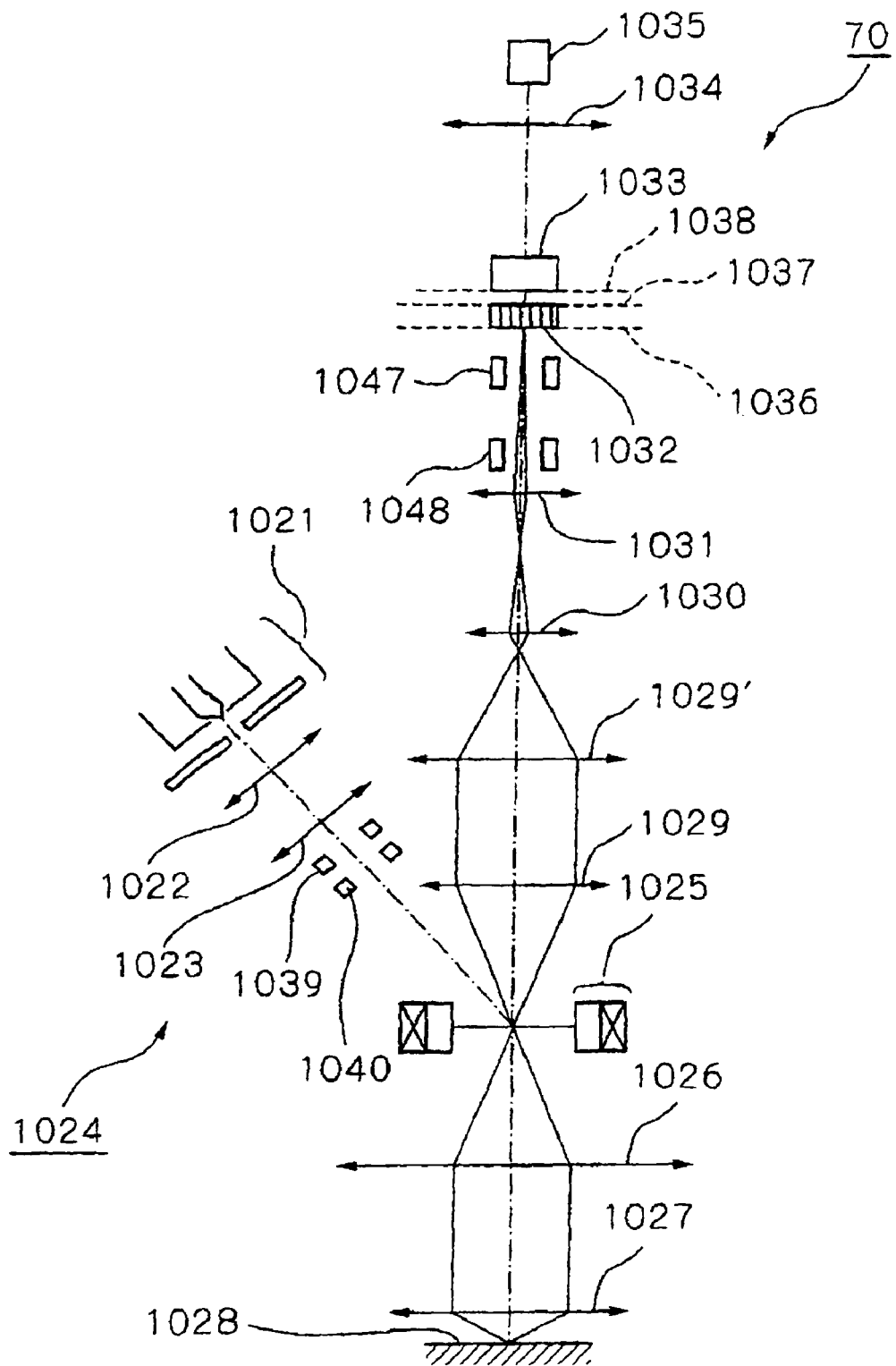
FIG. 14 schematically illustrates a third embodiment of an electron beam using an image projection system according to the invention.
Figure 15:
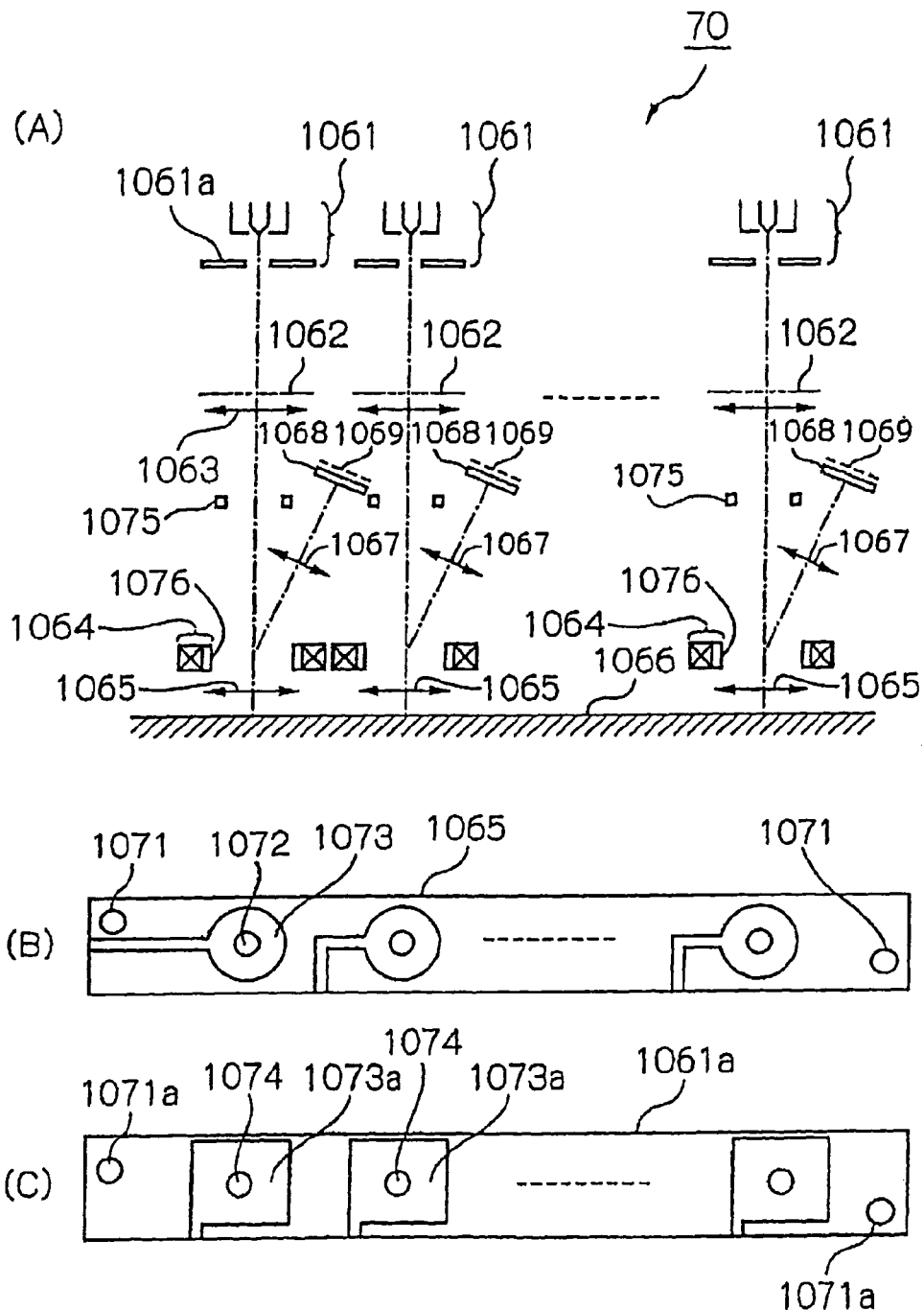

The pattern testing or inspecting method described above can be implemented in an apparatus which employs another type of electro-optical system shown in FIGS. 14 and 15. FIG. 14 generally showing the configuration of a third embodiment of an electro-optical apparatus 70 for use in a testing system 1 according to the present invention, where the electro-optical apparatus 70 employs a projection type. As shown, a primary optical system 1024 direct an electron beam from an oblique direction with respect to the normal of a wafer 1028, bends the electron beam substantially in a perpendicular direction to the surface under testing of the wafer 1028 by an ExB separator 1025, and irradiates the wafer 1028 with a rectangular beam. Secondary electrons emitted from the wafer 1028 are magnified by objective lens tablets 1027, 1026, magnification lens tablets 1029, 1029', and magnification lenses 1030, 1031, to focus a magnified image of the secondary electrons on an MCP 1032.

When the position of the wafer 1028 deviates from a design value due to variations in speed of the stage in the Y-direction, or when a scanned die deviates from a designed position, dies will deviate in position on the image generated by the secondary electrons unless any correction is made. For correcting this positional deviation, the level-1 and -2 corrections are made. In the level 2, a feed-back or a feed-forward correction is made for deflectors 1047, 1048.

In FIG. 14, the secondary electrons are focused on the MCP 1032 and amplified thereby. The secondary electrons amplified by the MCP 1032 are converted to light by a scintillator coated on the lower surface of an FOP (fiber optical plate) 1033, focused on a TDI detector 1035 by an optical lens 1034, and converted to an electric signal.

FIG. 15(A) is a diagram generally showing the configuration of a fourth embodiment of an electro-optical apparatus 70 for use in a testing apparatus according to the present invention, where the electro-optical apparatus 70 employs an electro-optical system of multi-optical axis multi-beam type. The electro-optical apparatus 70 comprises an electron gun 1061, a multi-aperture plate 1062, a condenser lens 1063, an objective lens 1065, an ExB separator 1064, a secondary electron image magnification lens 14067, an MCP 1068, and a multi-anode 1069, where these components are configured to be arranged on a line with respect to a wafer 1066 in a plurality of sets. As a result, the optical axis of a primary optical system in each set is set at the same position of a corresponding stripe of a different die.

Optical parts of the primary optical system represented by the objective lens 1065 and anodes 1061a are such that, as shown in FIG. 15(B), a plurality of holes, which later serve as optical axes, are pierced through a single ceramics substrate, which exhibits the coefficient of thermal expansion equal to substantially zero, and aligned with a knock hole 1071, to provide a plurality of optical elements. The objective lens 1065 is selectively coated with a metal inside of electrode holes 1072 and near the optical axis to prevent charging, such that an independent voltage can be applied around each electrode hole 1072.

As shown in FIG. 15(C), for the anodes 1061a, a metal coating is applied around each anode hole 1074, such that they can be independently applied with voltages, so that an anode current can be adjusted for each anode hole. The interval of these anode holes 1074 is set to precisely match an integer multiple of the pitch of dies on the wafer 1066 in the X-axis direction, and therefore, an electron beam which passes through each anode hole can test the same position of corresponding stripes of different dies. In this regard, the anodes 1061a can be rotated about an axis passing at the center of the wafer 1066 for adjustment in position. The level-1 and -2 corrections are made upon calculation of a position error caused by variations in moving speed of the stage and an error caused by positional deviation of dies as described above. In the level-2 correction, a feed-forward correction is made for the deflector 1075 and an electrostatic deflector 1076 within the ExB separator 1064. As a result, a two-dimensional image is generated at all times for a region in which the same patterns of different dies are formed. Even if a positional deviation occurs due to another factor which causes a beam position to drift, no problem will arise because captured image is compared in sequence with a total of 25 images which include 24 images in which previously captured images are deviated in position up to ±2 pixels in the X-axis direction and Y-axis direction and an image without positional deviation.

Figure 16:
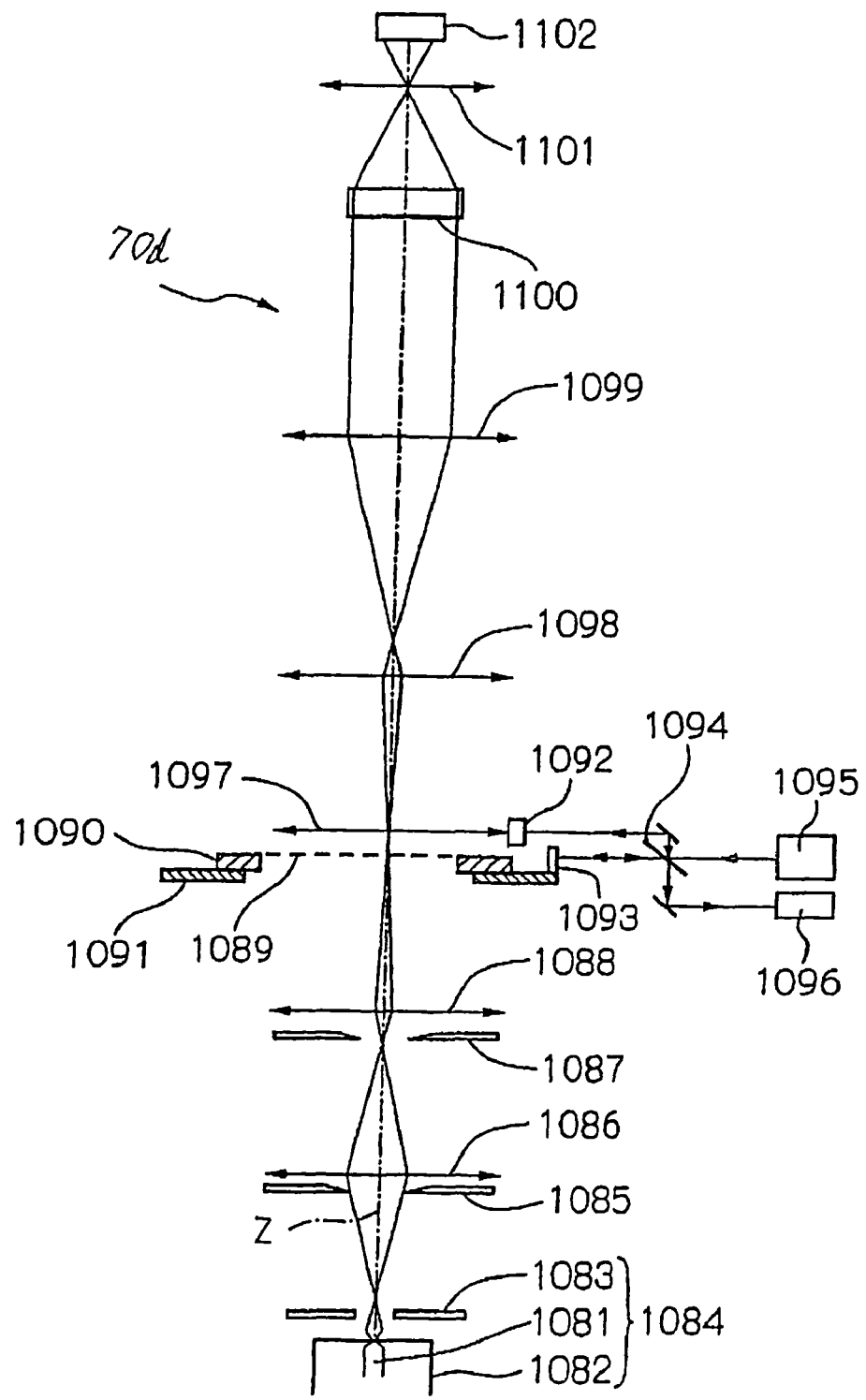
FIG. 16 shows a fifth embodiment of an electron beam apparatus according to the invention, in a case that a sample is transparent with regard to an electron beam.

FIG. 16 generally shows the configuration of a fifth embodiment of an electro-optical apparatus 70 for use in a testing apparatus according to the present invention, where a sample under testing is a stencil mask which transmits electrons. In the following, the configuration of the testing apparatus in FIG. 16 will be described in connection with a testing method which can be conducted in this apparatus.

In FIG. 16, an electron beam is emitted along an axis Z from electron gun 1084 which comprises a cathode 1081 made of LaB6, a Wehnelt 1082, and an anode 1083. The emitted electron beam is irradiated to a rectangular formation aperture 1085, and is formed into a rectangular shape by this aperture 1085 on a cross section perpendicular to the axis Z. The electron beam passing through the formation aperture 1085 and formed into a rectangular shape is converged by a condenser lens 1086 to form a cross-over on an NA aperture 1087. The electron beam passing through the NA aperture 1087 forms a rectangular image which is irradiated onto a stencil mask 1089, which is a mask under testing, by irradiation lens 1088.

In this regard, the stencil mask 1089 is fixed to a stage 1091 with its periphery chucked by an electrostatic chuck 1090. For measuring the position of the stage 1091 at all times, a laser length measuring machine which comprises a fixed mirror 1092, a movable mirror 1093, a fixed half mirror 1094, a laser oscillator 1095, and a laser receiver 1096 is provided, and the movable mirror 1093 is moved together with movements of the stage 1091. In this way, the laser length measuring machine finds the position of the stage 1091 based on a difference between a time taken by laser light emitted from the laser oscillator 1095 to return to the laser receiver 1096 after it is reflected by the fixed mirror 1092, and a time taken by the laser light emitted from the laser oscillator 1095 to return to the laser receiver 1096 after it is reflected by the movable mirror 1093. The position of the stage 1091 is accurately measured using this measurement result to register the stencil mask 1089. This will be later described.

In this way, the electron beam emitted from the electron gun 1084 passes through the stencil mask 1089, focuses on the main surface of an objective lens 1097 and is magnified thereby, and further is magnified by two magnification lenses 1098, 1099 before it is incident on the scintillator 1100. The scintillator 1100 converts the incident electron beam to a corresponding optical image, and the converted optical image is converted to an electric signal by a TDI detector 1102 after it is focused on an optical lens 1101. By processing this electric signal, a two-dimensional image related to one region under testing of the stencil mask 1089 can be captured.

The foregoing processing is performed for a sequence of regions under testing on the stencil mask 1089 with the stage 1091 moved in one direction, while the electron beam is emitted from the electron gun 1084. Next, the stage 1091 is moved, the electron beam is irradiated to the adjacent sequence of regions under testing to capture a two-dimensional image from the TDI detector 1102. Subsequently, a similar procedure is repeated to capture two-dimensional images over the entire region under testing, and the thus captured two-dimensional images can be sequentially processed to test the stencil mask 1089.

Here, the registration of the stencil mask 1089 will be described. For performing the registration, first, two patterns spaced by a definite interval on the stencil mask 1089 are included in a viewing field to capture a two-dimensional image thereof. After capturing the two-dimensional image in this way, a scaling factor when a region under testing of the stencil mask 1089 appears in the two-dimensional image is measured and stored. Using this stored scaling factor, the interval, and the number of pixels existing within the interval, the dimension a (nm/pixel) of one pixel in the stencil mask 1089 is calculated and also stored.

Next, the stage 1091 is moved to capture two-dimensional images of patterns at two different sites on the stencil mask 1089, and the position of the stage 1091 at the time the respective two-dimensional image was captured is measured by the aforementioned laser length measuring machine and stored. As a result, the posture of the stencil mask 1089 and its reference position are precisely determined from the captured two-dimensional images, their respective positions on the stage, and the aforementioned dimension a. In this way, the registration is completed.

Based on the registration thus determined, the stage 1091 is successively moved in one direction along the patterns of the stencil mask 1089, while image signals detected by the TDI detector 1102, associated with movements of the stage 1091, are integrated in the direction in which the stage 1091 is moved to capture a two-dimensional image with an improved S/N ratio. As a sequence of regions under testing has been completely scanned, a sequence adjacent thereto is similarly scanned to capture a two-dimensional image. By comparing the captured two-dimensional image with a reference pattern stored in a memory (not shown) of a computer, the TDI detector 1102 can test the stencil mask 1089 for defects which possibly exist in the patterns of the stencil mask 1089.

As described above, in the fifth embodiment of the electro-optical system 70 of the present invention, the dimension a of one pixel calculated by the aforementioned procedure is used prior to the registration, so that precise registration can be accomplished even if the scaling factor varies. In this regard, if the scaling factor deviates beyond a tolerance, the scaling factor may be adjusted to the tolerance by zooming the magnification lenses 1098 and 1099.

Figure 17:
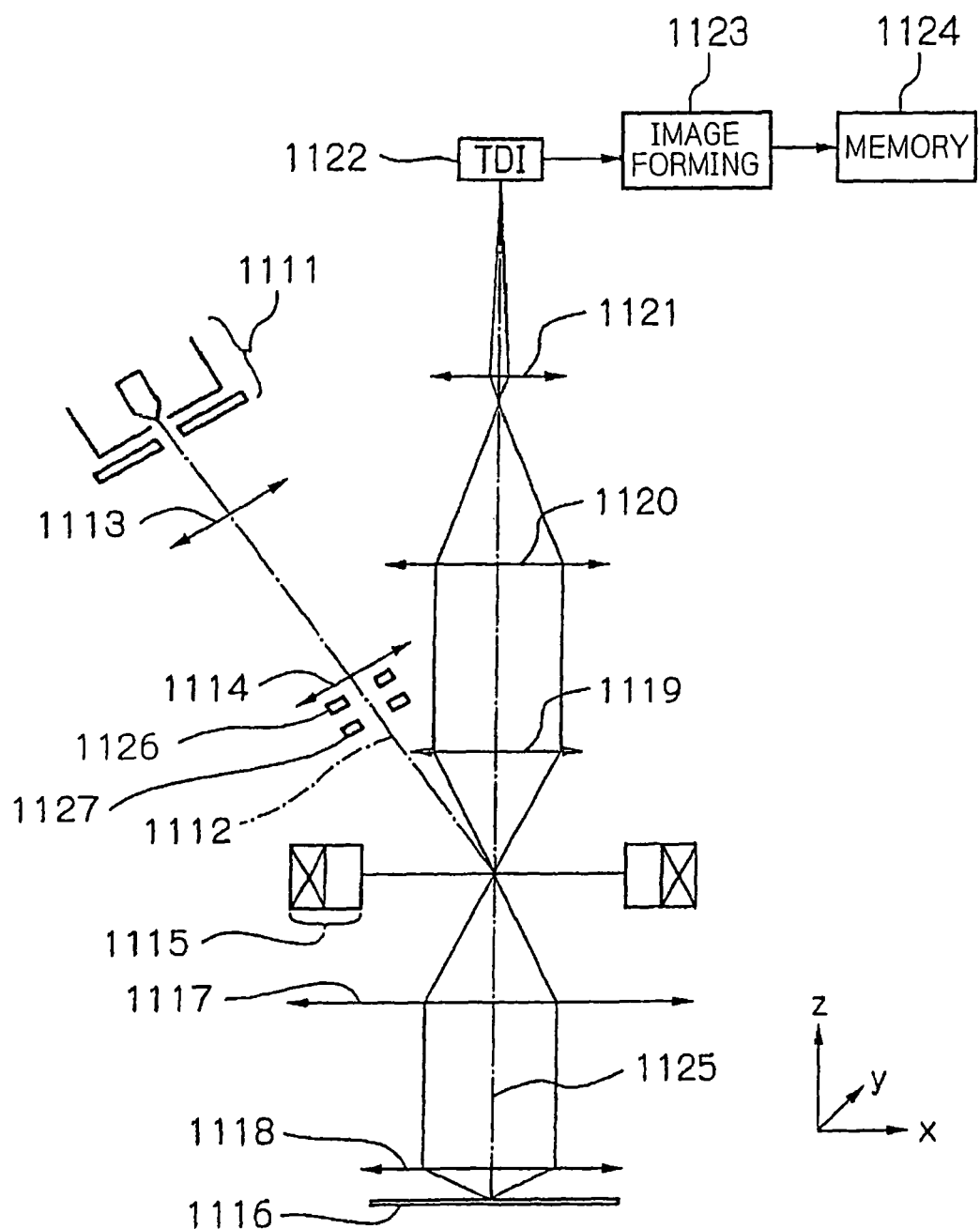
FIG. 17 shows a sixth embodiment of an electron beam apparatus according to the invention, in a case that a sample is not transparent with regard to an electron beam.

FIG. 17 is a diagram generally showing the configuration of a sixth embodiment of an electro-optical apparatus 70 for use in a testing apparatus according to the present invention. In FIG. 17, a non-transmissive wafer is under testing. In the following, the configuration of the sixth embodiment will be described in connection with a testing procedure implemented in this apparatus. In FIG. 17, an electron beam emitted from an electron gun 111, in which a thermion emitting cathode is operated under a space charge limited condition, is formed into a rectangular shape by a condenser lens 113, an irradiation lens 114, a beam formation aperture (not shown), and an NA aperture (not shown) arranged along an optical axis 112 of a primary optical system, and enters an ExB separator 1115. Here, the traveling direction of the electron beam is bent from the optical axis 1112 to a direction perpendicularly going toward a wafer 1116, passes through an objective lens tablet comprised of a first objective lens 1117 and a second objective lens 1118, and is irradiated to the wafer 1116. Similar to FIG. 16, the wafer 1116 is fixed on a stage (not shown), and the position of the stage is observed by a laser interferometer (not shown).

Secondary electrons generated from the wafer 1116 with the irradiation of the electron beam are magnified by a projection optical system comprised of a first objective lens 1117, a second objective lens 1118 and three magnification lenses 1119, 1120 and 1121. The thus magnified electron beam is detected by a TDI detector 1122 which is sensitive to electron beams for conversion to a corresponding electric signal. This electric signal is supplied to an image forming circuit 1123 which forms a two-dimensional image corresponding to the secondary electrons generated from the wafer 1116. This two-dimensional image is stored in a pattern memory 1124.

Here, the acquisition of two-dimensional images from the entire regions under testing of the wafer 1116 will be described. In FIG. 18, assuming a coordinate system which defines the z-axis along the optical axis 1125 of a secondary optical system, the x-axis perpendicular to the z-axis and parallel to the sheet surface of FIG. 17, and the y-axis perpendicular to these z-axis and x-axis, an electron beam emitted from the electron gun 1111 is formed into a rectangular shape as described above, and is irradiated to a rectangular region 1131 elongated in the y-axis direction (a portion indicated by shading in FIG. 18(A)) on the surface of the wafer 1116. This region 1131 is moved in the x-axis direction by a distance corresponding to a stripe width 1132 of a pattern formed on the wafer 1116 in association with the electron beam deflected by deflectors 1126, 1127. In this way, an elongated section (called the "scanning field of view") 1133 elongated in the x-axis direction is scanned on the surface of the wafer 1116, and simultaneously, the wafer 1116 is successively moved in the y-direction together with the stage. In this way, one stripe of the wafer 1116 is scanned in the x- and y-directions, and associated with the scanning, an image of secondary electrons generated from the wafer 1116 is captured, followed by the completion of the scanning of the stripe. Next, the stage is moved in the x-direction by one stripe width, and the next stripe is scanned to capture an image.

Since the surface of the wafer 1116 is not always flat, a focusing condition is measured on the sample surface for storage, prior to the capturing of the image in the sixth embodiment of the present invention. For measuring this focusing condition, a concentration distribution, for example is observed on the surface of the wafer 1116. For this purpose, as shown in FIG. 18(B), the image of a scanning field of view 1135 including an appropriate pattern 1134 is captured within the surface of the wafer 1116 to measure a concentration distribution in the x-axis direction. Assume that as a result, a concentration distribution 1136 is measured as shown in FIG. 18(C), by way of example. Now, a distance Δx is calculated in the scanning field of view 1135 for the concentration increasing from 12% to 88%. This distance Δx is calculated each time a voltage $V_{48}$ applied to the objective lens 1118 is changed, a curve 1137 representative of the relationship between Δx and $V_{48}$ is calculated, as shown in FIG. 18(D), and the voltage value $V_{48}$ (min) to the objective lens 1118 is found when the curve 1137 gives a minimum value. In this way, a voltage value is found corresponding to one scanning field of view. Such processing is performed over the entire regions under testing of the wafer 1116 to find each scanning field of view and the voltage value $V_{48}$ (min) corresponding thereto.

Next, the wafer 1116 is registered in a procedure similar to that described in connection with FIG. 16. First, a two-dimensional image is captured with two patterns spaced by a definite interval on the sample included in a viewing field. After capturing the two-dimensional image in this way, a scaling factor when a region under testing of the wafer 1116 appears in the two-dimensional image is measured and stored. Using this stored scaling factor, the interval, and the number of pixels existing within the interval, the dimension a (nm/pixel) of one pixel in the wafer 1116 is calculated and also stored.

Next, two-dimensional images of patterns are captured at two different sites on the wafer 1116 while the stage is moved, and the position of the stage at the time the respective two-dimensional image was captured is measured by the aforementioned laser length measuring machine and stored. As a result, the posture of the wafer 1116 and its reference position are precisely determined from the captured two-dimensional images, their respective positions on the stage, and the aforementioned dimension a. In this way, the registration is completed.

Since the dimension a of one pixel calculated in the aforementioned procedure is used to perform the registration, precise registration can be achieved even if the scaling factor varies. In this regard, if the scaling factor deviates beyond a tolerance, the scaling factor may be adjusted to the tolerance by zooming the magnification lenses 1120 and 1121.

Based on the registration thus determined, the stage is successively moved in one direction along the patterns of the wafer 1116, while image signals detected by the TDI detector 1122, associated with movements of the stage, are integrated in the direction in which the stage is moved to capture a two-dimensional image with an improved S/N ratio. As a sequence of regions under testing has been completely scanned, a sequence adjacent thereto is similarly scanned to capture a two-dimensional image. By comparing the captured two-dimensional image with a reference pattern stored in a memory (not shown) of a computer, the TDI detector 1122 can test the wafer 1116 for defects which possibly exist in the patterns of the wafer 1116. When the two-dimensional image of the wafer 1116 is captured in this way, an excitation voltage for the objective lens 1118 is set in each scanning field of view, i.e., at each position of the stage, to the voltage value V48 (min) previously found for the position. In this way, the condition for the lenses in the projection optical system can be matched with a focusing condition to capture the two-dimensional image.

It should be understood that the fifth and sixth embodiments of the present invention are not limited to those so far described. For example, while a procedure has been described in connection with the electro-optical apparatus of the configuration shown in FIG. 17 for setting lenses to match with a focusing condition when a two-dimensional image is captured from a non-transmissive sample such as a wafer, a similar procedure can be executed using the electro-optical apparatus of the configuration shown in FIG. 16 to set lenses to match with a focusing condition, even when the sample is a transmissive one such as a stencil mask.

Figure 19:
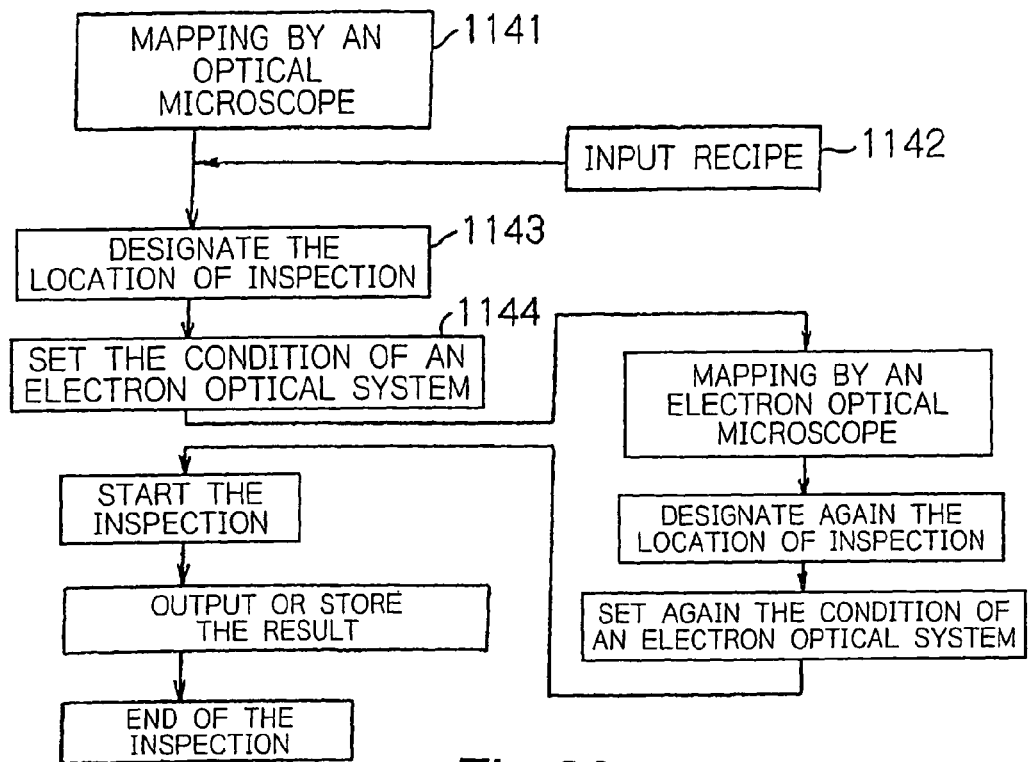
FIG. 19 is a flowchart showing an inspection procedure in a semiconductor device manufacturing method.

Turning now to FIG. 19, a procedure in an inspection process of a wafer will be explained. For the reason that a defect inspection apparatus using an electron beam is typically expensive and its throughput is relatively low as compared to other processing apparatuses, in the current circumstances, it is used after the essential processes considered to need the inspection most (e.g., the etching, the film deposition or the CMP (Chemical Mechanical Polishing) flattening processes), or in the wiring process especially in the fine pitch wiring process, or the first and second wiring processes and a gate wiring process prior thereto.

The wafer to be inspected is, after having been aligned on an ultra-precision X-Y stage via an atmospheric transfer system and a vacuum transfer system, fixed by an electrostatic chuck mechanism or the like, to which the defect inspection or the like may be applied in accordance with a procedure shown in FIG. 19. Firstly, an optical microscope is used to perform a position recognition of each die and/or a detection of height of each location, as desired, which are then stored (Step 1141). The optical microscope additionally takes any other optical microscopic images of desired locations, such as defects which may be also used in the comparison with an electron beam image. Secondly, information on recipe in association with the type of wafer (e.g., after which process?, wafer size 200 mm? or 300 mm? and so on) is input to the apparatus (Step 1142), and then, after completing the steps of specifying an inspection site (1143), setting an electron optical system (Step 1143) and setting an inspection condition (Step 1144) and so on, a defect inspection is performed while executing the image taking, typically in real time. The cell-to-cell comparison, die-to-die comparison and the like may be executed for inspection by a high-speed information processing system containing an algorithm, and the result may be output to a CRT or the like and/or stored in a memory appropriately as desired.

The defect may include a particle defect, an abnormal shape (a pattern defect), an electrical defect (including disconnection in a wiring or a via and bad conduction) and so on, and those defects can be distinguished and/or the classification of the size of the defect and the identification of a killer defect (a serious defect making the chip no longer usable) can be carried out at real time. The detection of the electrical defect may be achieved by detecting an abnormal contrast. For example, the location of bad conduction can be distinguished from the location of normal conduction from the fact that the former is typically charged to be positive by the irradiation of an electron beam (at about 500 eV) and thereby the contrast is deteriorated. As an electron beam irradiation means for applying the charge, a low potential (low energy) electron beam generating means (for emitting thermion, UV/photoelectron) may be installed for emphasizing the contrast owing to a potential difference, in addition to an electron beam irradiating means used for a typical inspection. Prior to the irradiation of the electron beam for the inspection onto a region subject to the inspection, this low potential (energy) electron beam is generated and irradiated thereto. In the case of the image projection method, which can charge the wafer to be positive by irradiating the electron beam for the inspection onto the wafer, depending on the specification thereof, the electron beam generating means of low potential need not be installed additionally. Further, the defect can be detected from a difference in contrast (resultant from a difference in flow-ability depending on the forward or backward direction of the device) caused by applying a positive or negative potential relative to a reference potential to a sample such as a wafer. This is applicable to a line width measuring apparatus and an overlay accuracy measuring, as well.

Figure 20:
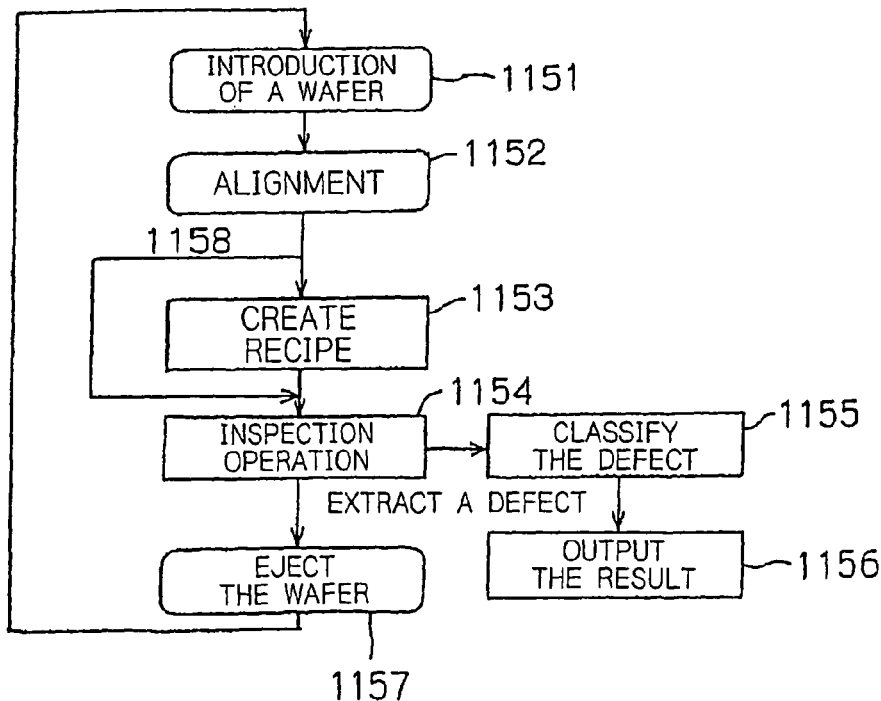
FIG. 20 is a flowchart showing a basic inspection procedure in a semiconductor device manufacturing method.

The inspection of a sample, such as a wafer, by using an electron beam can be performed in accordance with a basic procedure as shown in FIG. 20. Firstly, in Step 1151, the wafer is introduced onto a stage by a transfer mechanism. Typically, a plurality (e.g., 25 pieces) of wafers to be inspected are accommodated in a cassette holder and one or more of them are simultaneously taken out of it and mounted on the stage of a defect inspection apparatus, wherein, since the defect inspection apparatus is installed in a housing kept in a vacuum condition, a device for interfacing between the atmosphere and the vacuum is necessary in order to carrying out the operation for taking the wafer subject to the inspection out of the cassette holder and mounting it on the stage and the operation for taking the wafer having finished with the inspection out of the housing. To this end, when the wafer is to be introduced, the wafer that has been taken out of the cassette holder is firstly cleaned in a mini-environment unit and then transferred into a loading chamber. Since the loading chamber is coupled with the housing via a shutter, once the wafer is transferred into the loading chamber, the loading chamber is evacuated into vacuum. After the loading chamber is evacuated to vacuum, the shutter is opened so as to allow a communication between the loading chamber and the housing, wherein the wafer finished with the inspection is removed from the stage and taken out of the housing, while at the same time, another wafer to be inspected is transferred from the loading chamber to the housing and then loaded on the stage.

Next, in step 1152, an aligning operation is performed so as to make the wafer aligned. When the wafer is loaded on the stage from the loading chamber, usually, the X- and the Y-axes of a die on the wafer are not in conformity with the moving direction of the stage or the scanning direction of the electron beam. In this condition, in order to perform an accurate inspection for the die on the wafer, firstly the wafer is rotated on the stage to compensate for an angular misalignment of the die so that the axes defining the die on the wafer are matched with the moving direction of the stage or the scanning direction of the electron beam. This operation is referred to as an alignment operation.

After the alignment operation of Step 1152, Step 1153 for creating the recipe to set a condition or the like on the inspection is performed. At least one type of recipe is necessary for the wafer subject to the inspection, while in order to satisfy a plurality of conditions on the inspection, occasionally a plurality of recipe may be prepared for a single wafer subject to the inspection. Further, if there is a plurality of wafers subject to the inspection, which have identical patterns, only one recipe may be used for the inspection of said plurality of wafers. In the case of the inspection using the previously created recipe, it is not necessary to create a new recipe before the inspection operation.

Next, in Step 1154, the inspection operation is carried out in accordance with the condition and sequence defined in the recipe, and thus the wafer is inspected. The defect extraction is executed immediately upon each discovery of the defect during the inspection operation, and the extracted defect is classified in Step 1155, in which the data on the location and others of the extracted defect is accumulated together with the classification data and the image of the defect, while the defect information, such as the location of the defect, on the extracted defect may be displayed on the operating screen (Step 1156). In this way, when the inspection of the wafer is completed, the wafer is ejected (Step 1157), and the next wafer is transferred in position, on which a series of above steps are repeated. It is to be noted that the path 1158 indicates that if the previously prepared recipe is used in the inspection, the creation of a new recipe is not necessary prior to the inspection operation.

In FIG. 20, the inspection operation (Step 1154) executes the inspection of the wafer in accordance with the condition and sequence described in the recipe. The defect extraction is executed immediately at each time when the defect is found during the inspection operation, and the following operations from a) to c) are performed substantially in parallel.
  a) The defect classification (Step 1155) is executed, and the data on the extracted defect and the data on the defect classification are added to a file for outputting the result.
  b) An image of the extracted defect is added to a file for outputting the result exclusively for the image or the file for outputting the result specified in said a) (Step 1156).
  c) The defect data such as the location of the extracted defect is indicated on the operating screen.

Once the inspection has been completed as per each wafer subject to the inspection, then the following operations from a) to c) are performed substantially in parallel.
  a) The file for outputting the result is closed and saved.
  b) When the external communication requests the inspection result, in response thereto the inspection result is sent.
  c) The wafer is ejected.

In the case where the serial inspection of the wafers is set, the next wafer to be inspected is transferred and the above operations are repeated.

The flow in FIG. 20 will be described further in detail.
(1) Making of Recipe (Step 1153)

The recipe is a file for setting a condition or the like involved in the inspection and also can be saved. The recipe is used during or before the inspection so as to make a setting for the apparatus, and the condition on the inspection defined in the recipe includes:
  a) The die subject to the inspection;
  b) The region subject to the inspection within the die;
  c) The inspection algorithm;
  d) The condition for detection (conditions required in the defect extraction, including the inspection sensibility and the like); and
  e) The condition for observation (conditions required in the observation, including the magnification, the lens voltage, the stage speed, the sequence of inspection and so on). The inspection algorithm of c) will be described later more specifically.

Figure 21:
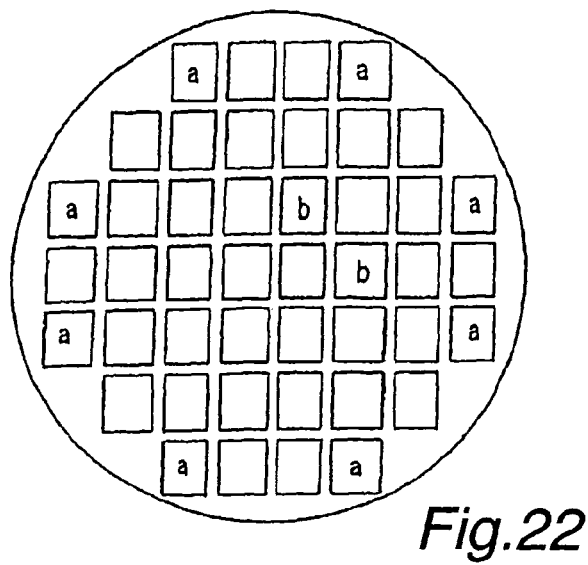
FIG. 21 is a diagram illustrating dies which are set as inspection dies.

Among those items listed above, the setting of the die subject to the inspection may be performed by an operator who designates the die to be inspected on a die map diagram displayed in the operating screen, as shown in FIG. 21. In the example illustrated in FIG. 21, the die "a" located in an edge area of the wafer and the die "b" that has been determined to be defective beyond any doubt in the previous step are grayed out to preclude them from the inspection, and the rest of the dies are subject to the inspection. The apparatus further includes a function for designating the die subject to inspection automatically based on the distance from the edge of the wafer and/or the information on whether the die is good or bad, which has been detected in the previous step.

Figure 22:
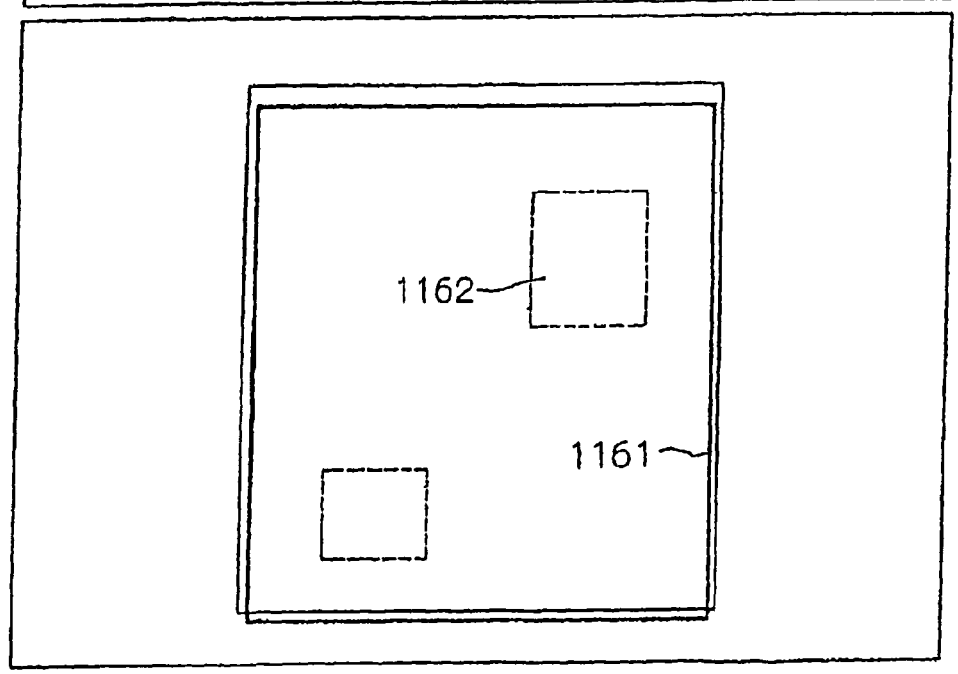
FIG. 22 is a diagram illustrating inspection areas of a die.

Further, to set the region subject to the inspection within the die, the operator may designate the region subject to the inspection on a diagram for setting a region to be inspected within the die displayed in the operating screen as shown in FIG. 22, by using an input device, such as a mouse, based on the image obtained by the optical microscope or the EB microscope. In the example illustrated in FIG. 22, the region 1161 indicated by the solid line and the region 1162 indicated by the broken line have been set as the regions subject to the inspection.

The region 1161 includes substantially entire area of the die that has been set as the region subject to the inspection. The inspection algorithm specifies the adjacent die comparison method (i.e., the die-to-die inspection), in which the details of the condition on the detection and the condition on the observation applied to this region may be separately established. As for the region 1162, the inspection algorithm specifies the array inspection (i.e., cell-to-cell inspection), in which the details of the condition on the detection and the condition on the observation applied to this region may be separately established. This means that it is possible to set a plurality of regions subject to the inspection, and for each of those regions subject to the inspection, the individual conditions on the inspection algorithm and/or on the inspection sensibility can be set respectively. Further, the regions subject to the inspection can be placed on one another, and in this case, different sets of inspection algorithm may be applied to the same region simultaneously.
(2) Inspection Operation (Step 1154)

Figure 23:
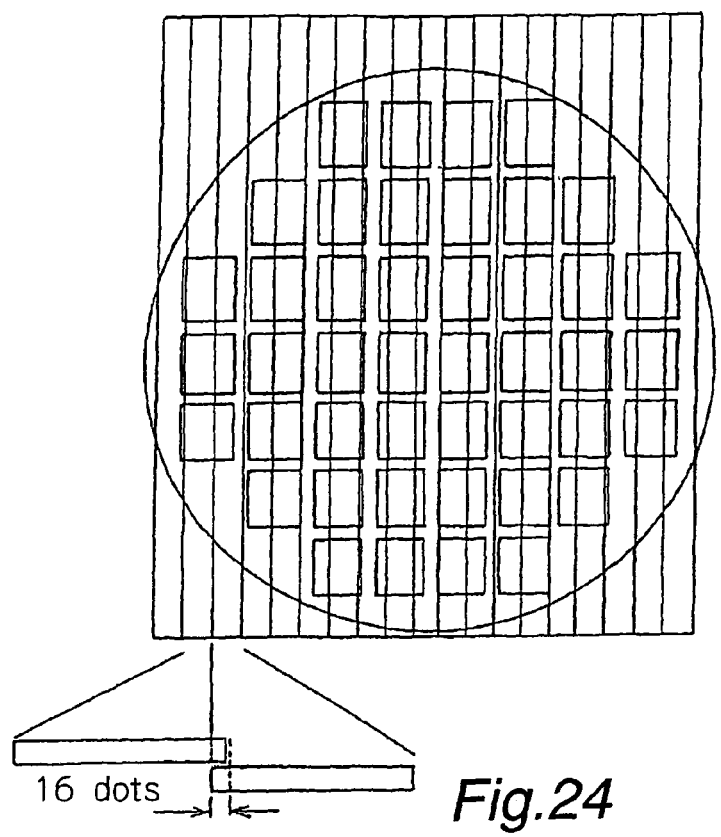
FIG. 23 shows diagrams for explaining an inspection procedure in a semiconductor device manufacturing method.

In the inspection operation, the wafer subject to the inspection is divided into segments each defined by a certain scanning width as shown in FIG. 23 and scanned. The scanning width is determined substantially based on a length of the line sensor, and the line sensor is arranged such that the end portions of the line sensor are slightly overlapped with each other. This is intended to provide a correct judgment on the continuity between lines when the detected defects are to be processed integrally in a final stage and to ensure an extra margin for the image alignment when the comparative inspection is carried out. The amount of overlapping may be about 16 dots for the 2048 dots of line sensor.

Figure 24:
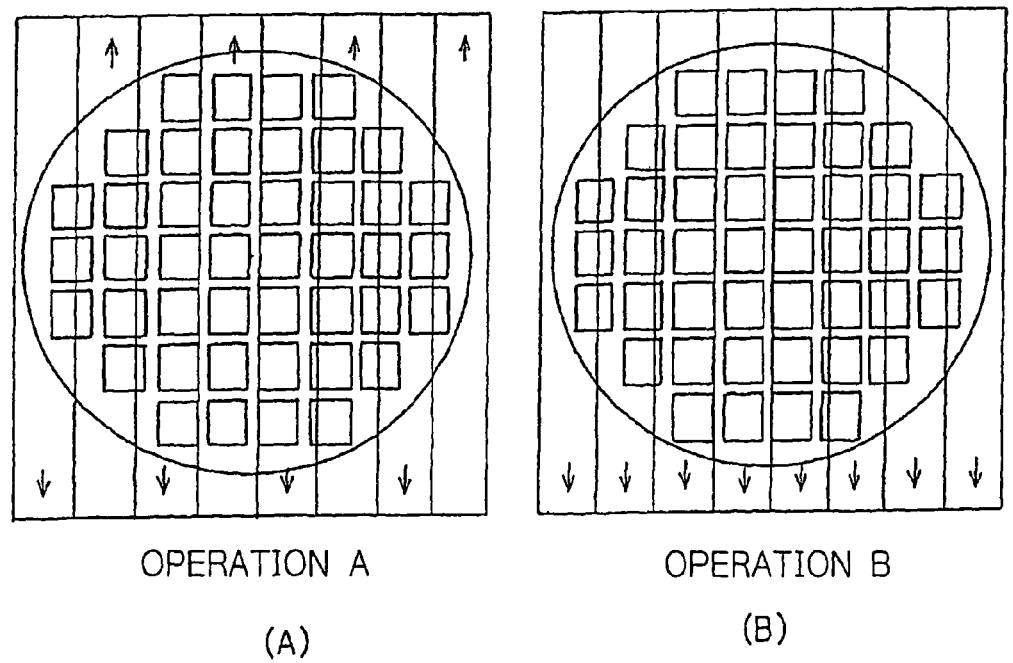
FIGS. 24A and 24B are diagrams for explaining an inspection procedure in a semiconductor device manufacturing method.
Figure 25:
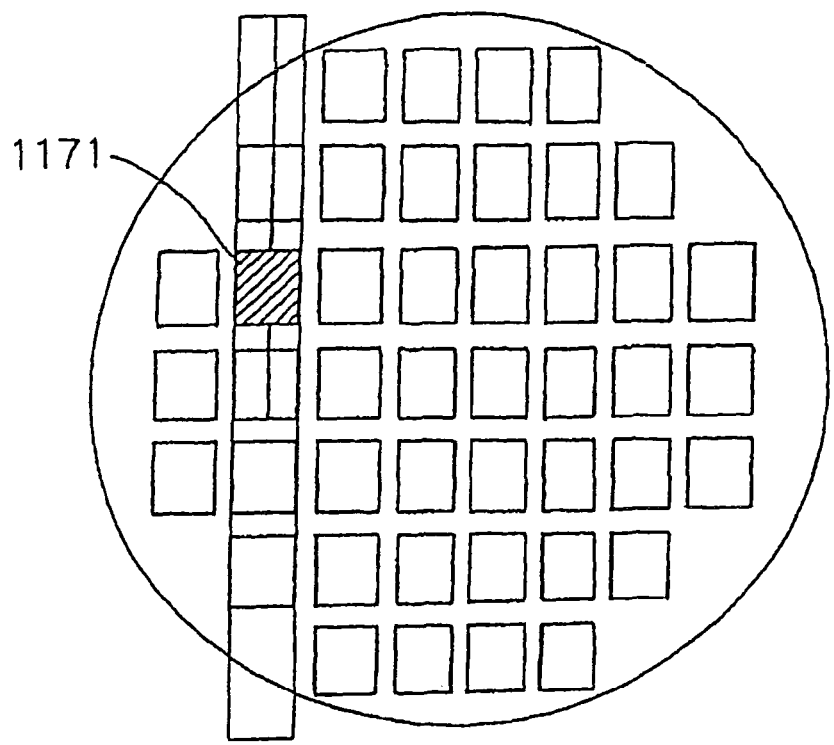
FIG. 25 is a diagram for explaining a scanning method of a die to be inspected in a semiconductor device manufacturing method.

FIG. 24(A) and FIG. 24(B) schematically show the direction and sequence of the scanning operation, respectively. The operator may select either one of a bi-directional operation "A" aiming for reducing the inspection time or a unidirectional operation B due to the mechanical constraint. Further, the apparatus has a function for automatically calculating an operation for reducing the scanning amount based on the setting in the recipe for the die subject to the inspection and for carrying out this operation. FIG. 25 illustrates an example of scanning operation for a case where there is a single die 1171 subject to the inspection, wherein an unnecessary scanning operation is not performed.

The algorithm to be implemented in the present apparatus may be categorized principally into two types: an array inspection (Cell inspection); and a random inspection (Die inspection). The random inspection may be further classified depending on the object to be compared as follows;
a) An adjacent die comparison method (Die-Die inspection);
b) A reference die comparison method (Die-Any die inspection); and
c) A CAD data comparison method (Cad Data-Any Die inspection).

A method generally referred to as a golden template method includes b) the reference die comparison method and c) the CAD data comparison method, wherein in the reference die comparison method, the reference die is used as the golden template, and in the CAD data comparison method, the CAD data is used as the golden template. An operation in accordance with each algorithm will be described below.

(1) Array Inspection (Cell Inspection)

The array inspection may be applied to the inspection of a cyclic structure. One example thereof may be represented by a DRAM cell. In this inspection, an image to be inspected is compared with a reference image and a difference therebetween is extracted,as a defect. The reference image and the image subject to the inspection may be either one of a two-valued image or a multi-valued image for improving the detection precision. The difference between the reference image and the image subject to the inspection may be in itself treated as the detected defect, and a secondary determination for avoiding a detection error may be further performed based on the difference data, including a differential amount of the detected difference and a total area of the pixels containing the difference.

In the array inspection, the comparison between the reference image and the image subject to the inspection may be carried out on a structural cycle basis. That is, the comparison may be performed by every structural cycle while reading out the images that have been obtained at once by a CCD, or otherwise if the reference image is defined by n structural cycles, the comparison may be performed by every n structural cycle.

Figure 26:
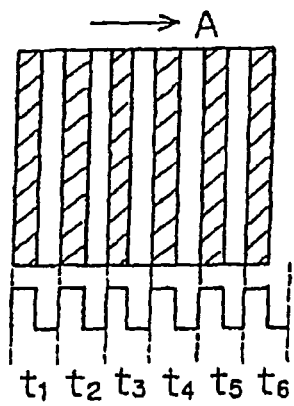
FIG. 26 shows diagrams for explaining a reference image generation method in an inspection procedure in a semiconductor device manufacturing method.

One example of a method for generating the reference image is shown in FIG. 26, in which an example for making the comparison by every structural cycle is illustrated so as to represent single structural cycle generation. The same method may be employed to make the number of cycles to n. On the assumption, the direction of the inspection in FIG. 26 is indicated by an arrow A. Besides, the cycle indicated by $t_4$ denotes a cycle subject to the inspection. Since the operator can input a size representing the cycle while watching the screen, therefore the cycles $t_1$ to $t_6$ can be easily identified in FIG. 26.

A reference cycle image may be generated by adding the data in the cycles $t_1$ to $t_3$ just before the cycle subject to the inspection in each pixel and averaging the result. Even if a defect is contained in either one of the $t_1$ to $t_3$ cycle images, they are averaged and consequently less affective to the outcome. Thus formed reference cycle image and the image of the cycle $t_4$ to be inspected are compared to each other to extract the defect.

In the next step, when the image of the cycle $t_5$ subject to the inspection is to be inspected, the data in the cycles $t_2$ to $t_4$ are added and averaged to thereby generate the reference cycle image. In the following steps of inspection, the reference cycle image may be generated successively in a similar manner from the images obtained before the image of the cycle to be inspected having been taken so as to continue the inspection operation.

(2) Random Inspection (Die Inspection)

The random inspection may be applied without restriction of the structure of a die. In the inspection, an image subject to the inspection is compared with a reference image as an image to be referred to and a difference therebetween is extracted as a defect. The reference image and the image subject to the inspection may be either one of a two-valued image or a multi-valued image for improving the detection precision. The difference between the reference image and the image subject to the inspection may be in itself treated as the detected defect, and a secondary determination for avoiding a detection error may be further performed based on the difference data, including a differential amount of the detected difference and a total area of the pixels containing the difference.

The random inspection may be classified based on how to determine the reference image. An operation specific to the method for determining the reference image will now be described.

A. An Adjacent Die Comparison Method (Die-Die Inspection)

Figure 27:
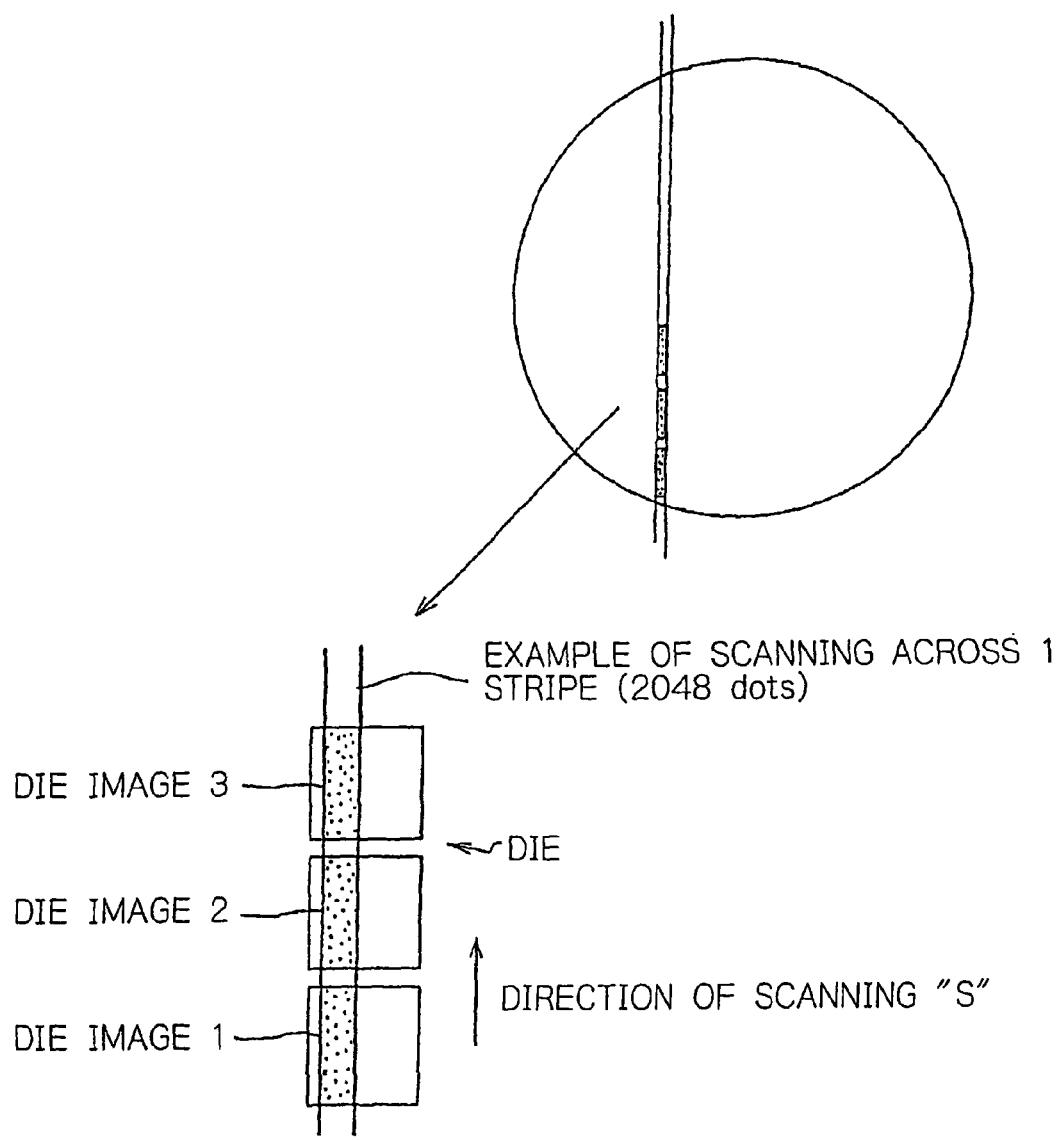
FIG. 27 shows diagrams for explaining an adjacent-die comparison method in an inspection procedure in a semiconductor device manufacturing method.
Figure 28:
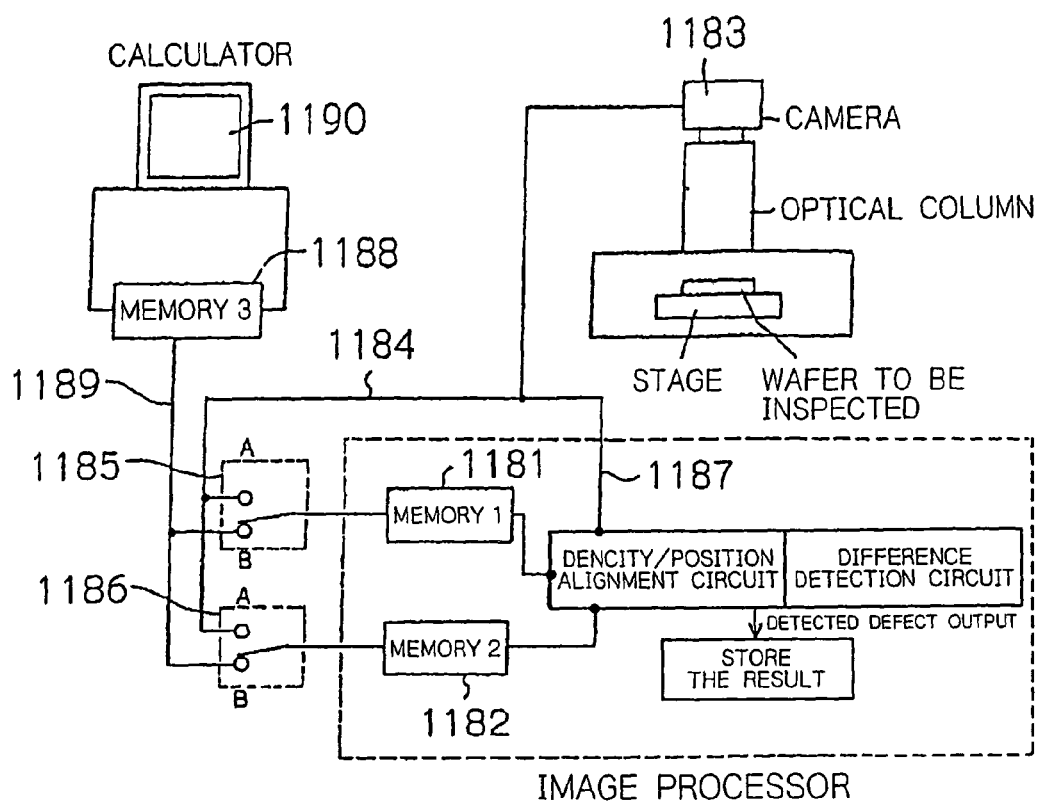
FIG. 28 shows a diagram for explaining a system in which an adjacent-die comparison method in an inspection procedure in a semiconductor device manufacturing method, is executed.

The reference image is an image of a die adjacent to another die whose image is to be inspected. The image of a die subject to the inspection is compared with two reference images of dies located adjacent to said die subject to the inspection to thereby determine a defect. This method is illustrated in FIG. 28, wherein under a condition where a switch 1185 and a switch 1186 are set such that a memory 1181 and a memory 1182 of an image processor are connected to a path 1184 from a camera 1183, the following steps a) through i) are executed.

a) A step of storing a die image 1 (FIG. 27) from the path 1184 into the memory 1181 in accordance with a scanning direction "S".
 b) A step of storing a die image 2 from the path 1184 into the memory 1182.
 c) A step of obtaining the die image 2 from the path 1187 in synchronization with said step b), and comparing the thus obtained die image 2 with the image data stored in the memory 1181, which represent the data in the same relative position in the die, to thereby determine a difference between them.
 d) A step of saving the difference from Step c).
 e) A step of storing a die image 3 from the path 1184 into the memory 1181.
 f) A step of obtaining the die image 3 from the path 1187 in synchronization with Step e), and comparing the thus obtained die image 3 with the image data stored in the memory 1182, which represent the data in the same relative position in the die, to thereby determine a difference between them.

g) A step of saving the difference from Step f).

h) A step of determining a defect in the die image 2 from the results stored in Steps d) and g).

i) A step of sequentially repeating Steps a) through h) on a series of dies.

Depending on the specific setting, prior to the step of determining the differences in Steps c) and f), the compensation may be applied so as to cancel the positional difference between two images to be compared (position alignment). Alternatively, the compensation may be applied so as to cancel the density difference therebetween (density alignment). Otherwise, both of the alignments may be applied.

B. A Reference Die Comparison Method (Die-Any Die Inspection)

Figure 29:
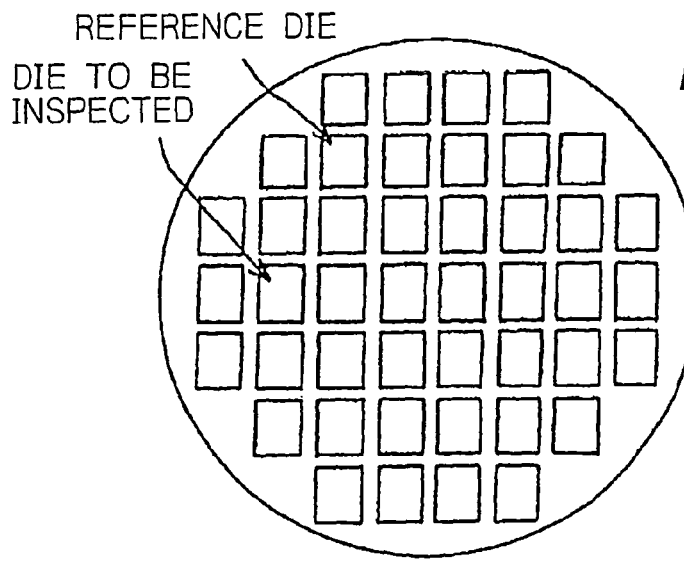
FIG. 29 shows a diagram for explaining a reference-die comparison method in an inspection procedure in a semiconductor device manufacturing method.
Figure 30:
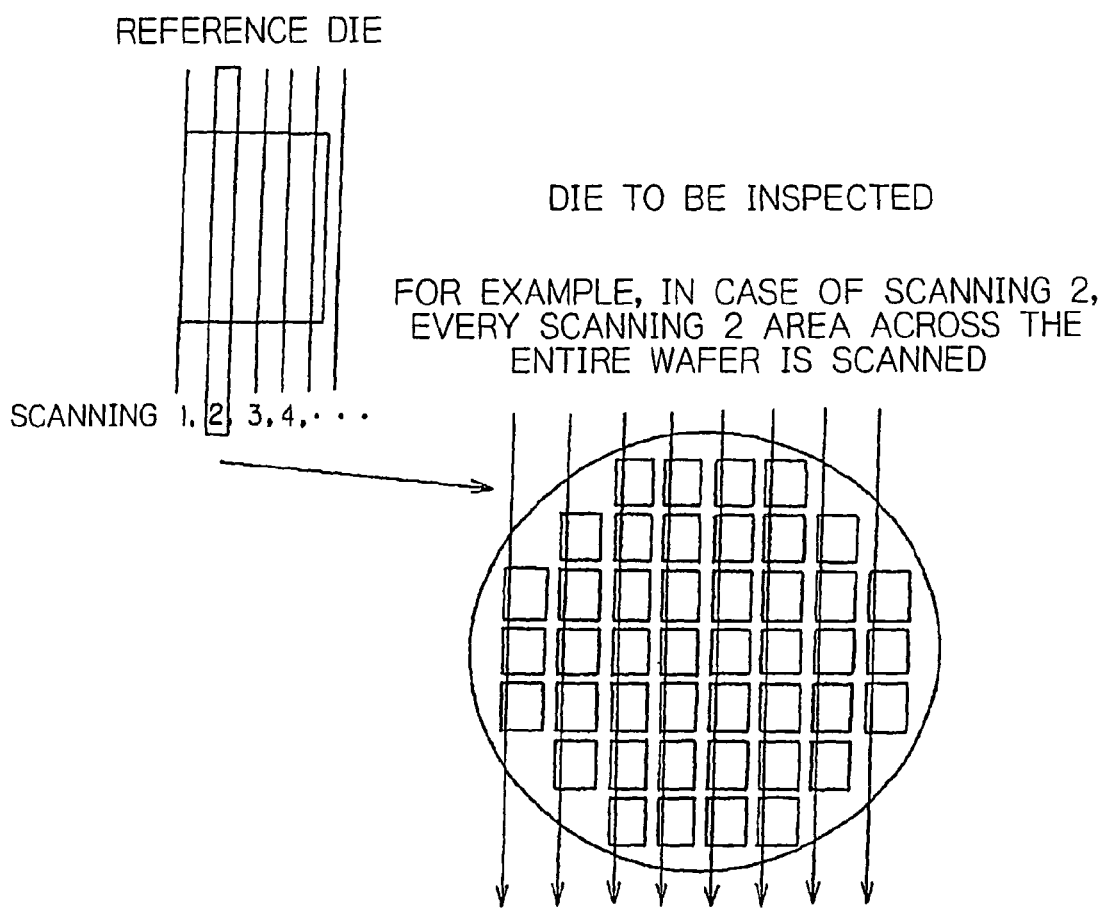
FIG. 30 shows diagrams for explaining a reference-die comparison method in an inspection procedure in a semiconductor device manufacturing method.

The operator designates a reference die. The reference die may be a die existing on the wafer or another die whose image has been stored prior to the inspection, and first of all, the reference die is scanned or the image having stored in advance is transferred so that the image may be stored in a memory as a reference image. Steps a) through h) to be carried out in this method will be described below with reference to FIGS. 28 and 29.

a) A step of selecting by the operator the reference die from the dies on the wafer subject to the inspection or from the die images having been stored prior to the inspection.

b) In the case of the reference die existing on the wafer subject to the inspection, a step of setting the switch 1185 and the switch 1186 such that at least either one of the memory 1181 or the memory 1182 of the image processor is connected to the path 1184 from the camera 1183.

c) In the case of the reference image being represented by the die image having been stored prior to the inspection, a step of setting the switch 1185 and the switch 1186 such that at least either one of the memory 1181 or the memory 1182 of the image processor is connected to the path 1189 from a memory 1188 storing the reference image representing the die image.

d) In the case of the reference die existing on the wafer subject to the inspection, a step of scanning the reference die and transferring the reference image representing the reference die image into a memory of the image processor.

e) In the case of the reference image being represented by the die image having been stored prior to the inspection, a step of transferring the reference image representing the reference die image into the memory of the image processor without any necessity for the step of scanning.

f) A step of comparing the images obtained by scanning the dies subject to the inspection in sequence with the image in the memory formed by the transferred reference image which is the reference die image and/or the image in which the data in the same relative position in the die is the same, and thereby determining a difference therebetween.

g) A step of determining a defect from the difference obtained in Step f).

h) A step of repeating said procedure as defined in the above Steps d) through g) by inspecting the scanning position of the reference and the portion on the die to be inspected, which corresponds to the scanning position on the reference die, across the entire area of the wafer continuously, as shown in FIG. 30, while changing the scanning position on the reference die until the die to be inspected is entirely inspected.

Depending on the specific setting, prior to the step of determining the differences in Step f), the compensation may be applied so as to cancel the positional difference between two images to be compared (position alignment). Alternatively, the compensation may be applied so as to cancel the density difference therebetween (density alignment). Otherwise, both of the alignments may be applied.

In Step d) or e), the reference die image stored in the memory of the image processor may be an entire image of the reference die or a partial image thereof, and if the partial image of the reference die is taken as the reference die image, then the partial image of the reference die shall be renewed continuously during the inspection.

C. A CAD Data Comparison Method (CadData-AnyDie Inspection)

Figure 31:
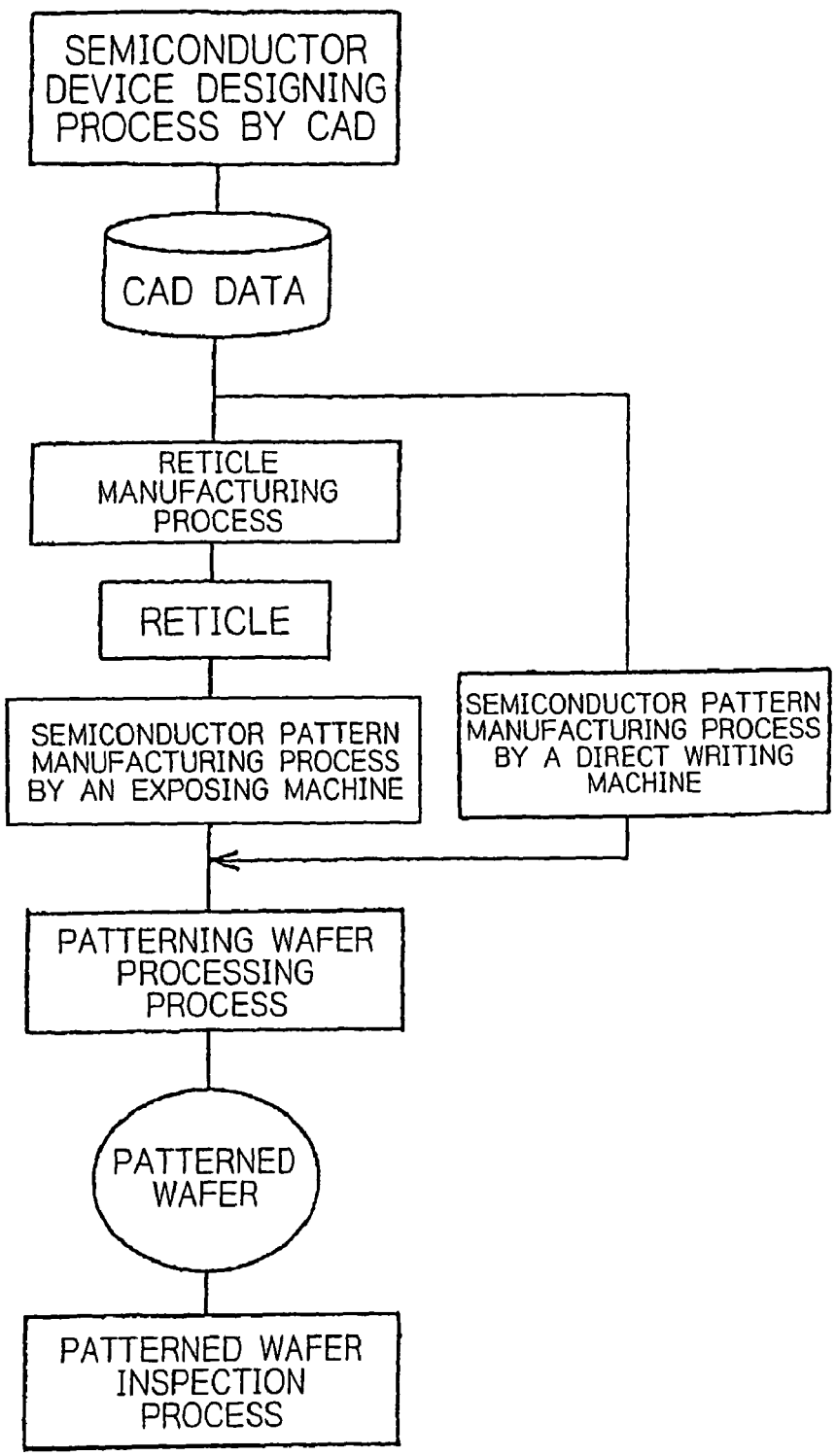
FIG. 31 is a flowchart for explaining a reference-die comparison method in an inspection procedure in a semiconductor device manufacturing method.

In the semiconductor manufacturing process shown in FIG. 31, a reference image is made from the CAD data representing an output from the semiconductor pattern designing step by the CAD, as an image to be referred to. The reference image may an entire image of the die or a partial image thereof containing the area to be inspected.

Since the CAD data is typically represented by the vector data, it cannot be used directly as the data for the reference image, unless it is converted to the raster data corresponding to the image data obtained by the scanning operation. Accordingly the vector data representing the CAD data should be converted into the raster data, and this conversion may be executed for each unit defined by the scanning width of the image obtained by scanning the die subject to the inspection during the inspection. At that time, the conversion may be applied to the image data representing the same relative position on the die as of an image expected to be obtained by scanning the die subject to the inspection. The inspection scanning and the conversion task may be performed as they are overlapped.

The above conversion task from the vector data to the raster data may be added with at least one of the following functions:

a) A function of making the raster data multi-valued;

b) A function of, in conjunction with said a), setting a gradient weighting and/or an offsetting in making the data multi-valued, by taking the sensibility of the inspection apparatus into account; and c) A function of, after the vector data is converted into the raster data, performing an image processing for processing pixels, including expanding and contracting of the pixels.

In FIG. 28, the inspection steps by way of the CAD data comparison method include the following Steps a) through f):

a) A step of converting the CAD data into the raster data by a calculator 1190, and making a reference image with said additional function and storing it in the memory 1188;

b) A step of setting the switch 1185 and the switch 1186 such that at least either one of the memory 1181 or the memory 1182 of the image processor is connected to the path 1184 from the memory 1188;

c) A step of transferring the reference image in the memory 1188 to a memory in the image processor;

d) A step of comparing the images obtained by scanning the image subject to the inspection in sequence with the image in the memory formed by the transferred reference image and/or the image in which the data in the same relative position in the die is the same, and thereby determining a difference therebetween;

e) A step of determining a defect from the difference obtained in Step d); and f) A step of repeating said procedure as defined in the above Steps a) through e) by inspecting the scanning position of the reference die and the portion on the die to be inspected, corresponds to the scanning position on the reference die, across the entire area of the wafer continuously, as shown in FIG. 30, while changing the scanning position on the reference die until the die to be inspected is entirely inspected.

Depending on the specific setting, prior to the step of determining the differences in said d), the compensation may be applied so as to cancel the positional difference between two images to be compared (position alignment). Alternatively, the compensation may be applied so as to cancel the density difference therebetween (density alignment). Otherwise, both of said alignments may be applied.

In Step c), the reference die image stored in the memory of the image processor may be an entire image of the reference die or a partial image thereof, and if the partial image of the reference die is taken as the reference die image, then the partial image of the reference die shall be renewed continuously during the inspection.

(3) Focus mapping

Figure 32:
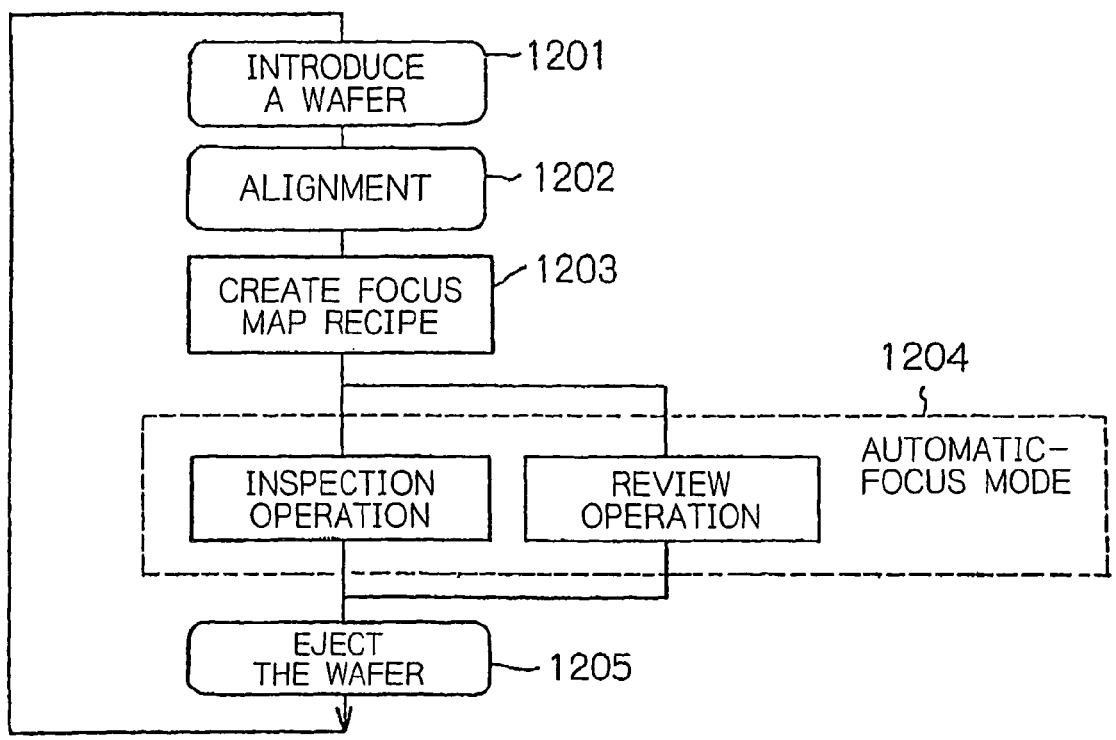
FIG. 32 is a flowchart for explaining a focus mapping in an inspection procedure in a semiconductor device manufacturing method.

FIG. 32 shows a basic flow of the focusing function. Firstly, after a wafer transfer (Step 1201) including an alignment operation (Step 1202), a recipe is made, which specifies a condition and the like on involving the inspection. One of the recipes is a focus map recipe (Step 1203), and according to the focusing information specified in this recipe, an inspection operation and a reviewing operation are executed in the automatic-focusing mode (Step 1204). After this, the wafer is ejected (Step 1205).

A procedure for making the focus map recipe along with a procedure for operating the automatic-focusing will be described below.

1. Procedure for Making the Focus Map Recipe

Figure 33:
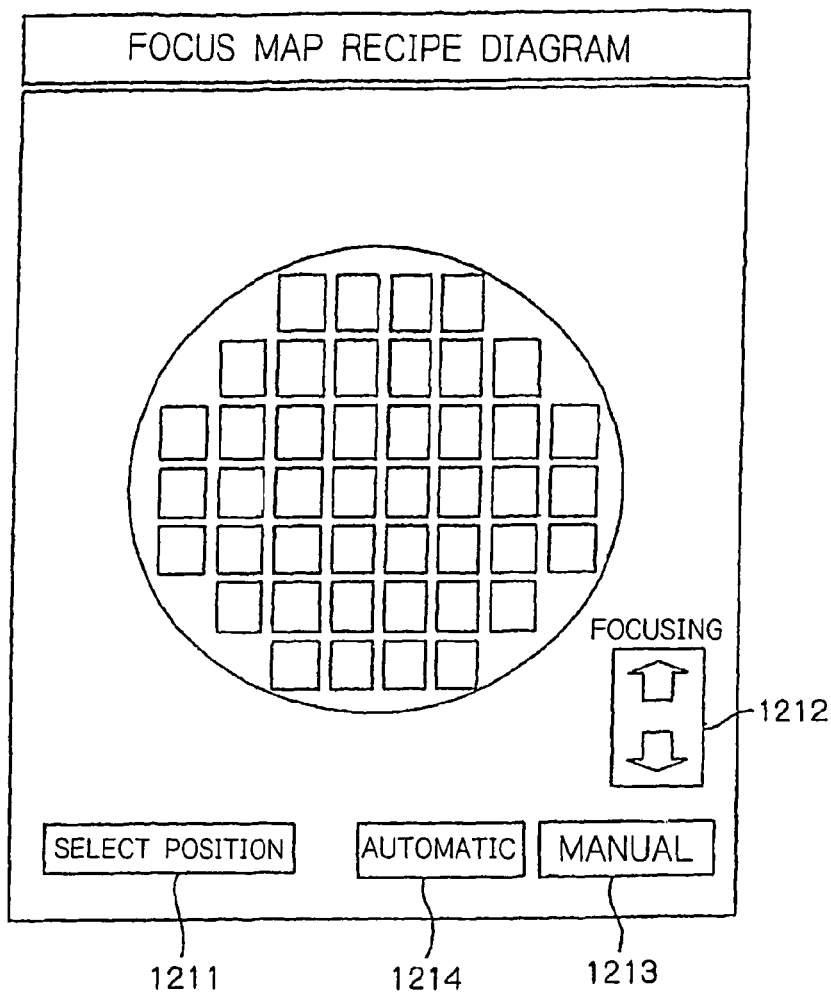
FIG. 33 is a diagram for explaining a focus mapping in an inspection procedure in a semiconductor device manufacturing method.

The focus map recipe has its independent input screen, and the operator can make the recipe by executing the following steps a) through c).

a) A step of inputting a focus map coordinate, such as a position of die and/or a pattern in a die, to which the focus value is to be input by means of a position selecting switch 1211 of FIG. 33;

b) A step of setting a die pattern, which is required in automatic measuring of the focus value (it is to be noted that this step may be skipped if the focus value is not measured automatically); and c) A step of setting a best focus value on the focus map coordinate determined in Step a).

It is to be noted that in Step a), the operator can designate any desired die, and alternatively it is possible to make a setting such that the operator may select all of the dies or every n pieces of dies. Further, the operator can select as an input screen a diagram schematically representing an array of dies within the wafer or an image using an actual image.

In Step c), the operator can set the best focus value on manual by using a manual switch 1213 in FIG. 33, or can select and set it automatically by using a focus switch 1212 operative in association with the voltage value of a focusing electrode or by using an auto-switch 1214.

2. Procedure for Measuring the Focus Value

Figure 34:
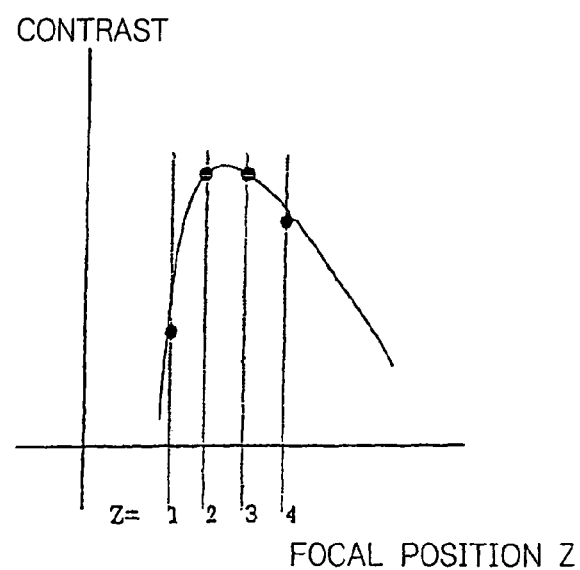
FIG. 34 is a diagram for explaining a focus mapping in an inspection procedure in a semiconductor device manufacturing method.

An exemplary procedure for automatically determining a focus value in the above Step c) includes:

a) A step of obtaining an image with the focus position Z=1 and calculating its contrast, as shown in FIG. 34;

b) A step of performing Step a) with respect to Z=2, 3 and 4, respectively;

c) A step of determining a contrast function through a regression from the contrast values obtained in Steps a) and b), and d) A step of determining by an arithmetic operation the Z that can give a maximum value of the contrast function, and setting this value as the best focus value.

For example, if such a line and a space as shown in FIG. 35 are chosen as the die pattern necessary for automatically measuring the focus value, a good result will be obtained. The contrast is measurable, if it includes a black and white pattern, regardless of its shape.

By executing the above Steps a) through d), the best focus value on one point can be determined. A data format at this time is represented by (X, Y, Z), or a set of the coordinate XY used in the determination of the focus with the best focus value Z, meaning that the focus map coordinate number (X, Y, Z) determined in the focus map recipe is existing. This is a part of the focus map recipe, and is referred to as a focus map file.

3. Procedure for Operating the Automatic-Focusing

A method for setting the best focus based on the focus map recipe, during the inspection operation for obtaining an image and the reviewing operation, may be performed in a following manner.

Firstly, the position data is further subdivided based on the focus map file 1 made at the time of making the focus map recipe, and the best focus at that time is determined by the calculation to thereby make a subdivided focus map file 2. This calculation is executed by using an interpolation function, which may be specified by the operator during making the focus map recipe, for example, as a linear interpolation, a spline interpolation or the like. Secondly, the XY position of the stage is monitored, and a voltage to be applied to the focusing electrode is changed to the focus value specified in the focus map file 2.

To explain more specifically, in FIGS. 36(A) through (C), assuming that a black dot indicates the focus value in the focus map file 1 and a white dot indicates the focus value in the focus map file 2, then the focus values in the focus map file is used to interpolate the focus values in the focus map file, and the Z coordinate of the focusing position is changed in association with the scanning so as to maintain the best focusing. At that time, in the space between the specified points (indicated by the white dots) in the focus map file, a current value is used until the next changing point is encountered.

Figure 37:
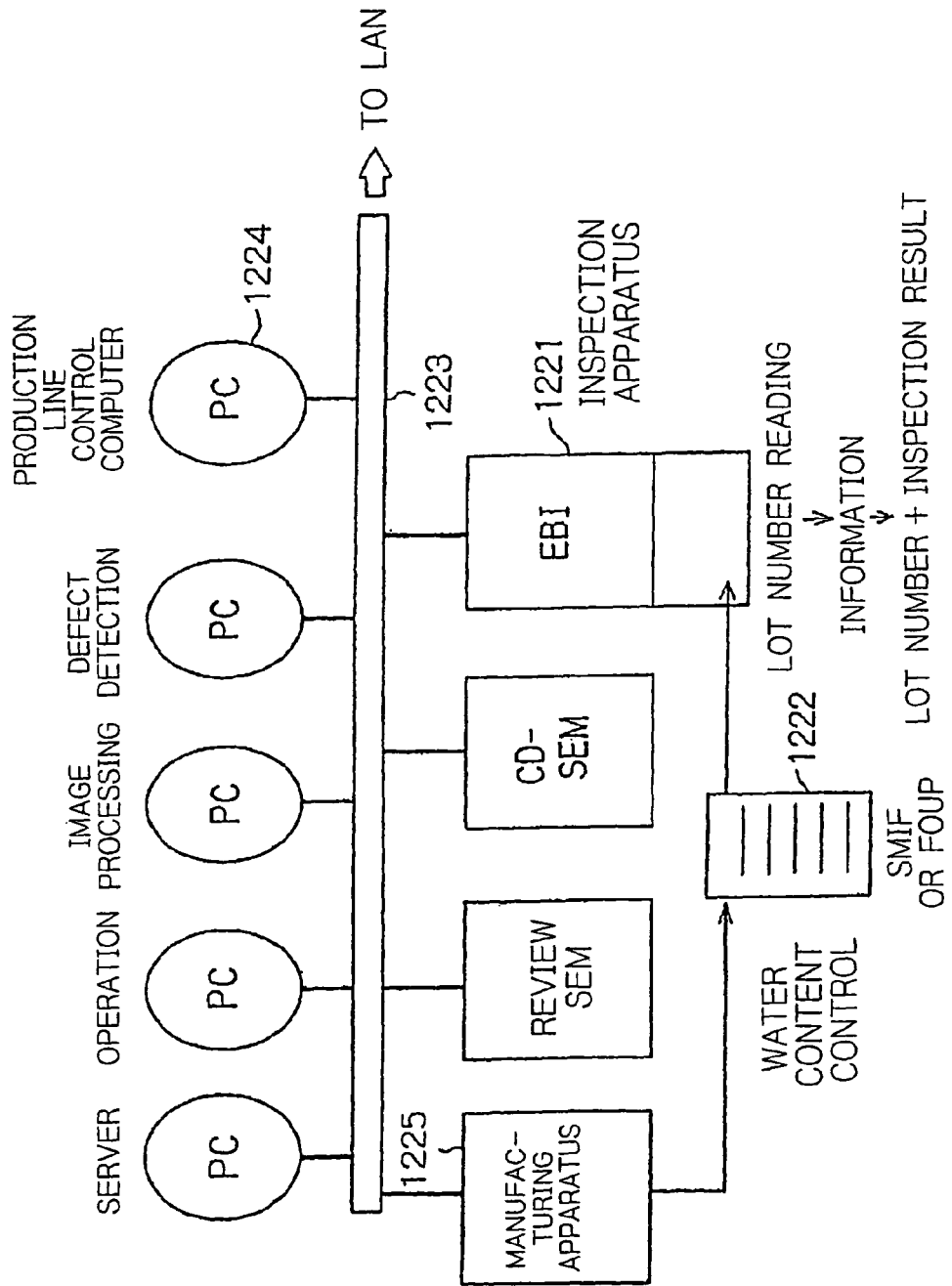
FIG. 37 shows a manufacturing line to which an electron beam apparatus according to the invention is coupled.

FIG. 37 shows an example of the manufacturing line using a defect inspection apparatus according to the present invention. It is designed such that the information, including a lot number of a wafer subject to the inspection with the inspection apparatus 1221 and a history indicating specific manufacturing apparatuses used to manufacture said wafer, can be read out of the memory arranged in the SMIF or FOUP 1222, or otherwise its lot number can be identified by reading the ID number of the SMIF, FOUP or the wafer cassette.

The defect inspection apparatus 1221 is adapted to be connected with a network system of a production line, and via this network system 1223, it can send the information such as a lot number of a wafer representing an object to be inspected and a result from inspection on the wafer to a production line controlling computer 1224 that controls the production line, respective manufacturing apparatuses 1225, and other inspection apparatuses. The manufacturing apparatus may include lithography-related apparatuses, such as an exposure, a coater, a curing device, and a developer, or a film deposition apparatus, such as an etching device, a sputtering device and a CVD device, a CMP apparatus, a variety of types of measuring apparatuses and other inspection apparatuses.

In the inspection of the wafer, it is preferred from the viewpoint of the resolution that an image of a surface of the wafer can be obtained by controlling the electron beam to impinge upon the wafer and detecting the secondary electrons emanated from the wafer. Based on this understanding, the description has been so far centered mainly to the secondary electrons, the reflected electrons or the back-scattered electrons. However, the electrons to be detected may be any types of electrons in so far as the information on the surface of the substrate can be obtained therefrom, including, for example, mirror electrons (in a broad sense, referred to as reflected electrons) that do not directly impinge upon the substrate but are reflected in the vicinity of the substrate owing to the negative electric field formed in that region, or transmission electrons that are transmittable through the substrate. Especially, for the case of using the mirror electrons, in which the electrons do not directly impinge upon the sample, the effect of the charge-up can advantageously be made extremely low.

For the case of using the mirror electrons, a negative potential lower than the accelerating voltage is applied to the wafer, so that the negative electric field can be formed in the vicinity of the wafer. This negative potential should be favorably set to such a value sufficient to cause almost all of the electrons to be returned in the vicinity of the surface of the wafer. Specifically, the potential should be set to a value lower than the accelerating electrons by 0.5 to 1.0V or more. For example, in the present invention, for the case of accelerating voltage of −4 kV, preferably, the voltage to be applied to the sample should be in a range of −4.0005 kV to −40050 kV. More preferably, it should be in a range of −4.0005 kV to −40020 kV, and most preferably in a range of −4.0005 kV to −4.010 kV.

Further, for the case of using the transmission electrons, when the accelerating voltage is set at −4 kV, the voltage to be applied to the wafer should be in a range of 0 to −4 kV, preferably in a range of 0 to −3.9 kV, and more preferably in a range of 0 to −3.5 kV. Further, a light ray or an X-ray may be used. These rays are satisfactorily applicable to the alignment, the secondary system and the die comparison in the defect inspection apparatus according to the present invention.

Further, the electrons or the secondary beam to be detected in the defect inspection apparatus according to the present invention may be of any types in so far as the information on the sample surface is contained therein, including, not only the secondary electrons, the reflected electrons (also referred to as the mirror electrons) and the back-scattered electrons, but also those reflected electrons that are reflected in the vicinity of the sample without making the primary beam impinge upon the sample with the aid of the negative electric field formed in the vicinity of the sample. Further, the primary beam is not limited to the electrons but may be a light ray. In the case of the primary beam represented by the light ray, the secondary beam is also the light ray, and in the case of the UV ray to be used, the secondary beam may be formed by the electrons.

The present invention has been described with reference some embodiments, and it is understandable that an electron beam apparatus according to the invention is capable of reducing problems which are caused by stage guide distortion, orthogonal errors of the stage guide and so on, and inspecting with a high accurate and high throughput even if a stage is not located at a predetermined position, dies on a wafer are not located in line with theoretical ideal coordinate and/or a moving speed is not constant.

The invention claimed is:

1. An electron beam apparatus for inspecting a pattern on a sample using an electron beam, comprising:

first processing means for calculating a coordinate error $(\Delta x, \Delta y)$ of a measured XY coordinate $(x,y)$ of each of arbitrary reference points on the sample from a calculated ideal position XY coordinate of the reference point;

second processing means for calculating an orthogonal error of the XY coordinates based on the calculated coordinate errors;

third processing means for calculating an error due to mirror distortion of an interferometer of the electron beam apparatus on the basis of the calculated coordinate errors;

orthogonal error correcting means for compensating the measured XY coordinates $(x,y)$ on the basis of the calculated orthogonal error upon inspecting the sample; and beam deflection correcting means for compensating deflection by a beam deflector disposed in a second electro-optical system on the basis of the calculated mirror distortion error upon inspecting the sample.

2. The electron beam apparatus according to claim 1, wherein:

the second and third processing means comprise recursive processing means for obtaining coefficients $a_1 \sim e_1$ and $a_2 \sim e_2$ which satisfy the following Equations (1) and (2), through recursive processing:

$$\Delta x = a_1 + b_1 x + c_1 y + d_1 x^2 + e_1 y^2 \quad (1)$$

$$\Delta y = a_2 + b_2 x + c_2 y + d_2 x^2 + e_2 y^2 \quad (2)$$

the second processing means further comprises means for calculating the orthogonal error of the XY coordinate system as a difference between the obtained coefficients c1 and b2; and the third processing means further comprises means for calculating the coordinate error $(\Delta x, \Delta y)$ as the mirror distortion error, by substituting a XY coordinate $(x,y)$ provided from the interferometer upon driving the electron beam apparatus, into equations which are derived by substituting the obtained coefficients $d_1$, $d_2$, $e_1$ and $e_2$ into the following Equations (3) and (4):

$$\Delta x = d_1 x^2 + e_1 y^2 \quad (3)$$

$$\Delta y = d_2 x^2 + e_2 y^2 \quad (4).$$

3. The electron beam apparatus according to claim 1, wherein:

the second and third processing means comprise recursive processing means for obtaining coefficients $a_1 \sim e_1$ and $a_2 \sim e_2$ which satisfy the following Equations (1) and (2), through recursive processing:

$$\Delta x = a_1 + b_1 x + c_1 y + d_1 x^2 + e_1 y^2 \quad (1)$$

$$\Delta y = a^2 + b_2 x + c_2 y + d_2 x^2 + e_2 y^2 \quad (2)$$

the second processing means further comprises means for calculating the orthogonal error of the XY coordinate system as a difference between the obtained coefficients c1 and b2 ; and the third processing means further comprises:

recursive processing means for obtaining coefficients $a_1 \sim e_1$ and $a_2 \sim e_2$ which satisfy Equations (1) and (2) through recursive processing, on the basis of the coordinate error $(\Delta x, \Delta y)$ obtained by the first processing means after the orthogonal error has been corrected by the orthogonal error correcting means; and means for calculating the coordinate error ($\Delta x, \Delta y$) as the mirror distortion error, by substituting a XY coordinate (x,y) provided from the interferometer upon driving the electron beam apparatus, into equations which are derived by substituting the obtained coefficients $a_1 \sim e_1$ and $a_2 \sim e_2$.

4. The electron beam apparatus according to claim 1, wherein:

the second processing means comprises:

recursive processing means for obtaining coefficients $a_1 \sim c_1$ and $a_2 \sim c_2$ which satisfy the following Equations (1) and (2), through recursive processing:

$$\Delta x = a_1 + b_1 x + c_1 y \quad (1)$$

$$\Delta y = a_2 + b_2 x + c_2 y \quad (2), \text{and}$$

means for calculating the orthogonal error of the XY coordinate system as a difference between the obtained coefficients c1 and b2; and the third processing means comprises:

recursive processing means for obtaining coefficients $d_1, e_1, d_2$ and $e_2$ which satisfy the following Equations (3) and (4), through recursive processing:

$$\Delta x = d_1 x^2 + e_1 y^2 \quad (3)$$

$$\Delta y = d_2 x^2 + e_2 y^2 \quad (4), \text{and}$$

means for calculating the coordinate error ($\Delta x, \Delta y$) as the mirror distortion error, by substituting a XY coordinate (x,y) provided from the interferometer upon driving the electron beam apparatus, into equations which are derived by substituting the obtained coefficients $d_1, e_1, d_2$ and $e_2$ into Equations (3) and (4).

5. The electron beam apparatus according to claim 1, wherein:

the second processing means comprises:

recursive processing means for obtaining coefficients $a_1 \sim c_1$ and $a_2 \sim c_2$ which satisfy the following Equations (1) and (2), through recursive processing:

$$\Delta x = a_1 + b_1 x + c_1 y \quad (1)$$

$$\Delta y = a_2 + b_2 x + c_2 y \quad (2), \text{and}$$

means for calculating the orthogonal error of the XY coordinate system as a difference between the obtained coefficients c1 and b2; and the third processing means comprises:

recursive processing means for obtaining coefficients $a_1 \sim e_1$ and $a_2 \sim e_2$ which satisfy the following Equations (3) and (4), through recursive processing:

$$\Delta x = a_1 + b_1 x + c_1 y + d_1 x^2 + e_1 y^2 \quad (3)$$

$$\Delta y = a_2 + b_2 x + c_2 y + d_2 x^2 + e_2 y^2 \quad (4)$$

means for calculating the coordinate error ($\Delta x, \Delta y$) as the mirror distortion error, by substituting a XY coordinate (x,y) provided from the interferometer upon driving the electron beam apparatus, into equations which are derived by substituting the obtained coefficients $a_1 \sim e_1$ and $a_2 \sim e_2$ into Equations (3) and (4).

6. The electron beam apparatus according to claim 2, further comprising:

means for compensating shift amounts in the X-axis direction and Y-axis direction by the coefficients $a_1$ and $a_2$ obtained by the recursive processing means; and means for compensating scale errors in the X-axis direction and Y-axis direction by the coefficients $b_1$ and $c_2$ obtained by the recursive processing means.

7. The electron beam apparatus according to claim 1, wherein the beam deflector comprises a deflection electrode; and the beam deflection compensation means is adapted to adjust a voltage to the deflection electrode.

8. The electron beam apparatus according to claim 1, further comprising:

means for detecting a secondary electron beam emitted from the sample by the irradiation of a primary electron beam;

means for capturing image information on the pattern on the sample surface on the basis of the output of the detecting means; and means for detecting a defect of the pattern by comparing the captured image information with image information on the same pattern at different positions on the same sample, or with image information on a reference pattern previously stored for comparison.

9. A method of compensating an error regarding a stage position in an electron beam apparatus for inspecting a pattern on a sample using an electron beam, comprising:

a first step of calculating a coordinate error ($\Delta x, \Delta y$) of a measured XY coordinate (x,y) of each of arbitrary reference points on the sample from a calculated ideal position XY coordinate of the reference point;

a second step of calculating an orthogonal error of the XY coordinates based on the calculated coordinate errors;

a third step of calculating an error due to mirror distortion of an interferometer of the electron beam apparatus on the basis of the calculated coordinate errors;

an orthogonal error correcting step of compensating the measured XY coordinates (x,y) on the basis of the calculated orthogonal error upon inspecting the sample; and a beam deflection correcting step of compensating deflection by a beam deflector disposed in a second electro-optical system on the basis of the calculated mirror distortion error upon inspecting the sample.

10. The method of compensating an error regarding a stage position according to claim 9, wherein:

the second and third processing steps comprise a recursive processing step of obtaining coefficients $a_1 \sim e_1$ and $a_2 \sim e_2$ which satisfy the following Equations (1) and (2), through recursive processing:

$$\Delta x = a_1 + b_1 x + c_1 y + d_1 x^2 + e_1 y^2 \quad (1)$$

$$\Delta y = a_2 + b_2 x + c_2 y + d_2 x^2 + e_2 y^2 \quad (2);$$

the second processing step further comprises the step of calculating the orthogonal error of the XY coordinate system as a difference between the obtained coefficients c1 and b2; and the third processing step further comprises the step of calculating the coordinate error ($\Delta x, \Delta y$) as the mirror distortion error, by substituting a XY coordinate (x,y) provided from the interferometer upon driving the electron beam apparatus, into equations which are derived by substituting the obtained coefficients $d_1, d_2, e_1$ and $e_2$ into the following Equations (3) and (4):

$$\Delta x = d_1 x^2 + e_1 y^2 \quad (3)$$

$$\Delta y = d_2 x^2 + e_2 y^2 \quad (4).$$

11. The method of compensating an error regarding a stage position according to claim 9, wherein:

the second and third processing steps comprise recursive processing means for obtaining coefficients $a_1$~$e_1$ and $a_2$~$e_2$ which satisfy the following Equations (1) and (2), through recursive processing:

$$\Delta x = a_1 + b_1 x + c_1 y + d_1 x^2 + e_1 y^2 \qquad (1)$$

$$\Delta y = a_2 + b_2 x + c_2 y + d_2 x^2 + e_2 y^2 \qquad (2), \text{ and}$$

the second processing step further comprises the step of calculating the orthogonal error of the XY coordinate system as a difference between the obtained coefficients c1 and b2; and the third processing step further comprises the steps of:
obtaining coefficients $a_1$~$e_1$ and $a_2$~$e_2$ which satisfy Equations (1) and (2) through recursive processing, on the basis of the coordinate error ($\Delta x, \Delta y$) obtained by the first processing step after the orthogonal error has been corrected by the orthogonal error correcting step; and calculating the coordinate error ($\Delta x, \Delta y$) as the mirror distortion error, by substituting a XY coordinate (x,y) provided from the interferometer upon driving the electron beam apparatus, into equations which are derived by substituting the obtained coefficients $a_1$~$e_1$ and $a_2$~$e_2$ into Equations (1) and (2).

12. The method of compensating an error regarding a stage position according to claim 9, wherein:

the second processing step comprises the steps of:
obtaining coefficients $a_1$~$c_1$ and $a_2$~$c_2$ which satisfy the following Equations (1) and (2), through recursive processing:

$$\Delta x = a_1 + b_1 x + c_1 y \qquad (1)$$

$$\Delta y = a_2 + b_2 x + c_2 y \qquad (2), \text{ and}$$

calculating the orthogonal error of the XY coordinate system as a difference between the obtained coefficients c1 and b2; and the third processing step comprises the steps of:
obtaining coefficients $d_1$, $e_1$, $d_2$ and $e_2$ which satisfy the following Equations (3) and (4), through recursive processing:

$$\Delta x = d_1 x^2 + e_1 y^2 \qquad (3)$$

$$\Delta y = d_2 x^2 + e_2 y^2 \qquad (4), \text{ and}$$

calculating the coordinate error ($\Delta x, \Delta y$) as the mirror distortion error, by substituting a XY coordinate (x,y) provided from the interferometer upon driving the electron beam apparatus, into equations which are derived by substituting the obtained coefficients $d_1$, $e_1$, $d_2$ and $e_2$ into Equations (3) and (4).

13. The method of compensating an error regarding a stage position according to claim 9 wherein:

the second processing step comprises the steps of:
obtaining coefficients $a_1$~$c_1$ and $a_2$~$c_2$ which satisfy the following Equations (1) and (2), through recursive processing:

$$\Delta x = a_1 + b_1 x + c_1 y \qquad (1)$$

$$\Delta y = a_2 + b_2 x + c_2 y \qquad (2), \text{ and}$$

calculating the orthogonal error of the XY coordinate system as a difference between the obtained coefficients c1 and b2; and the third processing step comprises:
obtaining coefficients $a_1$~$e_1$ and $a_2$~$e_2$ which satisfy the following Equations (3) and (4), through recursive processing:

$$\Delta x = a_1 + b_1 x + c_1 y + d_1 x^2 + e_1 y^2 \qquad (3)$$

$$\Delta y = a_2 + b_2 x + c_2 y + d_2 x^2 + e_2 y^2 \qquad (4);$$

calculating the coordinate error ($\Delta x, \Delta y$) as the mirror distortion error, by substituting a XY coordinate (x,y) provided from the interferometer upon driving the electron beam apparatus, into equations which are derived by substituting the obtained coefficients $a_1$~$e_1$ and $a_2$~$e_2$ into Equations (3) and (4).

14. The method of compensating an error regarding a stage position according to claim 10, further comprising the steps of:

compensating shift amounts in the X-axis direction and Y-axis direction by the coefficients $a_1$ and $a_2$ obtained at the recursive processing step; and compensating scale errors in the X-axis direction and Y-axis direction by the coefficients $b_1$ and $c_2$ obtained at the recursive processing step.

15. The method of compensating an error regarding a stage position according to claim 9, wherein the beam deflector comprises a deflection electrode; and the step of compensating beam deflection is executed by adjusting a voltage to the deflection electrode.

16. The method of compensating an error regarding a stage position according to claim 9, wherein the electron beam apparatus comprises:

means for detecting a secondary electron beam emitted from the sample by the irradiation of a primary electron beam;

means for capturing image information on the pattern on the sample surface on the basis of the output of the detecting means; and means for detecting a defect of the pattern by comparing the captured image information with image information on the same pattern at different positions on the same sample, or with image information on a reference pattern previously stored for comparison.

17. A computer program read and executed by a computer for executing a stage position error correcting method in an electron beam apparatus for inspecting a pattern on a sample using an electron beam, wherein the computer program executes the stage position error correcting method according to claim 9.

* * * * *